(12) United States Patent
Palle et al.

(10) Patent No.: US 9,284,316 B2
(45) Date of Patent: Mar. 15, 2016

(54) SUBSTITUTED FUSED PYRIMIDINE COMPOUNDS

(71) Applicant: Advinus Therapeutics Private Limited, Bangalore (IN)

(72) Inventors: Venkata Palle, Hinjewadi Pune (IN); Vidya Ramdas, Hinjewadi Pune (IN); Dinesh Barawkar, Hinjewadi Pune (IN); Sujay Basu, Hinjewadi Pune (IN); Summon Koul, Hinjewadi Pune (IN); Yogesh Waman, Hinjewadi Pune (IN); Meena Patel, Hinjewadi Pune (IN); Anil Panmand, Hinjewadi Pune (IN)

(73) Assignee: Advinus Therapeutics Private Limited, Bangalore (IN)

( * ) Notice: Subject to any disclaimer, the term of this patent is extended or adjusted under 35 U.S.C. 154(b) by 0 days.

(21) Appl. No.: 14/511,847

(22) Filed: Oct. 10, 2014

(65) Prior Publication Data

US 2015/0087643 A1    Mar. 26, 2015

Related U.S. Application Data

(62) Division of application No. 13/256,071, filed as application No. PCT/IN2010/000145 on Mar. 12, 2010, now Pat. No. 8,859,566.

(30) Foreign Application Priority Data

Mar. 13, 2009 (IN) .............. 571/CHE/2009

(51) Int. Cl.
| | |
|---|---|
| *A61K 31/522* | (2006.01) |
| *C07D 473/28* | (2006.01) |
| *C07D 473/40* | (2006.01) |
| *C07D 473/06* | (2006.01) |
| *C07D 473/18* | (2006.01) |
| *C07D 473/30* | (2006.01) |
| *A61K 31/5377* | (2006.01) |

(52) U.S. Cl.
CPC ............ *C07D 473/40* (2013.01); *A61K 31/522* (2013.01); *A61K 31/5377* (2013.01); *C07D 473/06* (2013.01); *C07D 473/18* (2013.01); *C07D 473/30* (2013.01)

(58) Field of Classification Search
CPC ........................ A61K 31/522; C07D 473/28
USPC .............. 544/253, 265; 514/258.1, 263.1
See application file for complete search history.

(56) References Cited

U.S. PATENT DOCUMENTS

| | | | |
|---|---|---|---|
| 3,573,309 A | 3/1971 | Bergmann et al. | |
| 6,825,349 B2 | 11/2004 | Kalla et al. | |
| 6,977,300 B2 | 12/2005 | Kalla et al. | |
| 7,317,017 B2 | 1/2008 | Kalla et al. | |
| 7,396,836 B2 | 7/2008 | Harada et al. | |
| 7,741,331 B2 | 6/2010 | Kalla et al. | |
| 7,851,478 B2 | 12/2010 | Kadowaki et al. | |
| 8,466,129 B2 | 6/2013 | Zeng et al. | |
| 8,796,290 B2 * | 8/2014 | Ramdas et al. | 514/263.34 |
| 8,859,566 B2 * | 10/2014 | Palle et al. | 514/263.1 |
| 8,940,751 B2 * | 1/2015 | Barawkar et al. | 514/263.1 |
| 2005/0119287 A1 | 6/2005 | Kalla et al. | |
| 2006/0281927 A1 | 12/2006 | Tomisawa et al. | |
| 2007/0037033 A1 | 2/2007 | Chiba et al. | |
| 2008/0194593 A1 | 8/2008 | Kalla et al. | |

FOREIGN PATENT DOCUMENTS

| | | |
|---|---|---|
| EP | 1 283 056 A1 | 2/2003 |
| GB | 683523 A | 12/1952 |
| GB | 1073040 A | 6/1967 |

(Continued)

OTHER PUBLICATIONS

Abo-Salem, O.M., et al., "Antinociceptive Effects of Novel $A_{2B}$ Adenosine Receptor Antagonists," *The Journal of Pharmacology and Experimental Therapeutics* 308(1):358-366, The American Society for Pharmacology and Experimental Therapeutics (2004).

(Continued)

*Primary Examiner* — Golam M M Shameem

(74) *Attorney, Agent, or Firm* — Sterne, Kessler, Goldstein & Fox P.L.L.C.

(57) ABSTRACT

The present invention discloses substituted fused pyrimidine compounds of formula (I), their tautomers, polymorphs, stereoisomers, solvates, pharmaceutically acceptable salts, or pharmaceutical compositions containing them and methods of treating conditions and diseases that are mediated by adenosine receptor (AR) activity; the compounds of the present invention are useful in the treatment, prevention or suppression of diseases and disorders that may be susceptible to improvement by antagonism of the adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

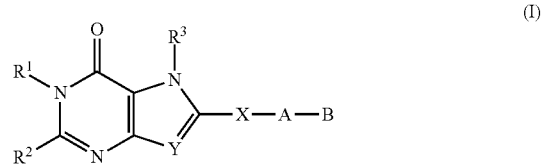

(I)

13 Claims, No Drawings

(56) References Cited

FOREIGN PATENT DOCUMENTS

| | | |
|---|---|---|
| WO | WO-91/19717 A1 | 12/1991 |
| WO | WO-00/10391 A1 | 3/2000 |
| WO | WO-00/13682 A2 | 3/2000 |
| WO | WO-00/73307 A2 | 12/2000 |
| WO | WO-01/02409 A1 | 1/2001 |
| WO | WO-01/25210 A2 | 4/2001 |
| WO | WO-01/58241 A2 | 8/2001 |
| WO | WO-01/92264 A1 | 12/2001 |
| WO | WO-02/055083 A1 | 7/2002 |
| WO | WO-02/085904 A1 | 10/2002 |
| WO | WO-03/000694 A1 | 1/2003 |
| WO | WO-03/002566 A1 | 1/2003 |
| WO | WO-03/006465 A1 | 1/2003 |
| WO | WO-03/022283 A1 | 3/2003 |
| WO | WO-03/035639 A1 | 5/2003 |
| WO | WO-03/042214 A2 | 5/2003 |
| WO | WO-03/053361 A2 | 7/2003 |
| WO | WO-03/063800 A2 | 8/2003 |
| WO | WO-03/082873 A1 | 10/2003 |
| WO | WO-2004/106337 A1 | 12/2004 |
| WO | WO-2005/021548 A2 | 3/2005 |
| WO | WO-2005/042534 A2 | 5/2005 |
| WO | WO-2005/044245 A1 | 5/2005 |
| WO | WO-2006/009698 A2 | 1/2006 |
| WO | WO-2006/015357 A2 | 2/2006 |
| WO | WO-2006/091896 A2 | 8/2006 |
| WO | WO-2006/132275 A1 | 12/2006 |
| WO | WO-2007/017096 A1 | 2/2007 |
| WO | WO-2007/038212 A1 | 4/2007 |
| WO | WO-2007/038284 A1 | 4/2007 |
| WO | WO-2007/109547 A2 | 9/2007 |
| WO | WO-2007/149277 A2 | 12/2007 |
| WO | WO-2008/002596 A2 | 1/2008 |
| WO | WO-2008/002902 A2 | 1/2008 |
| WO | WO-2008/121748 A2 | 10/2008 |
| WO | WO-2009/076352 A1 | 6/2009 |
| WO | WO-2009/111442 A1 | 9/2009 |
| WO | WO-2009/111449 A1 | 9/2009 |
| WO | WO-2009/156737 A1 | 12/2009 |

OTHER PUBLICATIONS

Auchampach, J.A., et al., "Comparison of Three Different $A_1$ Adenosine Receptor Antagonists on Infarct Size and Multiple Cycle Ischemic Preconditioning in Anesthetized Dogs," *Journal of Pharmacology and Experimental Therapeutics* 308(3): 846-856, The American Society for Pharmacology and Experimental Therapeutics (2004).

Bergmann, F., et al., "Influence of 8-substituents on the oxidation of hypoxanthine and 6-thioxopurine by bovine milk xanthine oxidase," *Biochimica et Biophysica Acta Enzymology* 480(1):39-46, Elsevier (1977).

Bergmann, F., and Rashi, M., "Electrophilic and Nucleophilic Substitution Reactions of 8-Pyridyl and 8-(1-Methylpyridinio)-purines," *Journal of the Chemical Society* 14:1831-1845, Royal Society of Chemistry (1969).

Chan, E.S.L., et al., "Adenosine $A_{2A}$ Receptors in Diffuse Dermal Fibrosis, Pathogenic Role in Human Dermal Fibroblasts and in a Murine Model of Scleroderma," *Arthritis & Rheumatism* 54(8):2632-2642, John Wiley & Sons (2006).

Chen, N., et al., "A Short, Facile Synthesis of 5-Substituted 3-Amino-1*H*-pyrrole-2-carboxylates," *Journal of Organic Chemistry* 65(8):2603-2605, American Chemical Society (2000).

Chen, Y., et al., "Functional effects of enhancing or silencing adenosine $A_{2b}$ receptors in cardiac fibroblasts," *American Journal of Physiology—Heart and Circulatory Physiology* 287: H2478-H2486, The American Physiological Society (2004).

Cook, A.H. and Thomas, G.H., "Studies in the Azole Series. Part XXX. New Syntheses of 2- and 8-Aminopurines," *Journal of the Chemical Society* 1888-1891, Royal Society of Chemistry (1950).

Cook, A. H., et al., "Studies in the Azole Series. Part XIV. A New Synthesis of Purines," *Journal of the Chemical Society* 1071-1074, Royal Society of Chemistry (1949).

Feoktistov, I., et al., "Adenosine $A_{2B}$ receptors: a novel therapeutic target in asthma?," *Trends in Pharmacological Sciences* 19(4):148-153, Elsevier Science Ltd. (1998).

Feoktistov, I., and Biaggioni, I., "Adenosine $A_{2B}$ Receptors," *Pharmacological Reviews* 49(4):381-402, The American Society for Pharmacology and Experimental Therapeutics (1997).

Feoktistov, I., et al., "Differential Expression of Adenosine Receptors in Human Endothelial Cells, Role of $A_{2B}$ Receptors in Angiogenic Factor Regulation," *Circulation Research* 90:531-538, American Heart Association (2002).

Fishman, P., and Bar-Yehuda, S., "Pharmacology and Therapeutic Applications of $A_3$ Receptor Subtype," *Current Topics in Medicinal Chemistry* 3:463-469, Bentham Science Publishers Ltd. (2003).

Forman, M.B., et al., "Sustained Reduction in Myocardial Reperfusion Injury with an Adenosine Receptor Antagonist: Possible Role of the Neutrophil Chemoattractant Response," *The Journal of Pharmacology and Experimental Therapeutics* 292(3):929-938, The American Society for Pharmacology and Experimental Therapeutics (2000).

Fozard, J.R., and Hannon, J.P., "Adenosine Receptor Ligands: Potential as Therapeutic Agents in Asthma and COPD," *Pulmonary Pharmacology & Therapeutics* 12 (2): 111-114, Academic Press (1999).

Fu, H., et al., "Regiospecific Solid-Phase Strategy to N7-Substituted Purines and Its Application to 8-Azapurines and [i]-Condensed Purines," *Journal of Combinatorial Chemistry* 9(5):804-810, American Chemical Society (2007).

Fuxe, K., et al., "Adenosine $A_{2A}$ and Dopamine $D_2$ Heteromeric Receptor Complexes and Their Function," *Journal of Molecular Neuroscience* 26:209-220, Humana Press Inc. (2005).

Gao, Y., and Phillis, J.W., "CGS 15943, An adenosine $A_2$ receptor antagonist, reduces cerebral ischemic injury in the Mongolian gerbil," *Life Sciences* 55(3):PL61-PL65, Elsevier Science Ltd. (1994).

Ge, Z.-D., et al., "CI-IB-MECA [2-Chloro-$N^6$-(3-iodobenzyl)adenosine-5'-$N$-methylcarboxamide] Reduces Ischemia/Reperfusion Injury in Mice by Activating the $A_3$ Adenosine Receptor," *The Journal of Pharmacology and Experimental Therapeutics* 319(3):1200-1210, The American Society for Pharmacology and Experimental Therapeutics (2006).

Gho, B.C.G., et al., "Myocardial Protection by Brief Ischemia in Noncardiac Tissue," *Circulation* 94:2193-2200, American Heart Association, Inc. (1996).

Gottlieb, S.S., et al., "BG9719 (CVT-124), an $A_1$ Adenosine Receptor Antagonist, Protects Against the Decline in Renal Function Observed With Diuretic Therapy," *Circulation* 105:1348-1353, American Heart Association (2002).

Headrick, J.P., and Peart, J., "$A_3$ adenosine receptor-mediated protection of the ischemic heart," *Vascular Pharmacology* 42 (5-6):271-279, Elsevier Inc. (2005).

Lauria, A., et al., "Docking of indolo- and pyrrolo-pyrimidines to DNA. New DNA-interactive polycycles from amino-indoles/pyrroles and BMMA," *ARKIVOC V*:263-271, ARKAT USA, Inc. (2004).

McNaught, A.D. and Wilkinson, A., "Cycloalkyl groups," *IUPAC Compendium of Chemical Terminology*, $2^{nd}$ Edition, http://www.iupac.org/goldbook/C01498.pdf (1997).

Nadeem, A., et al., "Adenosine $A_1$ receptor antagonist versus montelukast on airway reactivity and inflammation," *European Journal of Pharmacology* 551:116-124, Elsevier B.V. (2006).

Neiman, Z., "Reduction of Quaternary Pteridines and Purines by Sodium Borohydride," *Journal of the Chemical Society* 1:91-94, The Chemical Society (1970).

Obiefuna, P.C.M., et al., "A Novel $A_1$ Adenosine Receptor Antagonist, L-97-1 [3-[2-(4-Aminophenyl)-ethyl]-8-benzyl-7-{2-ethyl-(2-hydroxy-ethyl)-amino[-ethyl}-1-propyl-3,7-dihydro-purine-2,6-dione], Reduces Allergic Responses to House Dust Mite in an Allergic Rabbit Model of Asthma," *The Journal of Pharmacology and Experimental Therapeutics* 315(1):329-336, The American Society for Pharmacology and Experimental Therapeutics (2005).

Patané, E., et al., "Synthesis of 3-Arylpiperazinylalkylpyrrolo[3,2-*d*]pyrimidine-2,4-dione Derivatives as Novel, Potent, and Selective

(56) References Cited

OTHER PUBLICATIONS $\beta_1$-Adrenoceptor Ligands," *Journal of Medicinal Chemistry* 48(7):2420-2431, American Chemical Society (2005).

Patani, G.A., and E.J. Lavoie, "Bioisosterism: A Rational Approach in Drug Design," *Chemical Reviews* 96(8):3147-3176, American Chemical Society (1996).

Polosa, R., and Holgate, S.T., "Adenosine Receptors as Promising Therapeutic Targets for Drug Development in Chronic Airway Inflammation," *Current Drug Targets* 7(6):699-706, Bentham Science Publishers Ltd. (2006).

Richardson, P.J., et al., "Adenosine $A_{2A}$ receptor antagonists as new agents for the treatment of Parkinson's disease," *Trends in Pharmacological Sciences* 18(9):338-344, Elsevier Science Ltd. (1997).

Rollins, B.M., et al., "$A_{2B}$ Adenosine Receptors Regulate the Mucus Clearance Component of the Lung's Innate Defense System," *American Journal of Respiratory Cell and Molecular Biology* 39:190-197, The American Thoracic Society (2008).

Rüsing, D., et al., "The impact of adenosine and $A_{2B}$ receptors on glucose homoeostasis," *Journal of Pharmacy and Pharmacology* 58:1639-1645, Royal Pharmaceutical Society of Great Britain (2006).

Ryabukhin, S.V., et al., "Synthesis of Fused Imidazoles and Benzothiazoles from (Hetero)Aromatic ortho-Diamines or ortho-Aminothiophenol and Aldehydes Promoted by Chlorotrimethylsilane," *Synthesis* 21:3715-3726, Thieme Chemistry (2006).

Spicuzza, L., et al., "Research applications and implications of adenosine in diseased airways," *TRENDS in Pharmacological Sciences* 24(8):409-413, Elsevier Ltd. (2003).

Wilcox, C.S., et al., "Natriuretic and Diuretic Actions of a Highly Selective Adenosine $A_1$ Receptor Antagonist," *Journal of the American Society of Nephrology* 10:714-720, American Society of Nephrology (1999).

Wilson, C.N., "Adenosine receptors and asthma in humans," *British Journal of Pharmacology* 155:475-486, Macmillan Publishers Limited (2008).

Xu, K., el al., "Therapeutic potential of adenosine $A_{2A}$ receptor antagonists in Parkinson's disease," *Pharmacology & Therapeutics* 105(3):267-310, Elsevier Inc. (2005).

Zhong, H., et al., "Synergy between $A_{2B}$ Adenosine Receptors and Hypoxia in Activating Human Lung Fibroblasts," *American Journal of Respiratory Cell and Molecular Biology* 32:2-8, The American Thoracic Society (2005).

International Search Report mailed Oct. 18, 2010 for International Application No. PCT/IN2010/000145, European Patent Office, Rijswijk, Netherlands.

Written Opinion of the International Searching Authority mailed Oct. 18, 2010 for International Application No. PCT/IN2010/000145, European Patent Office, Rijswijk, Netherlands.

International Preliminary Report on Patentability mailed Sep. 13, 2011 for International Application No. PCT/IN2010/000145, International Bureau of WIPO, Geneva, Switzerland.

* cited by examiner

SUBSTITUTED FUSED PYRIMIDINE COMPOUNDS

FIELD OF THE INVENTION

The present invention relates to a series of novel substituted fused pyrimidine compounds, their tautomers, polymorphs, stereoisomers, prodrugs, solvates, pharmaceutically acceptable salts, pharmaceutical compositions containing them and methods of treating conditions and diseases that are mediated by adenosine receptor (AR) activity. These compounds are useful in the treatment, prevention or suppression of diseases and disorders that may be susceptible to improvement by antagonism of the adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, neurodegenerative disorders and/or autoimmune diseases.

BACKGROUND OF THE INVENTION

Adenosine is known to be an endogenous modulator of a number of physiological functions and these are mediated by the interaction with different membrane specific receptors which belong to the family of receptors coupled with G proteins. Adenosine exerts effects in cardiovascular, central nervous, respiratory systems, kidney, adipose and platelets. Recent advances in molecular biology coupled with several pharmacological studies have lead to identification of at least four subtypes of adenosine receptors, $A_1$, $A_{2B}$, $A_{2b}$ and $A_3$. The $A_1$ and $A_3$ receptors down-regulate cellular cAMP levels through their coupling to G protein, which inhibit adenylate cyclase. In contrast, $A_{2A}$ and $A_{2B}$ receptors couple to G protein that activate adenylate cyclase and increase intracellular levels of cAMP.

Advances in understanding the role of adenosine and its receptors in physiology and pathophysiology as well as new developments in medicinal chemistry of these receptors have identified potential therapeutic areas for drug development. With the combination of pharmacological data, using selective ligands and genetically modified mice, important progress has been made toward an understanding of the role of ARs in a variety of diseases, such as inflammatory conditions, sepsis, heart attack, ischemia-reperfusion injury, vascular injury, spinal cord injury, chronic obstructive pulmonary disease (COPD), asthma, diabetes, obesity, inflammatory bowel disease, retinopathy, and Parkinson's Disease (PD).

In the central nervous system, $A_{2a}$ antagonists can have antidepressant properties and stimulate cognitive functions. There is fairly convincing prospective epidemiological evidence of a protective effect of caffeine against Parkinson's disease. Moreover, data has shown that $A_{2a}$ receptors density is very high in the basal ganglia, known to be important in the control of movement. Hence, selective $A_{2a}$ antagonists can improve motor impairment due to neurodegenerative diseases such as Parkinson's disease (Trends Pharmacol. Sci. 1997, 18, 338-344), senile dementia as in Alzheimer's disease, psychoses, stroke and in the treatment of cerebral ischaemia (Life Sci. 1994, 55, 61-65). $A_{2a}$ antagonists may also be employed for the treatment or management of attention related disorders such as attention deficit disorder and attention deficit hyperactivity disorder, extra pyramidal syndrome, e.g., dystonia, akathisia, pseudoparkinsonism and tardive dyskinesia, and disorders of abnormal movement such as restless leg syndrome and periodic limb movement in sleep. Several of these indications have been disclosed in patent applications (eg. WO 02/055083, WO 05/044245 and WO 06/132275). Adenosine $A_{2a}$ antagonists are also useful agents for the treatment of amyotrophic lateral sclerosis, cirrhosis, and fibrosis and fatty liver (US2007037033, WO 01/058241). $A_{2a}$ receptor antagonists are also useful for the mitigation of addictive behavior (WO 06/009698) and for the treatment and prevention of dermal fibrosis in diseases such as scleroderma (Arthritis & Rheumatism, 54(8), 2632-2642, 2006).

PD is a progressive, incurable disorder with no definite preventive treatment, although drugs are available to alleviate the symptoms and/or slow down the progress of the disease. Among the various strategies, A2A AR blockers are considered a potential approach to treatment of the disease.

Within the brain A2A ARs are richly expressed in the striatum, nucleus accumbens, and olfactory tubercle. A coexpression of A2A with D2 dopamine receptors has been reported in the GABAergic striatopallidal neurons where adenosine and dopamine agonists exert antagonistic effects in the regulation of locomotor activity. Activation of A2A ARs in striatopallidal neurons decreases the affinity of D2 receptors for dopamine, antagonizing the effects of D2 receptors. The negative interaction between A2A and D2 receptors is at the basis of the use of A2A antagonists as a novel therapeutic approach in the treatment of PD. (Pharmacol. Ther. 2005, 105, 267). The recent discovery that the A2A can form functional heteromeric receptor complexes with other Gprotein-coupled receptors such as D2 and the mGlu5 receptors has also suggested new opportunities for the potential of A2A antagonists in PD. (J. Mol. Neurosci. 2005, 26, 209).

A2A receptors may be beneficial for the treatment or prevention of disorders such as a movement disorder, for example, Parkinson's disease or progressive supernuclear palsy, Restless leg syndrome, nocturnal myoclonus, cerebral ischaemia, Huntington's disease, multiple system atrophy, corticobasal degeneration, Wilsons disease or other disorders of basal ganglia which results in dyskinesias. See for example WO200013682, WO200012409, WO2009156737, WO200911442, WO2008121748, WO2001092264, WO2007038284, WO2008002596, WO2009111449, WO2009111442, WO2008121748, WO2009156737, WO2003022283, WO2005044245, WO2007038212

Adenosine signaling is known to serve apoptotic, angiogenic and pro-inflammatory functions and might be relevant to the pathogenesis of asthma and chronic obstructive pulmonary disease (Trends in Pharmacological Sciences, Vol. 24, No. 8, August 2003). Extracellular adenosine acts as a local modulator with a generally cytoprotective function in the body. Its effects on tissue protection and repair fall into four categories: increasing the ratio of oxygen supply to demand; protecting against ischaemic damage by cell conditioning; triggering anti-inflammatory responses; and the promotion of angiogenesis. The $A_{2B}$ adenosine receptor subtype (see Feoktistov, I., Biaggioni, I. Pharmacol. Rev. 1997, 49, 381-402) has been identified in a variety of human and murine tissues and is involved in the regulation of vascular tone, smooth muscle growth, angiogenesis, hepatic glucose production, bowel movement, intestinal secretion, and mast cell degranulation. $A_{2B}$ receptors have been implicated in mast cell activation and asthma, control of vascular tone, cardiac myocyte contractility, cell growth and gene expression, vasodilation, regulation of cell growth, intestinal function, and modulation of neurosecretion (Pharmacological Reviews Vol. 49, No. 4).

$A_{2B}$ receptors modulate mast cell function. Adenosine activates adenylate cyclase and protein kinase C, and potentiates stimulated mediator release in mouse bone marrow derived mast cells. (*TiPS*—April 1998 (Vol. 19)). Activation of $A_{2B}$ receptors in HMC-1 augments IL-8 release and potentiates PMA-induced secretion of IL-8. Thus, adenosine would contribute to the asthmatic response by acting on the mast cell to enhance the release of proinflammatory mediators. (*Pulmonary Pharmacology & Therapeutics* 1999, 12, 111-114). In COPD, transformation of pulmonary fibroblasts into myofibroblasts is considered a major mechanism. Activation of the $A_{2B}$ AR is involved in this process. Selective $A_{2B}$ antagonists are expected to have beneficial effect on pulmonary fibrosis (*Curr. Drug Targets*, 2006, 7, 699-706; *Am. J. Resper. Cell. Mol. Biol.*, 2005, 32, 228). $A_{2B}$ antagonists can be used as wound healing agents. Activation of the $A_{2B}$ AR promotes angiogenesis by increasing the release of angiogenic factors and $A_{2B}$ antagonists are useful to block angiogenesis (*Circ. Res.*, 2002, 90, 531-538). $A_{2B}$ AR may be involved in the inhibition cardiac fibroblast (CF) proliferation (*Am. J. Physiol. Heart Circ. Physiol.*, 2004, 287, H2478-H2486). Adenosine stimulates Cl— secretion in the intestinal epithelia pointing towards a possible treatment for cystic fibrosis patients with CFTR mutation (*Am. J. Respir. Cell Mol. Biol*, 2008, 39, 190-197). High affinity $A_{2B}$ antagonists are effective in hot plate model suggestive of the role of $A_{2B}$ in nociception and can be used as potential analgesic agents (*The J. of Pharmacol. and Exp. Ther.*, 2004, 308, 358-366). $A_{2B}$ receptor is involved in release of IL-6. Increasing evidence suggests that IL-6 plays a role in Alzheimer's disease in the context of inflammatory process associated with disease. Hence $A_{2B}$ receptor antagonist might be useful for Alzheimer's disease.

The $A_{2B}$ ARs are involved in the stimulation of nitric oxide production during Na$^+$-linked glucose or glutamine absorption. They are involved in glucose production in hepatocytes upon agonist stimulation. $A_{2B}$-receptor antagonists showed an anti-diabetic potential mainly by increasing plasma insulin levels under conditions when the adenosine tonus was elevated in-vivo and increased insulin release in-vitro (J. Pharm. Pharmacol. 2006 December; 58(12):1639-45). Thus $A_{2B}$ antagonists may serve as a novel target for the treatment of this metabolic disease.

It has been demonstrated that adenosine activation of the $A_{2B}$ adenosine receptor increase cAMP accumulation, cell proliferation and VEGF expression in human retinal endothelial cells. Activation of $A_{2B}$AdoR increased vascular endothelial cell growth factor mRNA and protein expression in human retinal endothelial cells. Adenosine also has a synergistic effect with VEGF on retinal endothelial cell proliferation and capillary morphogenesis in vitro. Such activity is necessary in healing wounds, but the hyperproliferation of endothelial cells promotes diabetic retinopathy. Also, an undesirable increase in blood vessels occurs in neoplasia. Accordingly, inhibition of binding of adenosine to $A_{2B}$ receptors in the endothelium will alleviate or prevent hypervasculation, thus preventing retinopathy and inhibiting tumor formation.

In view of the physiological effects mediated by adenosine receptor, several $A_{2B}$ receptor antagonists have been recently disclosed for the treatment or prevention of asthma, bronchoconstriction, allergic diseases, hypertension, atherosclerosis, reperfusion injury, myocardial ischemia, retinopathy, inflammation, gastrointestinal tract disorders, cell proliferation diseases and/or diabetes mellitus. See for example WO2008002902, WO2007149277, WO2007017096, WO2007109547, WO2006091896, WO2006015357, WO2005042534, WO2005021548, WO2004106337, WO2003000694, WO2003082873, WO2003006465, WO2003053361, WO2003002566, WO2003063800, WO2003042214, WO2003035639, EP1283056, WO200073307, WO2000125210, WO2000073307, US20050119287, US20060281927.

It has now been found that compounds of the present invention are potent antagonists of the $A_{2B}$ adenosine receptor and can therefore be used in the treatment of the diseases mentioned herein above.

Under normal physiological conditions, $A_1$ ARs are quiescent; however, $A_1$ ARs are upregulated in conditions of stress, such as ischaemia, and in conditions of inflammation, typified by the inflammatory airway involvement in human asthmatics. $A_1$ ARs are upregulated in airway epithelium and bronchial smooth muscle in human asthmatics. $A_1$ ARs have been described on a number of different human cell types that are important in the pathophysiology of asthma, including APCs, human airway epithelial and bronchial smooth muscle cells, lymphocytes, mast cells, neutrophils, monocytes, macrophages, fibroblasts and endothelial cells. Activation of $A_1$ ARs on these different cell types induces the release of mediators and cytokines that lead to airway hyperreactivity, inflammation and airway remodelling. Activation of $A_1$ ARs on human asthmatic bronchial tissue produces bronchoconstriction. On human airway epithelial cells, activation of $A_1$ ARs causes an increase in expression of the MUC 2 gene responsible for mucus hypersecretion. Moreover, activation of $A_1$ ARs on a number of different human cells produces pro-inflammatory effects. Taken together, these effects of $A_1$ ARs in humans suggest that the $A_1$ AR antagonists could play potential therapeutic role in inflammatory diseases (C N Wilson, British J. of Pharm., 2008, 155, 475-86 and references cited therein). $A_1$ AR antagonists have been shown to have efficacy in rodent models of asthma and inflammation ((*J. Pharmacol. Exp. Ther.* 315, 329-336, 2005; *Eur. J. Pharmacol.*, 551, 116-124, 2006).

$A_1$ antagonists have also been shown to have therapeutic potential in diseases such as hypertension, congestive heart failure where underlying mechanism is diuresis. There are several compounds in development for these indications (*J. Am. Soc. Nephrol.* 10, 714-720, 1999; *Circulation*, 105, 1348-1353, 2002; *J. Pharmacol. Exp. Ther.* 308, 846-856, 2004).

$A_1$ AR antagonists are reported to reduce infarct size. It has been suggested that the ability of $A_1$ AR antagonists to reduce the infarct size is also mediated by antagonism at $A_{2B}$ AR (*Circulation*, 1996, 9, 94; *J. Pharmacol. Exp. Ther.*, 2000, 292, 3, 929-938).

Activation of $A_3$ ARs induces the release of preformed mediators from basophils and produces bronchoconstriction, eosinophil migration into airways and mucus hypersecretion in animals, $A_3$ AR antagonists have been recommended for development as anti-asthma drugs (Fishman and Bar-Yehuda, 2003; Nadeem and Mustafa, 2006). $A_3$ AR antagonists have also been shown to play therapeutic role in various diseases including cardio-protection (*Vasc. Pharmacol.*, 2005, 42, 271; *J. Pharm. Exp. Ther.*, 2006, 319, 1200) and cancer (WO200010391).

Since several ARs have been implicated in asthma/COPD diseases pathophysiology, a pan AR antagonist may have therapeutic advantage.

It has now been found that some of the compounds of the present invention are non-selective antagonists of ARs and can therefore be used in the treatment of above mentioned diseases.

SUMMARY OF THE INVENTION

The present invention provides compounds of formula (I),

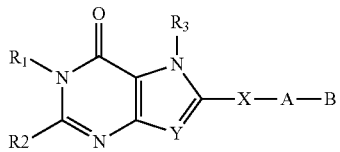

or its tautomers, polymorphs, stereoisomers, prodrugs, solvate or a pharmaceutically acceptable salts thereof, wherein
Y is selected from N or CR; R is selected from H, hydroxy, alkoxy, alkyl, or aryl;
$R^1$ is selected from a group consisting of alkyl, alkenyl and alkynyl, wherein one or more methylene groups are optionally replaced by hetero atoms or group selected from —O—, —S(O)p-, —N($R^a$)—, or —C(O) provided that the heteroatom is not adjacent to N in the ring; p is selected from 0, 1 or 2;
wherein alkyl, alkenyl and alkynyl are unsubstituted or substituted independently with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino, nitro, —S(O)$_2$NR$^a$R$^a$, —NR$^a$S(O)$_2$R$^a$, or —S(O)$_p$R$^a$; $R^2$ is selected from a group consisting of hydrogen, halogen, cyano, nitro, carboxy, acyl, aminocarbonyl, alkyl, alkenyl, alkynyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl and heteroaryloxy;
wherein alkyl, alkenyl, alkynyl, alkoxy, carboxyalkyl, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl, heteroaryloxy and $R^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;
wherein each substituent is unsubstituted or substituted with 1, 2, or 3 substituents independently selected from alkyl, carboxy, carboxyalkyl, aminocarbonyl, hydroxy, alkoxy, halogen, haloalkyl, haloalkoxy, amino, substituted amino, cyano or —S(O)$_p$R$^d$;
$R^3$ is selected from a group consisting of hydrogen, alkyl, alkenyl, alkynyl, alkoxyalkyl, cycloalkyl, cycloalkylalkyl, aryl, arylalkyl, heteroaryl and heteroarylalkyl;
wherein alkyl, alkenyl, alkynyl, alkoxyalkyl, cycloalkyl, cycloalkylalkyl, aryl, arylalkyl, heteroaryl, and heteroarylalkyl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^c$R$^c$, —NR$^c$S(O)$_2$R$^c$ or —S(O)$_p$R$^d$;
wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —S(O)$_p$R$^d$;
X is either an optionally substituted arylene or an optionally substituted heteroarylene;
A is selected from a bond, (C$_1$-C$_6$)alkylene, (C$_2$-C$_6$)alkenylene or (C$_2$-C$_6$)alkynylene group, wherein 1 to 4 methylene groups are optionally replaced by groups independently selected from O, —S(O)$_p$—, —N(R$^b$)—, or —C(O)—;
wherein alkylene, alkenylene, and alkynylene are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^c$R$^c$, —NR$^c$S(O)$_2$R$^c$ or —S(O)$_p$R$^d$;
wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;
B is selected from hydrogen, heterocyclyl, cycloalkyl, aryl or heteroaryl;
wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —S(O)$_2$NR$^b$R$^b$, —NR$^b$S(O)$_2$R$^b$ or —S(O)$_p$R$^d$;
wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

$R^a$ is independently selected from the group consisting of hydrogen and alkyl;

$R^b$ is independently selected from the group consisting of hydrogen, alkyl, acyl, carboxyalkyl, carbonylamino, cycloalkyl, cycloalkylalkyl, aryl, arylalkyl, heteroaryl, heteroarylalkyl, heterocyclyl and heterocyclylalkyl;

$R^c$ is selected from hydrogen, alkyl, aryl, heteroaryl or heterocyclyl;

$R^d$ is selected from alkyl, cycloalkyl, aryl, heterocyclyl or heteroaryl; and p is 0, 1 or 2.

The present invention also provides methods of treating conditions and diseases that are mediated by adenosine receptor activity.

DETAILED DESCRIPTION OF THE INVENTION

Definitions

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, iso-propyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkyl" or "substituted alkylene" refers to: 1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where $R^b$ is hydrogen, alkyl, aryl, heteroaryl or heterocyclyl. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where $R^c$ is alkyl, aryl, or heteroaryl and p is 0, 1 or 2;

or 2) an alkyl group or alkylene group as defined above that is interrupted by 1, 2, 3, 4, 5, 6, 7, 8, 9 or 10 atoms independently selected from oxygen, sulfur and NR$^d$, where $R^d$ is selected from hydrogen, alkyl, cycloalkyl, cycloalkenyl, aryl, heteroaryl and heterocyclyl, carbonylalkyl, carboxyester, carboxyamide and sulfonyl. All substituents may be optionally further substituted by alkyl, alkoxy, halogen, CF$_3$, amino, substituted amino, cyano, or —S(O)$_p$R$^c$, in which $R^c$ is alkyl, aryl, or heteroaryl and p is 0, 1, or 2;

or 3) an alkyl or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl(—CH═CH$_2$), 1-propylene or allyl (—CH$_2$CH═CH$_2$), isopropylene (—C(CH$_3$)═CH$_2$), bicyclo[2.2.1]heptene, and the like.

The term "alkenylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each $R^a$ is independently selected from the group consisting of hydrogen, alkyl, cycloalkyl, cycloallylalkyl, aryl, arylalkyl, heteroaryl heteroarylalkyl, heterocyclyl and heterocyclylalkyl; heterocyclyloxywhere $R^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where $R^c$ is alkyl, aryl, or heteroaryl and p is 0, 1 or 2.

The term "alkynyl" refers to a monoradical of an unsaturated hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —CH$_2$C≡CH), homopropargyl (or but-1-yn-4-yl, —CH$_2$CH$_2$C≡CH) and the like.

The term "alkynylene" refers to a diradical of a branched or unbranched unsaturated hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —SO₃H, aryl, aryloxy, heteroaryl, aminocarbonylamino, heteroaryloxy, heterocyclyl, heterocyclyloxy, hydroxyamino, alkoxyamino, nitro, —S(O)₂NR$^a$R$^a$, —NR$^a$S(O)₂R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF₃, amino, substituted amino, cyano, and —S(O)$_p$R$^c$ where R$^c$ is alkyl, aryl, or heteroaryl and p is 0, 1 or 2.

The term "cycloalkyl" refers to carbocyclic groups of from 3 to 20 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo[2.2.1]heptane, 1,3,3-trimethylbicyclo[2.2.2.1]hept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —S(O)$_p$R$^b$, where R is hydrogen, hydroxyl, alkoxy, alkyl and cyclocalkyl, heterocyclyloxywhere R$^b$ is alkyl, aryl, heteroaryl or heterocyclyl and p is 0, 1 or 2. Unless otherwise constrained by the definition, all substituents may optionally be further substituted by 1, 2, or 3 substituents selected from alkyl, carboxy, carboxyalkyl, aminocarbonyl, hydroxy, alkoxy, halogen, CF₃, amino, substituted amino, cyano, and —S(O)$_p$R$^c$, where R$^c$ is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'''—O—, where R''' is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents selected from alkyl, carboxy, carboxyalkyl, aminocarbonyl, hydroxy, alkoxy, halogen, CF₃, amino, substituted amino, cyano, and —S(O)$_p$R$^c$, where R$^c$ is alkyl, aryl, or heteroaryl and p is 0, 1 or 2.

The term "acylamino" refers to the group —NR"C(O)R" where each R" is independently hydrogen, alkyl, aryl, heteroaryl, or heterocyclyl. Unless otherwise constrained by the definition, all substituents may optionally be further substituted by 1-3 substituents selected from alkyl, carboxy, carboxyalkyl, aminocarbonyl, hydroxy, alkoxy, halogen, CF₃, amino, substituted amino, cyano, and —S(O)$_p$R$^c$, where R$^c$ is alkyl, aryl, or heteroaryl and p is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, CF₃, amino, substituted amino, cyano, or —S(O)$_p$R$^c$, where R$^c$ is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to (C$_{1-6}$)alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO$_3$H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; where R$^b$ is hydrogen, alkyl, aryl, heterocyclyl or heteroaryl and p is 0, 1 or 2. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, CF$_3$, amino, substituted amino, cyano, and —S(O)$_p$R$^c$ where R$^c$ is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents selected from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)OR$^d$ where R$^d$ is alkyl, cycloalkyl, where alkyl, cycloalkyl are as defined herein, and may be optionally further substituted by alkyl, halogen, CF$_3$, amino, substituted amino, cyano, or —S(O)$_p$R$^c$, in which R$^c$ is alkyl, aryl, or heteroaryl and p is 0, 1 or 2.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like.

The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)$_n$R$^c$, where R$^c$ is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —S(O)$_p$R$^b$, where R$^b$ is hydrogen, alkyl, aryl, heterocyclyl or heteroaryl and p is 0, 1 or 2. Unless otherwise constrained by the definition, all substituents may optionally be further substituted by 1-3 substituents selected from alkyl, carboxy, carboxyalkyl, aminocarbonyl, hydroxy, alkoxy, halogen, CF$_3$, amino, substituted amino, cyano, and —S(O)R$^c$, where R$^c$ is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" refers to a group —S(O)$_2$R.

The term "substituted sulfone" refers to a group —S(O)$_2$R, in which R is alkyl, aryl, or heteroaryl.

The compounds of the present invention may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

The present invention provides compounds of formula I, or its tautomers, polymorphs, stereoisomers, prodrugs, solvate or a pharmaceutically acceptable salts thereof, pharmaceutical compositions containing them and methods of treating conditions and diseases that are mediated by adenosine receptor activity.

In an embodiment of the present invention, it provides a compound of formula I

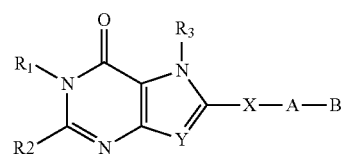

I or its tautomers, polymorphs, stereoisomers, prodrugs, solvate or a pharmaceutically acceptable salts thereof, wherein Y is selected from N or CR; R is selected from H, hydroxy, alkoxy, alkyl, or aryl;

$R^1$ is selected from a group consisting of alkyl, alkenyl and alkynyl, wherein one or more methylene groups are optionally replaced by hetero atoms or group selected from —O—, —S(O)$_p$—, —N(R$^a$)—, or —C(O) provided that the heteroatom is not adjacent to N in the ring; p is selected from 0, 1 or 2;

wherein alkyl, alkenyl and alkynyl are unsubstituted or substituted independently with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino, nitro, —S(O)$_2$NR$^a$R$^a$, —NR$^a$S(O)$_2$R$^a$, or —S(O)$_p$R$^a$;

$R^2$ is selected from a group consisting of hydrogen, halogen, cyano, nitro, carboxy, acyl, aminocarbonyl, alkyl, alkenyl, alkynyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl and heteroaryloxy;

wherein alkyl, alkenyl, alkynyl, alkoxy, carboxyalkyl, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl, heteroaryloxy and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, haloalkoxy, amino, substituted amino, cyano or —S(O)$_p$R$^d$;

$R^3$ is selected from a group consisting of hydrogen, alkyl, alkenyl, alkynyl, alkoxyalkyl, cycloalkyl, cycloalkylalkyl, aryl, arylalkyl, heteroaryl and heteroarylalkyl;

wherein alkyl, alkenyl, alkynyl, alkoxyalkyl, cycloalkyl, cycloalkylalkyl, aryl, arylalkyl, heteroaryl, and heteroarylalkyl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxyd, alkoxy, halogen, haloalkyl, haloalkoxy, amino, substituted amino, cyano or —S(O)$_p$R$^d$;

X is either an optionally substituted arylene or an optionally substituted heteroarylene;

A is selected from a bond, (C$_1$-C$_6$)alkylene, (C$_2$-C$_6$)alkenylene or (C$_2$-C$_6$)alkynylene group, wherein 1 to 4 methylene groups are optionally replaced by groups independently selected from O, —S(O)$_p$—, —N(R$^b$)—, or —C(O)—;

wherein alkylene, alkenylene, and alkynylene are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

B is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

$R^a$ is independently selected from the group consisting of hydrogen and alkyl;

$R^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

$R^c$ is selected from hydrogen, alkyl, aryl, heteroaryl or heterocyclyl;

$R^d$ is selected from alkyl, cycloalkyl, aryl, heterocyclyl or heteroaryl; and p is 0, 1 or 2.

According to another embodiment, the present disclosure relates to compounds of formula (I) wherein, Y is CR; R is selected from H, hydroxy, alkoxy, alkyl, or aryl;

R$^1$ is selected from a group consisting of alkyl, alkenyl and alkynyl, wherein alkyl, alkenyl and alkynyl are unsubstituted or substituted independently with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, or carboxyalkyl;

R$^2$ is selected from a group consisting of hydrogen, halogen, cyano, nitro, carboxy, acyl, aminocarbonyl, alkyl, alkenyl, alkynyl, hydroxyalkyl, haloalkyl, haloalkyloxy, alkoxy, and —NR$^b$R$^b$;
  wherein alkyl, alkenyl, alkynyl, alkoxy and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl or cycloalkenyl;

R$^3$ is selected from a group consisting of hydrogen, alkyl, alkenyl, alkynyl, cycloalkyl, cycloalkylalkyl, aryl, arylalkyl, heteroaryl and heteroarylalkyl;

X is either an optionally substituted arylene or an optionally substituted heteroarylene;

A is selected from a bond, (C$_1$-C$_6$)alkylene, (C$_2$-C$_6$)alkenylene or (C$_2$-C$_6$)alkynylene group, wherein 1 to 4 methylene groups are optionally replaced by groups independently selected from O, —S(O)$_p$—, —N(R$^b$)—, or —C(O)—;

B is selected from hydrogen, heterocyclyl, cycloalkyl, aryl or heteroaryl;
  wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, S(O)$_2$NR$^b$R$^b$, —NR$^b$S(O)$_2$R$^b$ or —S(O)$_p$R$^d$;
    wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

R$^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

R$^d$ is selected from alkyl, cycloalkyl, aryl, heterocyclyl or heteroaryl; and p is 0, 1 or 2.

According to an embodiment, the present disclosure relates to compounds of formula (I) wherein, Y is N or CR; R is selected from H, hydroxy, alkoxy, alkyl, or aryl;
  R$^1$ is selected from a group consisting of alkyl, alkenyl and alkynyl;
  R$^2$ is selected from a group consisting of hydrogen, halogen, cyano, nitro, carboxy, acyl, alkyl, alkenyl, alkynyl, alkoxy, —NR$^b$R$^b$, cycloalkyl, cycloalkyoxy, aryl, aryloxy, heterocyclyl, heterocyclyloxy, heteroaryl and heteroaryloxy;
    wherein alkyl, alkenyl, alkynyl, alkoxy, cycloalkyl, cycloalkyoxy, aryl, aryloxy, heterocyclyl, heterocyclyloxy, heteroaryl, heteroaryloxy and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl or cycloalkenyl;

R$^3$ is selected from a group consisting of hydrogen, alkyl, alkenyl, alkynyl, alkoxyalkyl, cycloalkyl, cycloalkylalkyl, aryl, arylalkyl, heteroaryl and heteroarylalkyl;

X is an optionally substituted phenyl;

A is selected from a bond, (C$_1$-C$_6$)alkylene, (C$_2$-C$_6$)alkenylene or (C$_2$-C$_6$)alkynylene group, wherein 1 to 4 methylene groups are optionally replaced by groups independently selected from O, —S(O)$_p$—, —N(R$^b$)—, or —C(O)—;

B is selected from hydrogen, heterocyclyl, cycloalkyl, aryl or heteroaryl;
  wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, S(O)$_2$NR$^b$R$^b$, —NR$^b$S(O)$_2$R$^b$ or —S(O)$_p$R$^d$;
    wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

R$^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

R$^d$ is selected from alkyl, cycloalkyl, aryl, heterocyclyl or heteroaryl; and p is 0, 1 or 2.

According to an embodiment, the present disclosure relates to compounds of formula (I) wherein Y is selected from N or CR; R is selected from H, hydroxy, alkoxy, alkyl, or aryl;
  R1 is selected from a group consisting of alkyl, alkenyl and alkynyl;
    wherein alkyl, alkenyl and alkynyl are unsubstituted or substituted independently with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino or nitro;

R² is selected from a group consisting of hydrogen, halogen, cyano, nitro, carboxy, acyl, aminocarbonyl, alkyl, alkenyl, alkynyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, aryl, arylalkyl, aryloxy, heterocyclyl, heterocyclyloxy, heteroaryl and heteroaryloxy;

wherein alkyl, alkenyl, alkynyl, alkoxy, carboxyalkyl, cycloalkyl, cycloalkylalkyl, cycloalkyloxy, aryl, arylalkyl, aryloxy, heterocyclyl, heterocyclyloxy, heteroaryl and heteroaryloxy and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, aryl, aryloxy, heterocyclyl, heterocyclyloxy, heteroaryl, heteroaryloxy, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, haloalkoxy, amino, substituted amino, cyano or —S(O)$_p$R$^d$;

R³ is selected from a group consisting of hydrogen, alkyl, alkenyl and alkynyl;

wherein alkyl, alkenyl and alkynyl are unsubstituted or substituted independently with alkyl, alkenyl, alkynyl, alkoxy, cycloalkyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino or nitro;

X is an optionally substituted heteroarylene;

A is selected from a bond, (C$_1$-C$_6$)alkylene, (C$_2$-C$_6$)alkenylene or (C$_2$-C$_6$)alkynylene group, wherein 1 to 4 methylene groups are optionally replaced by groups independently selected from O, —S(O)$_p$—, —N(R$^b$)—, or —C(O)—;

wherein alkylene, alkenylene, and alkynylene are unsubstituted or substituted independently with alkyl, alkenyl, alkynyl, alkoxy, cycloalkyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino or nitro;

B is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

R$^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

Rc is selected from hydrogen, alkyl, aryl, heteroaryl or heterocyclyl;

R$^d$ is selected from alkyl, cycloalkyl, aryl, heterocyclyl or heteroaryl; and p is 0, 1 or 2.

According to another embodiment, the present disclosure relates to compounds of formula (I) wherein X is selected from

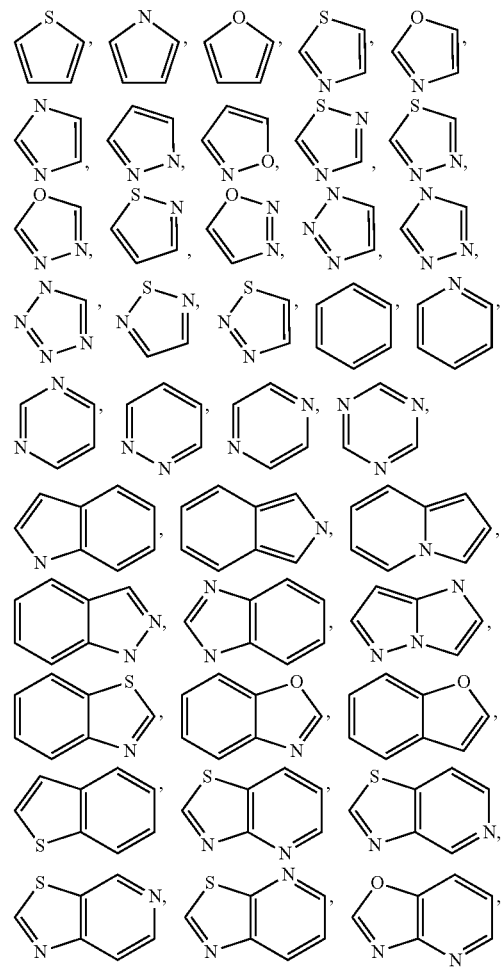

-continued
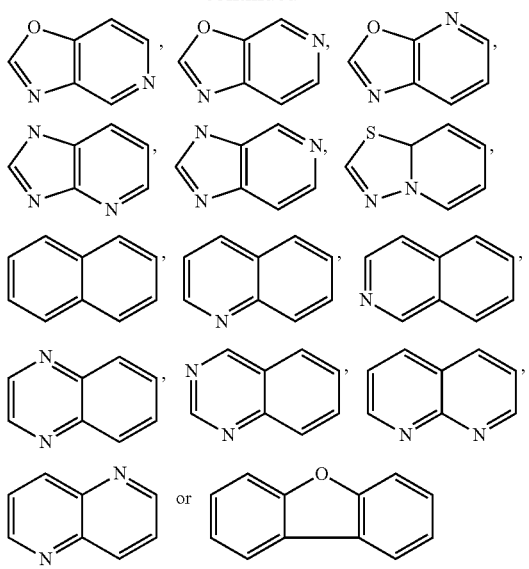
According to an embodiment, the present disclosure relates to compounds of formula (I) wherein B is selected from
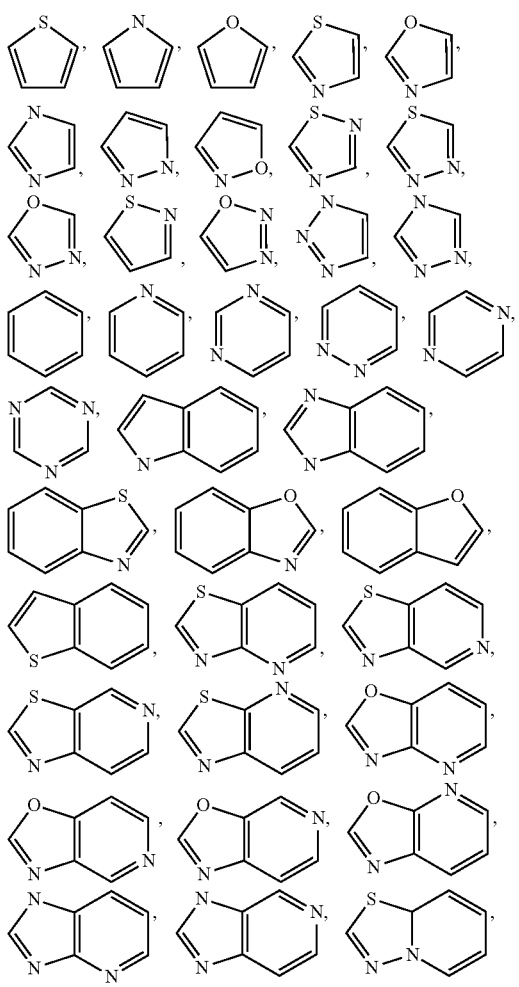
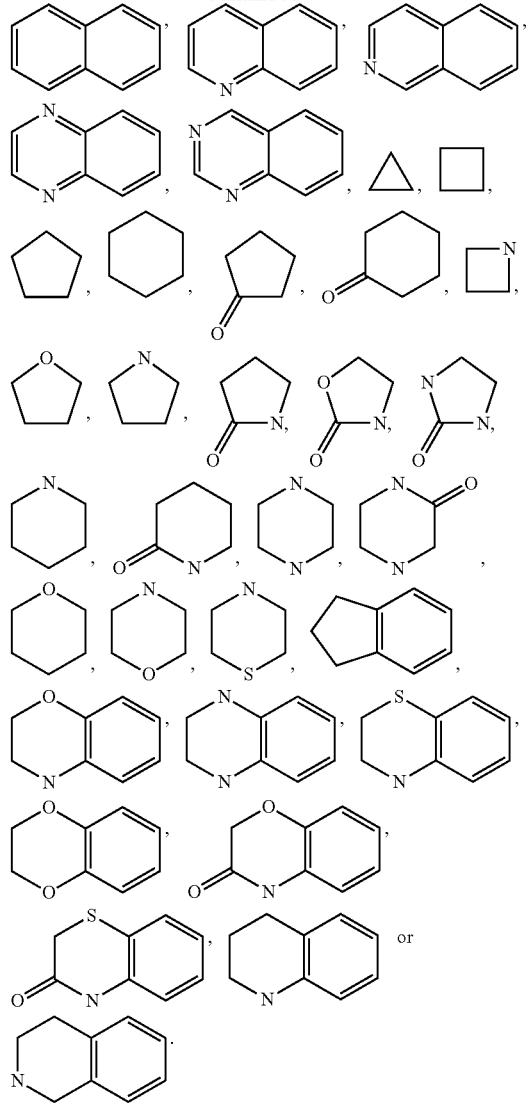
According to an embodiment, the present disclosure relates to compounds of formula (I) wherein A is selected from
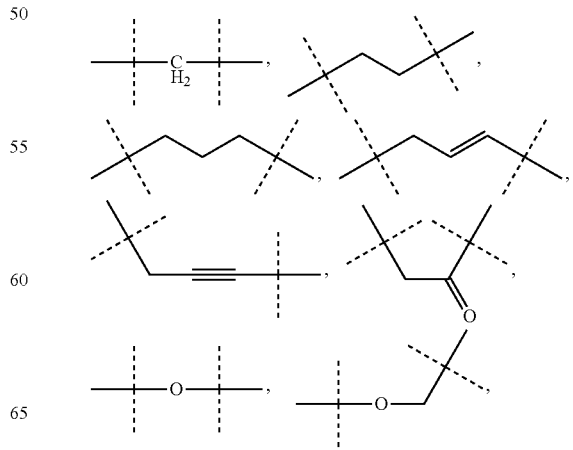

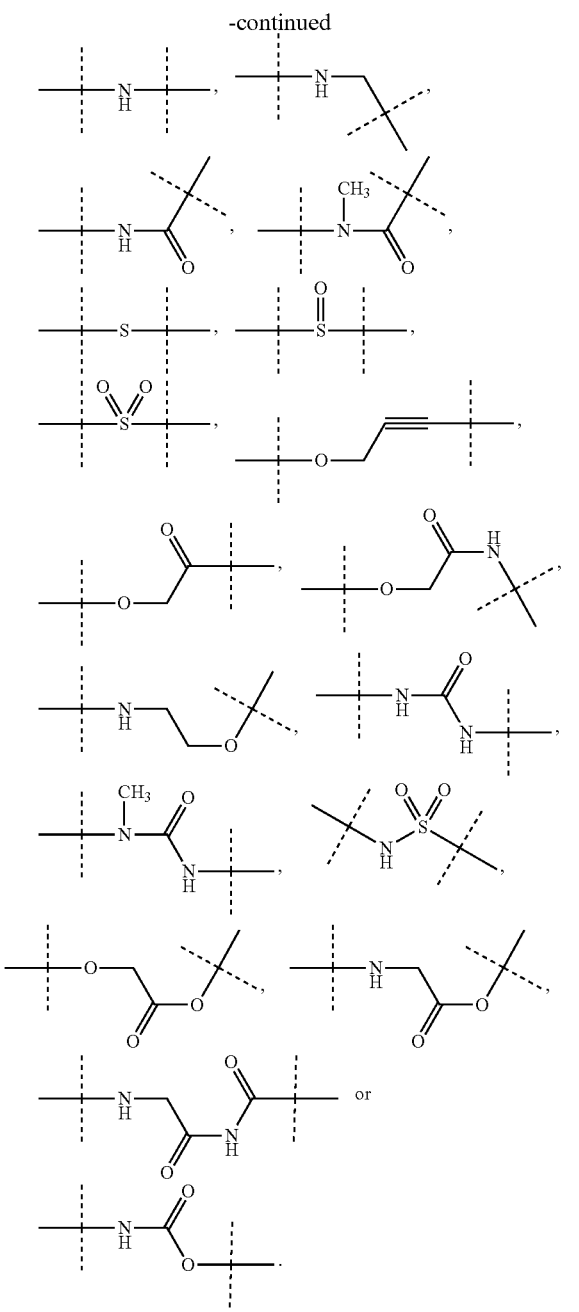

According to an embodiment, the present disclosure relates to compounds of formula (I) wherein Y is selected from N or CR; R is selected from H, hydroxy, alkoxy, alkyl, or aryl;

$R^1$ is alkyl wherein alkyl is unsubstituted or substituted independently with alkoxy, acyl, acylamino, acyloxy, cyano, halogen, hydroxy, carboxy, carboxyalkyl or nitro;

$R^2$ is selected from a group consisting of hydrogen, halogen, cyano, nitro, carboxy, acyl, aminocarbonyl, alkyl, hydroxyalkyl, carboxyalkyl, alkoxy, —$NR^bR^b$, cycloalkyl, aryl, arylalkyl, aryloxy, heterocyclyl and heteroaryl;

wherein alkyl, alkoxy, cycloalkyl, aryl, arylalkyl, heteroaryl, heterocyclyl and $R^b$ are unsubstituted or substituted independently with alkyl, alkoxy, acyl, acyloxy, nitro, amino, hydroxyamino, alkoxyamino, aminocarbonylamino, cyano, halogen, hydroxy, hydroxyalkyl, carboxy, alkylcarboxy, carboxyalkyl, —$SO_3H$, aminocarbonyl, cycloalkyl, cycloalkyloxy, aryl, aryloxy, heterocyclyl, heterocyclyloxy, heteroaryl or heteroaryloxy;

$R^3$ is selected from a group consisting of hydrogen, alkyl, aryl and arylalkyl;
wherein alkyl, aryl and arylalkyl are unsubstituted or substituted independently with alkyl, acyl, acylamino, acyloxy, amino, cyano, halogen, hydroxy, carboxy, alkylcarboxy or carboxyalkyl;

X is either an optionally substituted arylene or an optionally substituted heteroarylene;

A is selected from a bond, ($C_1$-$C_6$)alkylene, ($C_2$-$C_6$)alkenylene or ($C_2$-$C_6$)alkynylene group, wherein 1 to 4 methylene groups are optionally replaced by groups independently selected from O, —$S(O)_p$—, —$N(R^b)$—, or —$C(O)$—;

B is selected from hydrogen, heterocyclyl, cycloalkyl, aryl or heteroaryl;
wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, $S(O)_2NR^bR^b$, —$NR^bS(O)_2R^b$ or —$S(O)_pR^d$;
wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —$S(O)_pR^c$;

$R^b$ is independently selected from the group consisting of hydrogen, alkyl, acyl, carboxyalkyl, carbonylamino, cycloalkyl, cycloalkylalkyl, arylalkyl, heteroaryl heteroarylalkyl, heterocyclyl and heterocyclylalkyl;

$R^c$ is selected from hydrogen, alkyl, aryl, heteroaryl or heterocyclyl;

$R^d$ is selected from alkyl, cycloalkyl, aryl, heterocyclyl or heteroaryl; and p is 0, 1 or 2.

According to an embodiment, the present disclosure relates to compounds of formula (I) wherein Y is N;

$R^1$ is an alkyl, wherein one or more methylene groups are replaced by hetero atoms or groups such as —O—, —$S(O)_p$—, —$N(R^a)$—, or —$C(O)$ provided that the heteroatom is not adjacent to N in the ring; p is selected from 0, 1 or 2;
wherein alkyl is unsubstituted or substituted independently with alkoxy, acyl, acylamino, acyloxy, amino, monoalkylamino, dialkylamino, aminocarbonyl, alkoxycarbonylamino, cyano, halogen, haloalkyl, hydroxy, hydroxyalkyl, thiocarbonyl, carboxy, alkylcarboxy, carboxyalkyl, —$SO_3H$, aminocarbonylamino, hydroxyamino, alkoxyamino, —$S(O)_2NR^aR^a$, —$NR^aS(O)_2R^a$, or —$S(O)_pR^a$;

$R^2$ is selected from a group consisting of hydrogen, halogen, cyano, nitro, carboxy, acyl, aminocarbonyl, alkyl, alkenyl, alkynyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl and heteroaryloxy;

wherein alkyl, alkenyl, alkynyl, alkoxy, carboxyalkyl, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl, heteroaryloxy and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, haloalkoxy, amino, substituted amino, cyano or —S(O)$_p$R$^d$;

R$^3$ is selected from a group consisting of hydrogen, alkyl and arylalkyl;

X is an optionally substituted heteroarylene;

A is selected from (C$_1$-C$_6$)alkylene, (C$_2$-C$_6$)alkenylene or (C$_2$-C$_6$)alkynylene group, wherein 1 to 4 methylene groups are optionally replaced by groups independently selected from O, —S(O)$_p$—, —N(R$^b$)—, or —C(O)—;

wherein alkylene, alkenylene, and alkynylene are unsubstituted or substituted independently with alkyl, alkoxy, cycloalkyl, halogen, hydroxy, hydroxyalkyl, carboxy, alkylcarboxy, carboxyalkyl, carboxyalkyloxy, —SO$_3$H, hydroxyamino, alkoxyamino, S(O)$_2$NR$^c$R$^c$, —NR$^c$S(O)$_2$R$^c$ or —S(O)$_p$R$^d$;

B is selected from heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, —S(O)$_2$NR$^b$R$^b$, NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkylalkyl, halogen, haloalkyl, haloalkoxy, amino, substituted amino, cyano and —S(O)$_p$R$^d$;

R$^a$ is independently selected from the group consisting of hydrogen and alkyl;

R$^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

R$^c$ is selected from hydrogen, alkyl, aryl, heteroaryl or heterocyclyl;

R$^d$ is selected from alkyl, cycloalkyl, aryl, heterocyclyl or heteroaryl; and p is 0, 1 or 2.

A specific embodiment of the compounds of formula (I) is selected from:

8-(4-Benzyloxy-phenyl)-1-propyl-1,7-dihydro-purin-6-one,
1-Propyl-8-[1-(3-trifluoromethyl-benzyl)-1H-pyrazol-4-yl]-1,7-dihydro-purin-6-one,
8-(1-Benzyl-1H-pyrazol-4-yl)-1-propyl-1,7-dihydro-purin-6-one,
2-Chloro-8-[1-(2,3-difluoro-benzyl)-1H-pyrazol-4-yl]-1-propyl-1,7-dihydro-purin-6-one,
2-Chloro-8-[1-(3-fluoro-4-trifluoromethyl-benzyl)-1H-pyrazol-4-yl]-1-propyl-1,7-dihydro-purin-6-one,
2-Chloro-1-propyl-8-[1-(4-trifluoromethyl-benzyl)-1H-pyrazol-4-yl]-1,7-dihydro-purin-6-one,
8-[1-(3-Fluoro-4-trifluoromethyl-benzyl)-1H-pyrazol-4-yl]-1-propyl-1,7-dihydro-purin-6-one,
8-[1-(2,3-Difluoro-benzyl)-1H-pyrazol-4-yl]-1-propyl-1,7-dihydro-purin-6-one,
1-Propyl-8-[1-(4-trifluoromethyl-benzyl)-1H-pyrazol-4-yl]-1,7-dihydro-purin-6-one,
1-Propyl-8-(1H-pyrazol-4-yl)-1,7-dihydro-purin-6-one,
2-Chloro-8-[1-(3-fluoro-benzyl)-1H-pyrazol-4-yl]-1-propyl-1,7-dihydro-purin-6-one,
8-[1-(2,4-Difluoro-benzyl)-1H-pyrazol-4-yl]-1-propyl-1,7-dihydro-purin-6-one,
2-Chloro-1-propyl-8-[1-(3-trifluoromethyl-benzyl)-1H-pyrazol-4-yl]—1,7-dihydro-purin-6-one,
8-{4-[3-(4-Fluoro-phenyl)-prop-2-ynyloxy]-phenyl}-1-propyl-1,7-dihydro-purin-6-one,
8-{4-[5-Oxo-1-(4-trifluoromethoxy-phenyl)-pyrrolidin-3-ylmethoxy]-phenyl}-1-propyl-1,7-dihydro-purin-6-one,
1-Propyl-8-{4-[3-(3-trifluoromethyl-phenyl)-prop-2-ynyloxy]-phenyl}-1,7-dihydro-purin-6-one,
8-{4-[5-Oxo-1-(3-trifluoromethyl-phenyl)-pyrrolidin-3-yl-methoxy]-phenyl}-1-propyl-1,7-dihydro-purin-6-one,
2-Chloro-8-[1-(2,4-difluoro-benzyl)-1H-pyrazol-4-yl]-1-propyl-1,7-dihydro-purin-6-one,
8-[1-(3-Fluoro-benzyl)-1H-pyrazol-4-yl]-1-propyl-1,7-dihydro-purin-6-one,
2-Morpholin-4-yl-1-propyl-8-[1-(4-trifluoromethyl-benzyl)-1H-pyrazol-4-yl]-1,7-dihydro-purin-6-one,
N-(4-Cyano-phenyl)-2-[4-(6-oxo-1-propyl-6,7-dihydro-1H-purin-8-yl)-phenoxy]-acetamide,
[4-(6-Oxo-1-propyl-6,7-dihydro-1H-purin-8-yl)-phenoxy]-acetic acid,
8-(1-Benzyl-1H-pyrazol-4-yl)-2-chloro-1-propyl-1,7-dihydro-purin-6-one,
8-(4-{2-Oxo-2-[4-(3-trifluoromethyl-phenyl)-piperazin-1-yl]-ethoxy}-phenyl)-1-propyl-1,7-dihydro-purin-6-one,
8-(1-Benzyl-1H-pyrazol-4-yl)-1-propyl-2-(4-trifluoromethyl-benzylamino)-1,7-dihydro-purin-6-one,
8-(1-Benzyl-1H-pyrazol-4-yl)-1-propyl-2-(3-trifluoromethyl-benzylamino)-1,7-dihydro-purin-6-one,
8-(1-Benzyl-1H-pyrazol-4-yl)-2-[2-(4-methoxy-phenyl)-ethylamaino]-1-propyl-1,7-dihydro-purin-6-one,
8-(1-Benzyl-1H-pyrazol-4-yl)-2-phenethylamino-1-propyl-1,7-dihydro-purin-6-one, 8-(1-Benzyl-1H-pyrazol-4-yl)-2-(4-methyl-piperazin-1-yl)-1-propyl-1,7-dihydro-purin-6-one, 8-(1-Benzyl-1H-pyrazol-4-yl)-2-piperidin-1-yl-1-propyl-1,7-dihydro-purin-6-one, 8-{1-[1-(2,4-Difluoro-phenyl)-5-oxo-pyrrolidin-3-ylmethyl]-1H-pyrazol-4-yl}-1-propyl-1,7-dihydro-purin-6-one, 8-[1-(3-Fluoro-4-trifluoromethyl-benzyl)-1H-pyrazol-4-yl]-2-(2-hydroxy-ethylamino)-1-propyl-1,7-dihydro-purin-6-one, 2-Amino-1-propyl-8-[1-(3-trifluoromethyl-benzyl)-1H-pyrazol-4-yl]-1,7-dihydro-purin-6-one, 8-(1-Benzyl-1H-pyrazol-4-yl)-2-methylamino-1-propyl-1,7-dihydro-purin-6-one,

[8-(1-Benzyl-1H-pyrazol-4-yl)-6-oxo-1-propyl-6,7-dihydro-1H-purin-2-ylamino]-acetic acid ethyl ester, 8-(1-Benzyl-1H-pyrazol-4-yl)-2-methoxy-1-propyl-1,7-dihydro-purin-6-one, 1,2-Dipropyl-8-[1-(3-trifluoromethyl-benzyl)-1H-pyrazol-4-yl]-1,7-dihydro-purin-6-one, 1-Propyl-8-[1-(3-trifluoromethyl-benzyl)-1H-pyrazol-4-yl]-2-(4-trifluoromethyl-phenyl)-1,7-dihydro-purin-6-one, 1-Propyl-8-[1-(3-trifluoromethyl-benzyl)-1H-pyrazol-4-yl]-2-(3-trifluoromethyl-phenyl)-1,7-dihydro-purin-6-one, 2-(3-Fluoro-phenyl)-1-propyl-8-[1-(3-trifluoromethyl-benzyl)-1H-pyrazol-4-yl]-1,7-dihydro-purin-6-one, 2-Dimethylamino-1-propyl-8-[1-(3-trifluoromethyl-benzyl)-1H-pyrazol-4-yl]-1,7-dihydro-purin-6-one, 8-[1-(3-Fluoro-4-trifluoromethyl-benzyl)-1H-pyrazol-4-yl]-6-oxo-1-propyl-6,7-dihydro-1H-purine-2-carbonitrile, 8-[1-(3-Fluoro-4-trifluoromethyl-benzyl)-1H-pyrazol-4-yl]-6-oxo-1-propyl-6,7-dihydro-1H-purine-2-carboxylic acid, 8-(4-Benzyloxy-phenyl)-1-propyl-2-(3-trifluoromethyl-phenyl)-1,7-dihydro-purin-6-one, 8-{4-[3-(4-Fluoro-phenyl)-prop-2-ynyloxy]-phenyl}-1-propyl-2-(3-trifluoromethyl-phenyl)-1,7-dihydro-purin-6-one, 8-(4-Methoxy-phenyl)-1-propyl-2-(3-trifluoromethyl-phenyl)-1,7-dihydro-purin-6-one, 2-Ethyl-1-propyl-8-[1-(3-trifluoromethyl-benzyl)-1H-pyrazol-4-yl]-1,7-dihydro-purin-6-one, 2-Benzyl-1-propyl-8-[1-(3-trifluoromethyl-benzyl)-1H-pyrazol-4-yl]-1,7-dihydro-purin-6-one, {6-Oxo-1-propyl-8-[1-(3-trifluoromethyl-benzyl)-1H-pyrazol-4-yl]-6,7-dihydro-1H-purin-2-ylamino}-acetic acid, (S)-1-{6-Oxo-1-propyl-8-[1-(3-trifluoromethyl-benzyl)-1H-pyrazol-4-yl]-6,7-dihydro-1H-purin-2-yl}-pyrrolidine-2-carboxylic acid, 1-Propyl-2-pyrrolidin-1-yl-8-[1-(3-trifluoromethyl-benzyl)-1H-pyrazol-4-yl]-1,7-dihydro-purin-6-one, 2-Methylamino-1-propyl-8-[1-(3-trifluoromethyl-benzyl)-1H-pyrazol-4-yl]-1,7-dihydro-purin-6-one, 2-Cyclobutylamino-1-propyl-8-[1-(3-trifluoromethyl-benzyl)-1H-pyrazol-4-yl]-1,7-dihydro-purin-6-one, 2-Chloro-8-[1-(3-fluoro-4-trifluoromethyl-benzyl)-1H-pyrazol-4-yl]-7-methyl-1-propyl-1,7-dihydro-purin-6-one, 2-Methoxy-1-propyl-8-[1-(3-trifluoromethyl-benzyl)-1H-pyrazol-4-yl]-1,7-dihydro-purin-6-one, 6-Oxo-1-propyl-8-[1-(3-trifluoromethyl-benzyl)-1H-pyrazol-4-yl]-6,7-dihydro-1H-purine-2-carbonitrile, 2-Cyclopentyloxy-1-propyl-8-[1-(3-trifluoromethyl-benzyl)-1H-pyrazol-4-yl]-1,7-dihydro-purin-6-one, 6-Oxo-1-propyl-8-[1-(3-trifluoromethyl-benzyl)-1H-pyrazol-4-yl]-6,7-dihydro-1H-purine-2-carboxylic acid amide, {6-Oxo-1-propyl-8-[1-(3-trifluoromethyl-benzyl)-1H-pyrazol-4-yl]-6,7-dihydro-1H-purin-2-yloxy}-acetic acid ethyl ester, 2-Morpholin-4-yl-1-propyl-8-[1-(3-trifluoromethyl-benzyl)-1H-pyrazol-4-yl]-1,7-dihydro-purin-6-one, {6-Oxo-1-propyl-8-[1-(3-trifluoromethyl-benzyl)-1H-pyrazol-4-yl]-6,7-dihydro-1H-purin-2-yloxy}-acetic acid, 8-{1-[3-(4-Fluoro-phenyl)-prop-2-ynyl]-1H-pyrazol-4-yl}-1-propyl-2-pyrrolidin-1-yl-1,7-dihydro-purin-6-one, (S)-1-{6-Oxo-1-propyl-8-[1-(3-trifluoromethyl-benzyl)-1H-pyrazol-4-yl]-6,7-dihydro-1H-purin-2-yl}-pyrrolidine-2-carboxylic acid amide, 1-{6-Oxo-1-propyl-8-[1-(3-trifluoromethyl-benzyl)-1H-pyrazol-4-yl]-6,7-dihydro-1H-purin-2-yl}-piperidine-3-carboxylic acid, 1-{6-Oxo-1-propyl-8-[1-(3-trifluoromethyl-benzyl)-1H-pyrazol-4-yl]-6,7-dihydro-1H-purin-2-yl}-piperidine-4-carboxylic acid, (2R,4R)-4-Hydroxy-1-{6-oxo-1-propyl-8-[1-(3-trifluoromethyl-benzyl)-1H-pyrazol-4-yl]-6,7-dihydro-1H-purin-2-yl}-pyrrolidine-2-carboxylic acid, 2-(2,3-Dihydroxy-propylamino)-1-propyl-8-[1-(3-trifluoromethyl-benzyl)-1H-pyrazol-4-yl]-1,7-dihydro-purin-6-one, 2-(2-Methoxy-ethylamino)-1-propyl-8-[1-(3-trifluoromethyl-benzyl)-1H-pyrazol-4-yl]-1,7-dihydro-purin-6-one, 2-(4-Hydroxy-piperidin-1-yl)-1-propyl-8-[1-(3-trifluoromethyl-benzyl)-1H-pyrazol-4-yl]-1,7-dihydro-purin-6-one, 2-(3-Hydroxy-piperidin-1-yl)-1-propyl-8-[1-(3-trifluoromethyl-benzyl)-1H-pyrazol-4-yl]-1,7-dihydro-purin-6-one, 2-{6-Oxo-1-propyl-8-[1-(3-trifluoromethyl-benzyl)-1H-pyrazol-4-yl]-6,7-dihydro-1H-purin-2-ylamino}-ethanesulfonic acid, 2-(3-Hydroxymethyl-piperidin-1-yl)-1-propyl-8-[1-(3-trifluoromethyl-benzyl)-1H-pyrazol-4-yl]-1,7-dihydro-purin-6-one, (Methyl-{6-oxo-1-propyl-8-[1-(3-trifluoromethyl-benzyl)-1H-pyrazol-4-yl]-6,7-dihydro-1H-purin-2-yl}-amino)-acetic acid, 2-(2-Hydroxy-ethylamino)-1-propyl-8-[1-(3-trifluoromethyl-benzyl)-1H-pyrazol-4-yl]-1,7-dihydro-purin-6-one, 2-(4-Hydroxymethyl-piperidin-1-yl)-1-propyl-8-[1-(3-trifluoromethyl-benzyl)-1H-pyrazol-4-yl]-1,7-dihydro-purin-6-one, 2-(4-Hydroxymethyl-piperidin-1-yl)-1-propyl-8-[1-(3-trifluoromethyl-benzyl)-1H-pyrazol-4-yl]-1,7-dihydro-purin-6-one, (S)-3-Methyl-2-{6-oxo-1-propyl-8-[1-(3-trifluoromethyl-benzyl)-1H-pyrazol-4-yl]-6,7-dihydro-1H-purin-2-ylamino}-butyric acid, 2-((S)-2-Methoxymethyl-pyrrolidin-1-yl)-1-propyl-8-[1-(3-trifluoromethyl-benzyl)-1H-pyrazol-4-yl]-1,7-dihydro-purin-6-one, 2-((S)-2-Hydroxymethyl-pyrrolidin-1-yl)-1-propyl-8-[1-(3-trifluoromethyl-benzyl)-1H-pyrazol-4-yl]-1,7-dihydro-purin-6-one, 2-((R)-3-Hydroxy-pyrrolidin-1-yl)-1-propyl-8-[1-(3-trifluoromethyl-benzyl)-1H-pyrazol-4-yl]-1,7-dihydro-purin-6-one, 1-Propyl-2-(tetrahydro-pyran-4-ylamino)-8-[1-(3-trifluoromethyl-benzyl)-1H-pyrazol-4-yl]-1,7-dihydro-purin-6-one, 2-Fluoro-1-propyl-8-[1-(3-trifluoromethyl-benzyl)-1H-pyrazol-4-yl]-1,7-dihydro-purin-6-one, 1-Propyl-2-(2,2,2-trifluoro-ethoxy)-8-[1-(3-trifluoromethyl-benzyl)-1H-pyrazol-4-yl]-1,7-dihydro-purin-6-one, 2-(2-Methoxy-ethoxy)-1-propyl-8-[1-(3-trifluoromethyl-benzyl)-1H-pyrazol-4-yl]-1,7-dihydro-purin-6-one,
7-Methyl-1-propyl-8-[1-(3-trifluoromethyl-benzyl)-1H-pyrazol-4-yl]-1,7-dihydro-purin-6-one,
2-Chloro-1-propyl-8-[6-(3-trifluoromethyl-benzylamino)-pyridin-3-yl]-1,7-dihydro-purin-6-one,
2-Chloro-8-[6-(3-fluoro-benzylamino)-pyridin-3-yl]-1-propyl-1,7-dihydro-purin-6-one,
1-Propyl-8-[6-(3-trifluoromethyl-benzylamino)-pyridin-3-yl]-1,7-dihydro-purin-6-one,
1-Propyl-8-(1-pyridin-3-ylmethyl-1H-pyrazol-4-yl)-1,7-dihydro-purin-6-one,
1-Propyl-8-[1-(6-trifluoromethyl-pyridin-3-ylmethyl)-1H-pyrazol-4-yl]-1,7-dihydro-purin-6-one,
2-Cyclopropyl-1-propyl-8-[1-(3-trifluoromethyl-benzyl)-1H-pyrazol-4-yl]-1,7-dihydro-purin-6-one,
2-Difluoromethoxy-1-propyl-8-[1-(3-trifluoromethyl-benzyl)-1H-pyrazol-4-yl]-1,7-dihydro-purin-6-one,
1-Propyl-2-trifluoromethyl-8-[1-(3-trifluoromethyl-benzyl)-1H-pyrazol-4-yl]-1,7-dihydro-purin-6-one,
2-Chloro-8-(1-methyl-1H-pyrazol-4-yl)-1-propyl-1,7-dihydro-purin-6-one,
8-(1-Methyl-1H-pyrazol-4-yl)-1-propyl-1,7-dihydro-purin-6-one,
2-Isobutylamino-8-(1-methyl-1H-pyrazol-4-yl)-1-propyl-1,7-dihydro-purin-6-one,
8-(1-Methyl-1H-pyrazol-4-yl)-1-propyl-2-pyrrolidin-1-yl-1,7-dihydro-purin-6-one,
2-[2-(4-Methoxy-phenyl)-ethylamino]-8-(1-methyl-1H-pyrazol-4-yl)-1-propyl-1,7-dihydro-purin-6-one,
2-(4-Methyl-piperazin-1-yl)-8-(1-methyl-1H-pyrazol-4-yl)-1-propyl-1,7-dihydro-purin-6-one,
2-[4-(4-Fluoro-phenyl)-piperazin-1-yl]-8-(1-methyl-1H-pyrazol-4-yl)-1-propyl-1,7-dihydro-purin-6-one,
1-[8-(1-Methyl-1H-pyrazol-4-yl)-6-oxo-1-propyl-6,7-dihydro-1H-purin-2-yl]-pyrrolidine-2-carboxylic acid methyl ester,
2-Benzyl-8-(1-methyl-1H-pyrazol-4-yl)-1-propyl-1,7-dihydro-purin-6-one,
2-(3-Fluoro-phenyl)-8-(1-methyl-1H-pyrazol-4-yl)-1-propyl-1,7-dihydro-purin-6-one,
8-(1-Methyl-1H-pyrazol-4-yl)-1-propyl-2-(4-trifluoromethyl-phenyl)-1,7-dihydro-purin-6-one,
8-(1-Methyl-1H-pyrazol-4-yl)-2-phenethylamino-1-propyl-1,7-dihydro-purin-6-one,
8-(1-Methyl-1H-pyrazol-4-yl)-1-propyl-2-(4-trifluoromethyl-benzylamino)-1,7-dihydro-purin-6-one,
2-Cyclopropylamino-8-(1-methyl-1H-pyrazol-4-yl)-1-propyl-1,7-dihydro-purin-6-one,
2-(3-Fluoro-phenoxy)-8-(1-methyl-1H-pyrazol-4-yl)-1-propyl-1,7-dihydro-purin-6-one,
2-(4-Methoxy-phenylamino)-8-(1-methyl-1H-pyrazol-4-yl)-1-propyl-1,7-dihydro-purin-6-one,
7-Benzyl-2-chloro-8-(1-methyl-1H-pyrazol-4-yl)-1-propyl-1,7-dihydro-purin-6-one,
9-Benzyl-2-chloro-8-(1-methyl-1H-pyrazol-4-yl)-1-propyl-1,9-dihydro-purin-6-one,
2-Amino-7-benzyl-8-(1-methyl-1H-pyrazol-4-yl)-1-propyl-1,7-dihydro-purin-6-one,
2-Chloro-8-furan-2-yl-1-propyl-1,7-dihydro-purin-6-one,
2-Amino-8-[1-(4-fluoro-benzyl)-1H-imidazo[1,2-b]pyrazol-7-yl]-1-propyl-1,7-dihydro-purin-6-one,
2-Chloro-8-[1-(4-fluoro-benzyl)-1H-imidazo[1,2-b]pyrazol-7-yl]-1-propyl-1,7-dihydro-purin-6-one,
2-Amino-8-(1-methyl-1H-pyrazol-4-yl)-1-propyl-1,7-dihydro-purin-6-one,
2-Amino-7-methyl-8-(1-methyl-1H-pyrazol-4-yl)-1-propyl-1,7-dihydro-purin-6-one,
2-Amino-9-methyl-8-(1-methyl-1H-pyrazol-4-yl)-1-propyl-1,9-dihydro-purin-6-one,
7-Methyl-8-(1-methyl-1H-pyrazol-4-yl)-1-propyl-1,7-dihydro-purin-6-one,
9-Methyl-8-(1-methyl-1H-pyrazol-4-yl)-1-propyl-1,9-dihydro-purin-6-one,
2-Amino-8-furan-2-yl-1-propyl-1,7-dihydro-purin-6-one,
2-Chloro-8-furan-2-yl-7-methyl-1-propyl-1,7-dihydro-purin-6-one,
8-(1-Methyl-1H-pyrazol-4-yl)-1-propyl-2-(3-trifluoromethyl-benzylamino)-1,7-dihydro-purin-6-one,
2-Furan-2-yl-8-(1-methyl-1H-pyrazol-4-yl)-1-propyl-1,7-dihydro-purin-6-one,
8-(1-Benzyl-1H-pyrazol-4-yl)-2-furan-2-yl-1-propyl-1,7-dihydro-purin-6-one,
2-Chloro-8-(6-chloro-pyridin-3-yl)-1-propyl-1,7-dihydro-purin-6-one,
2-Difluoromethyl-1-propyl-8-[1-(3-trifluoromethyl-benzyl)-1H-pyrazol-4-yl]-1,7-dihydro-purin-6-one,
2-Fluoromethyl-1-propyl-8-[1-(3-trifluoromethyl-benzyl)-1H-pyrazol-4-yl]-1,7-dihydro-purin-6-one,
2-Fluoromethyl-8-{1-[3-(3-methoxy-phenyl)-prop-2-ynyl]-1H-pyrazol-4-yl}-1-propyl-1,7-dihydro-purin-6-one,
2-Difluoromethyl-8-{1-[2-oxo-2-(4-m-tolyl-piperazin-1-yl)-ethyl]-1H-pyrazol-4-yl}-1-propyl-1,7-dihydro-purin-6-one,
3-Fluoro-N-methyl-N-[5-(6-oxo-1-propyl-6,7-dihydro-1H-purin-8-yl)-pyridin-2-yl]-benzamide,
N-[5-(2-Difluoromethyl-6-oxo-1-propyl-6,7-dihydro-1H-purin-8-yl)-pyridin-2-yl]-3-methoxy-N-methyl-benzamide,
N-[5-(2-Difluoromethyl-6-oxo-1-propyl-6,7-dihydro-1H-purin-8-yl)-pyridin-2-yl]-3-methoxy-benzenesulfonamide;
2-Fluoromethyl-1-propyl-8-[1-(5-trifluoromethyl-pyridin-3-ylmethyl)-1H-pyrazol-4-yl]-1,7-dihydro-purin-6-one,
2-Fluoromethyl-1-propyl-8-[1-(2-trifluoromethyl-pyridin-4-ylmethyl)-1H-pyrazol-4-yl]-1,7-dihydro-purin-6-one,
2-Fluoromethyl-8-[3-(3-methoxy-phenoxy)-isoxazol-5-yl]-1-propyl-1,7-dihydro-purin-6-one,
2-Difluoromethyl-8-{3-[3-(3-fluoro-phenyl)-prop-2-ynyloxy]-isoxazol-5-yl}-1-propyl-1,7-dihydro-purin-6-one,
2-Fluoromethyl-1-(2-hydroxy-ethyl)-8-[3-(3-methoxy-phenoxy)-isoxazol-5-yl]-1,7-dihydro-purin-6-one,
2-Difluoromethyl-1-ethyl-8-{3-[3-(3-fluoro-phenyl)-prop-2-ynyloxy]-isoxazol-5-yl}-1,7-dihydro-purin-6-one,
2-Difluoromethyl-1-ethyl-8-(1-{2-[4-(3-methoxy-phenyl)-piperazin-1-yl]-2-oxo-ethyl}-1H-pyrazol-4-yl)-1,7-dihydro-purin-6-one,
1-Ethyl-8-(1-{2-[4-(3-methoxy-phenyl)-piperazin-1-yl]-2-oxo-ethyl}-1H-pyrazol-4-yl)-6-oxo-6,7-dihydro-1H-purine-2-carbonitrile,
N-[5-(2-Cyano-6-oxo-1-propyl-6,7-dihydro-1H-purin-8-yl)-pyridin-2-yl]-3-methoxy-benzenesulfonamide,
N-{5-[2-Cyano-1-(2-hydroxy-ethyl)-6-oxo-6,7-dihydro-1H-purin-8-yl]-pyridin-2-yl}-3-methoxy-benzenesulfonamide,
2-Difluoromethyl-1-ethyl-8-{4-[3-(3-methoxy-phenyl)-prop-2-ynyloxy]-phenyl}-1,7-dihydro-purin-6-one,
2-Difluoromethyl-1-ethyl-8-{4-[1-(3-fluoro-phenyl)-5-oxo-pyrrolidin-3-ylmethoxy]-phenyl}-1,7-dihydro-purin-6-one,
2-Difluoromethyl-8-[5-(3-methoxy-phenoxy)-1-methyl-1H-pyrazol-3-yl]-1-propyl-1,7-dihydro-purin-6-one, 2-Difluoromethyl-8-{5-[1-(3-methoxy-phenyl)-piperidin-4-yloxy]-1-methyl-1H-pyrazol-3-yl}-1-propyl-1,7-dihydro-purin-6-one, 2-Fluoromethyl-8-{3-[1-(3-fluoro-phenyl)-piperidin-4-yloxy]-isoxazol-5-yl}-1-propyl-1,7-dihydro-purin-6-one, 1-Ethyl-8-{6-[1-(3-fluoro-phenyl)-5-oxo-pyrrolidin-3-ylmethoxy]-pyridin-3-yl}-6-oxo-6,7-dihydro-1H-purine-2-carbonitrile, 1-Ethyl-8-{6-[1-(3-methoxy-phenyl)-pyrrolidin-3-yloxy]-pyridin-3-yl}-6-oxo-6,7-dihydro-1H-purine-2-carbonitrile, 3-[4-(2-Difluoromethyl-1-ethyl-6-oxo-6,7-dihydro-1H-purin-8-yl)-pyrazol-1-ylmethyl]-benzoic acid, 2-Difluoromethyl-1-ethyl-8-[1-(3-hydroxymethyl-benzyl)-1H-pyrazol-4-yl]-1,7-dihydro-purin-6-one, 2-Difluoromethyl-3-ethyl-6-[1-(3-methoxy-benzyl)-1H-pyrazol-4-yl]-3,5-dihydro-pyrrolo[3,2-d]pyrimidin-4-one, N-[5-(2-Cyano-4-oxo-3-propyl-4,5-dihydro-3H-pyrrolo[3,2-d]pyrimidin-6-yl)-pyridin-2-yl]-3-methoxy-benzenesulfonamide, 2-Fluoromethyl-6-{3-[1-(3-fluoro-phenyl)-piperidin-4-yloxy]-isoxazol-5-yl}-3-propyl-3,5-dihydro-pyrrolo[3,2-d]pyrimidin-4-one, 2-Difluoromethyl-6-{5-[1-(3-methoxy-phenyl)-piperidin-4-yloxy]-1-methyl-1H-pyrazol-3-yl}-3-propyl-3,5-dihydro-pyrrolo[3,2-d]pyrimidin-4-one, 3-Ethyl-6-{6-[1-(3-methoxy-phenyl)-pyrrolidin-3-yloxy]-pyridin-3-yl}-4-oxo-4,5-dihydro-3H-pyrrolo[3,2-d]pyrimidine-2-carbonitrile, 2-Fluoromethyl-6-{3-[1-(3-fluoro-phenyl)-piperidin-4-yloxy]-isoxazol-5-yl}-7-hydroxy-3-propyl-3,5-dihydro-pyrrolo[3,2-d]pyrimidin-4-one, 2-Difluoromethyl-3-ethyl-6-[1-(3-methoxy-benzyl)-1H-pyrazol-4-yl]-7-methyl-3,5-dihydro-pyrrolo[3,2-d]pyrimidin-4-one, 2-Difluoromethyl-1-ethyl-8-[1-(3-methoxy-benzyl)-1H-pyrazol-4-yl]-7-methyl-1,7-dihydro-purin-6-one, N-[5-(2-Cyano-7-methyl-6-oxo-1-propyl-6,7-dihydro-1H-purin-8-yl)-pyridin-2-yl]-3-methoxy-benzenesulfonamide, 1-(2,2-Difluoro-ethyl)-2-ethyl-8-[1-(3-methoxy-benzyl)-1H-pyrazol-4-yl]-1,7-dihydro-purin-6-one, 3-{3-[4-(2-Difluoromethyl-6-oxo-1-propyl-6,7-dihydro-1H-purin-8-yl)-pyrazol-1-yl]-prop-1-ynyl}-benzoic acid, 3-(3-{4-[1-(2,2-Difluoro-ethyl)-2-ethyl-6-oxo-6,7-dihydro-1H-purin-8-yl]-pyrazol-1-yl}-prop-1-ynyl)-benzoic acid, 3-{3-[4-(6-Oxo-1-propyl-2-trifluoromethyl-6,7-dihydro-1H-purin-8-yl)-pyrazol-1-yl]-prop-1-ynyl}-benzoic acid, or 6-Oxo-1-propyl-8-[6-(3-trifluoromethyl-benzyl)-pyridin-3-yl]-6,7-dihydro-1H-purine-2-carbonitrile.

In still another embodiment of the present invention, the compound of formula I forms a pharmaceutically acceptable salt, selected from acid addition salts or base addition salts.

In still another embodiment of the present invention, the compound of formula I is a stereoisomer or a tautomer.

It is another feature of the present invention to provide the use of compounds of formula (II) or its tautomers, polymorphs, stereoisomers, prodrugs, solvate or a pharmaceutically acceptable salts thereof, for the treatment of a pathological disease susceptible to improvement by antagonism of adenosine receptors,

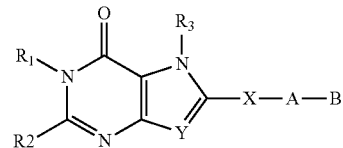

wherein Y is selected from N and CR; R is selected from H, hydroxy, alkoxy, alkyl, aryl;

$R^1$ is selected from a group consisting of alkyl, alkenyl, alkynyl, cycloalkyl, cycloalkylalkyl, aryl, arylalkyl, heterocyclyl, heterocyclylalkyl, heteroaryl and heteroarylalkyl; wherein one or more methylene groups of alkyl, alkenyl, alkynyl, are replaced by hetero atoms or groups such as —O—, —S(O)$_p$—, NR$^a$R$^a$, or —C(O)—, provided that the heteroatom is not adjacent to N in the ring; p is selected from 0, 1 or 2;

wherein alkyl, alkenyl, alkynyl, cycloalkyl, cycloalkylalkyl, aryl, arylalkyl, heterocyclyl, heterocyclylalkyl, heteroaryl and heteroarylalkyl are unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$, —S(O)$_p$R$^b$, cycloalkyl, aryl, heterocyclyl or heteroaryl;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, haloalkoxy, amino, substituted amino, cyano or —S(O)$_p$R$^c$;

$R^2$ is selected from a group consisting of hydrogen, halogen, cyano, nitro, carboxy, acyl, aminocarbonyl, alkyl, alkenyl, alkynyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl and heteroaryloxy;

wherein alkyl, alkenyl, alkynyl, alkoxy, carboxyalkyl, cycloalkyl, cycloalkylalkyl, cycloalkyloxy, aryl, arylalkyl, aryloxy, heterocyclyl, heterocyclylalkyl, heterocyclyloxy, heteroaryl, heteroarylalkyl, heteroaryloxy and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, halogen, haloalkyl, haloalkoxy, amino, substituted amino, cyano or —S(O)$_p$R$^d$;

R$^3$ is selected from a group consisting of hydrogen, alkyl, alkenyl, alkynyl, alkoxyalkyl, cycloalkyl, cycloalkylalkyl, aryl, arylalkyl, heteroaryl and heteroarylalkyl;

wherein alkyl, alkenyl, alkynyl, alkoxyalkyl, cycloalkyl, cycloalkylalkyl, aryl, arylalkyl, heteroaryl, and heteroarylalkyl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^c$R$^c$, —NR$^c$S(O)$_2$R$^c$ or —S(O)$_p$R$^d$;

wherein, each substituent is unsubstituted or substituted with 1, 2, or 3 substituents independently selected from alkyl, carboxy, carboxyalkyl, aminocarbonyl, hydroxyd, alkoxy, halogen, CF$_3$, amino, substituted amino, cyano or —S(O)$_p$R$^d$;

X is either an optionally substituted arylene or an optionally substituted heteroarylene;

A is selected from a bond, (C$_1$-C$_6$)alkylene, (C$_2$-C$_6$)alkenylene or (C$_2$-C$_6$)alkynylene group, wherein 1 to 4 methylene groups are optionally replaced by groups independently selected from O, —S(O)$_p$—, —N(R$^b$)—, or —C(O)—;

wherein alkylene, alkenylene, and alkynylene are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, halogen, CF$_3$, amino, substituted amino, cyano or —S(O)$_p$R$^d$;

B is selected from hydrogen, heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, diallylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano or —S(O)$_p$R$^d$;

R$^a$ is independently selected from the group consisting of hydrogen and alkyl;

R$^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

R$^c$ is selected from hydrogen, alkyl, aryl, heteroaryl or heterocyclyl;

R$^d$ is selected from alkyl, cycloalkyl, aryl, heterocyclyl or heteroaryl; and p is 0, 1 or 2.

The present invention also relates to the process of preparation of compounds of formula (I), or pharmaceutically acceptable salts thereof.

The compounds of formula (I) may be prepared as outlined in Scheme 1 and 2 below:

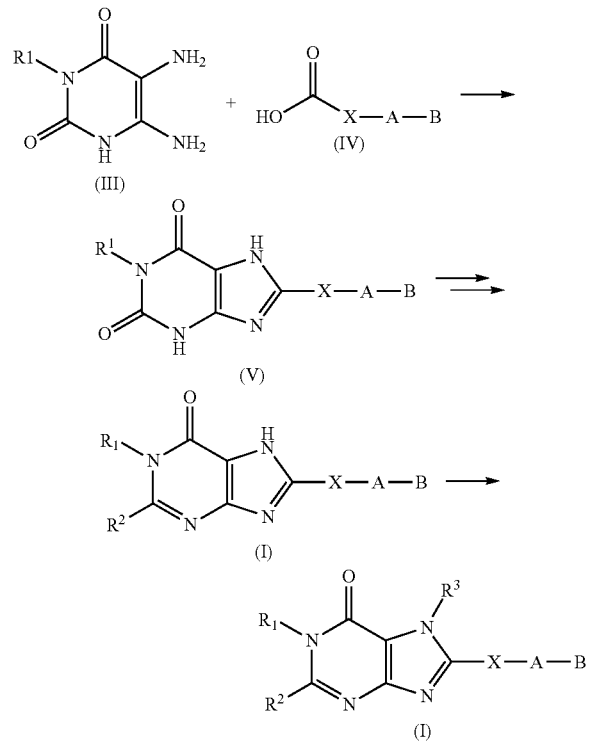

As exemplified in Scheme 2 above, diamine of formula (III) where in R$^1$ is as defined herein above, may be coupled with carboxylic acid of formula (IV) or its acid chloride wherein all symbols are defined herein above and cyclised to provide compounds of formula (V) which may be chlorinated followed by reacting with R$^2$-LG wherein LG is NH$_2$, B(OH)$_2$, MgBr, ZnCl, OH and R$^2$ is defined herein above to provide compounds of formula (I) wherein R$^3$ is hydrogen and all other symbols are defined herein above. Compounds of formula (I) may further be reacted with R$^3$-Hal to provide compounds of formula (I) wherein R$^3$ is other than hydrogen and is as defined herein above.

Schemes 3-7 further describes synthesis of compounds of formula (I)

Scheme 2:

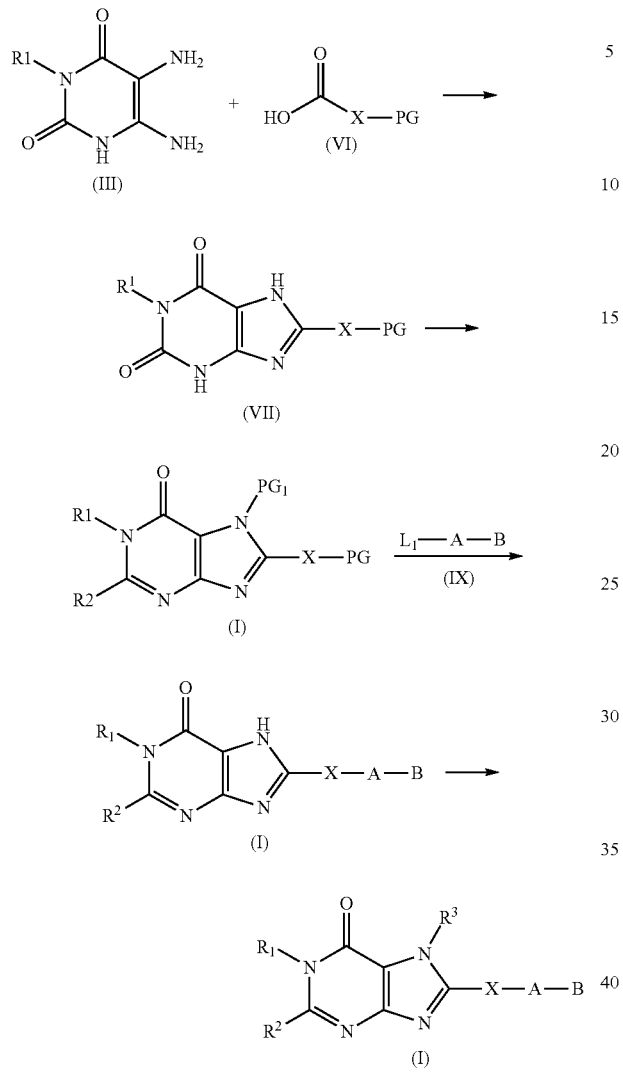

As exemplified in Scheme 2 above, diamine of formula (III) where in $R^1$ is as defined herein above, may be coupled with carboxylic acid of formula (VI) or its acid chloride wherein PG is a protecting group and all other symbols are defined herein above and cyclised to provide compounds of formula (VII) which may be chlorinated followed by reacting with $R^2$-LG wherein LG is $NH_2$, $B(OH)_2$, MgBr, ZnCl, OH and $R^2$ is defined herein above followed by protection of the amino group to provide compounds of formula (VIII) which may be reacted with compounds of formula (IX) wherein L1 is a leaving group and A and B are as defined herein above followed by deprotection to provide compounds of formula (I) wherein $R^3$ is hydrogen and all other symbols are defined herein above. Compounds of formula (I) may further be reacted with $R^3$-Hal to provide compounds of formula (I) wherein $R^3$ is other than hydrogen and is as defined herein above.

Scheme 3:

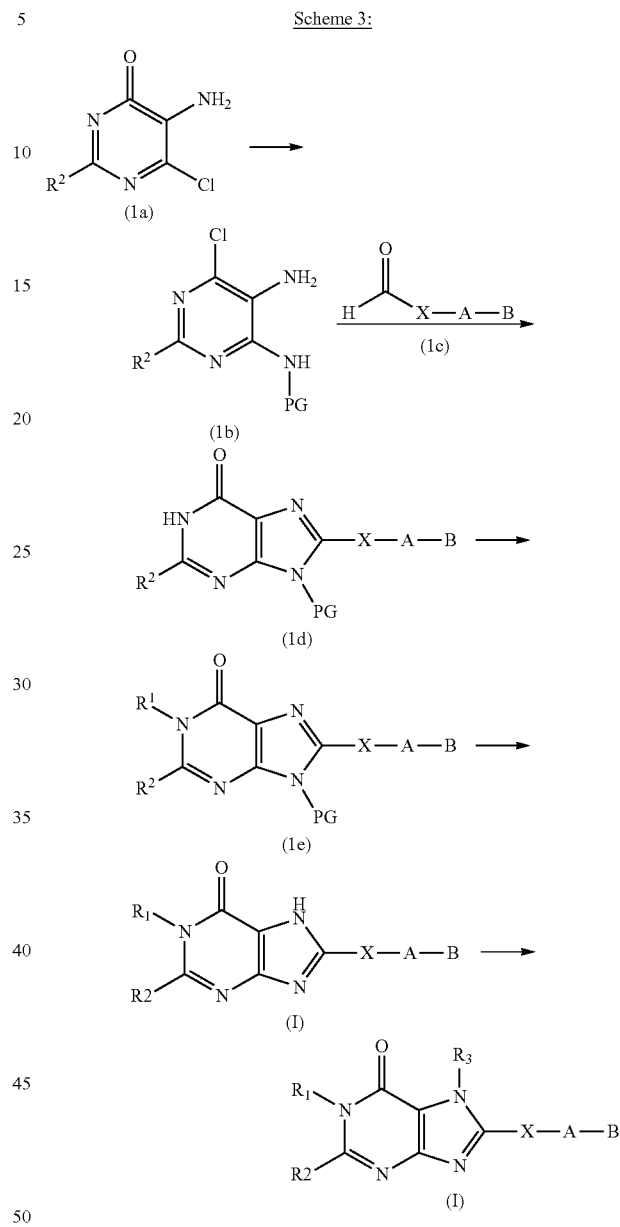

As exemplified in scheme 3 above, pyrimidine derivative of formula (1a) which is available commercially may be reacted with $PG-NH_2$ such as benzylamine, allylamine and the like to obtain compound of formula (1b). The reaction may be carried out in a solvent such as ethanol, methanol, THF and the like, in an inert atmosphere. The reaction temperature may range from 40° C. to 70° C. The reaction time may range from 6 to 20 hours.

The compound of formula (1b) may be condensed with an aldehyde of formula (1c) in the presence of a suitable solvent or a mixture of solvents, preferably mixture of acetic acid and THF, then refluxed with formic acid to obtain the compound of formula (1d) wherein PG is a protective group and all other symbols are as defined herein above. The reaction temperature may range from 80° C. to 120° C. The reaction time may range from 12 to 36 hours.

The compounds of formula (1d) may be converted into compounds of formula (1e) by reacting with $R^1$-Hal wherein $R^1$ is defined herein above. The reaction may be carried out in a solvent such as acetone or DMF, in the presence of a base such as $K_2CO_3$, $Cs_2CO_3$ or in presence of a suitable organic base such as DBU. The reaction temperature may range from 20 to 40° C.

The protecting group of the compound of (1e) may be removed by means well known in the art to provide compounds of formula I, wherein $R^3$ is H, which is reacted with $R^3$-Hal wherein $R^3$ is defined herein above to provide the desired compound of formula (I) wherein $R^3$ is not H and all other symbols are as defined herein above.

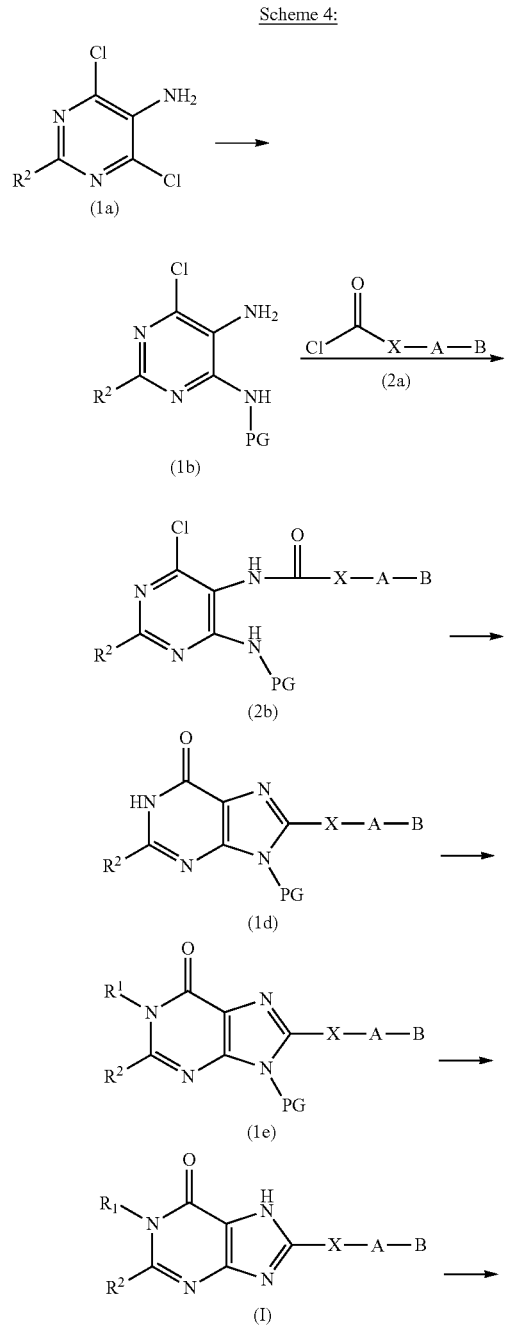

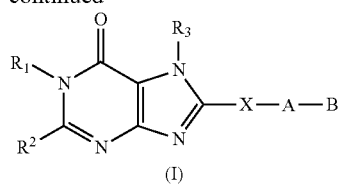

The compounds of formula (1d) may also be prepared by reacting acid chloride of formula (2a) with (1b) to provide (2b). The reaction may be carried out in a basic solvent such as pyridine, N-methylpyrrolidinone and the like or alternatively in an inert solvent such as THF, DCM, N,N-dimethyl acetamide and the like in presence of suitable organic base such as triethylamine, diisopropyl amine and the like. The reaction temperature may range from 0° C. to room temperature. The reaction time may range from 4 to 48 hours. The acid halides (2a) may be commercially available or can be prepared by conventional methods well-known to those skilled in the art. The intermediate (2b) may then be cyclized to obtain compounds of formula (1d) by refluxing in a weak acid such as formic acid, acetic acid and the like or with sulphuric acid in an appropriate solvent such as isopropanol, toluene and the like. The reaction time may range from 6-36 hours.

The compounds of formula (1d) may be converted into compounds of formula (1e) by reaction with $R^1$-Hal wherein $R^1$ is defined herein above. The reaction may be carried out in a solvent such as acetone or DMF, in the presence of a base such as $K_2CO_3$, $Cs_2CO_3$ or in presence of a suitable organic base such as DBU. The reaction temperature may range from 20 to 40° C.

The protecting group of the compound of (1e) may be removed by means well known in the art to provide compounds of formula I, wherein $R^3$ is H, which is reacted with $R^3$-Hal wherein $R^3$ is defined herein above to provide the desired compound of formula (I) wherein $R^3$ is not H and all other symbols are as defined herein above.

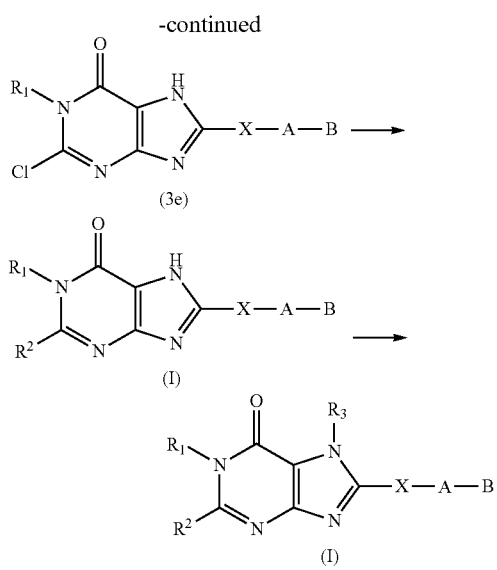

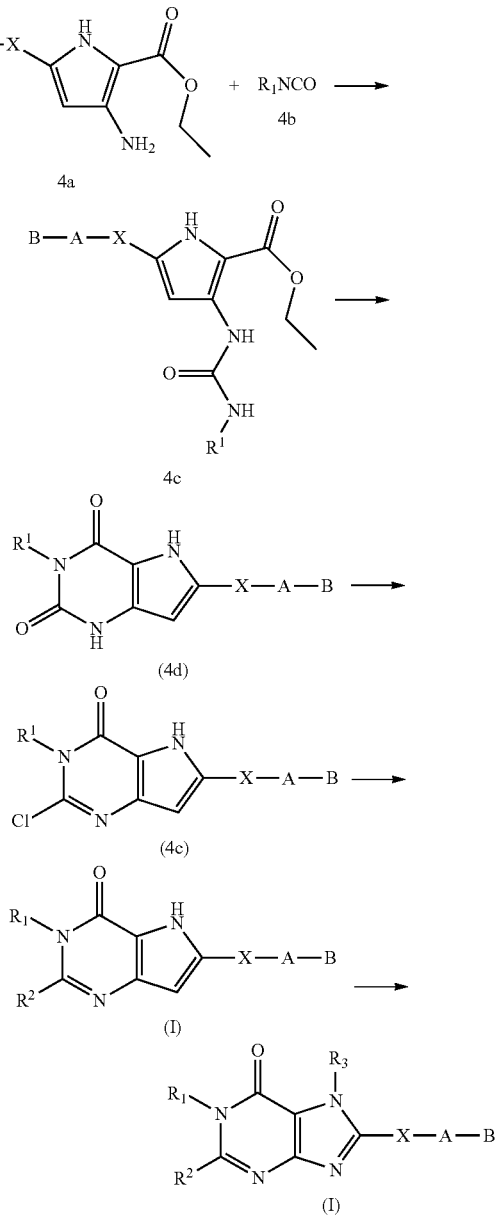

Alternatively, compounds of formula (3e) may be converted to compounds of formula (I) by reacting with $R^2$—$NH_2$, $R^2R^2NH$, $R^2$—$B(OH)_2$, $R^2MgBr$, $R^2ZnCl$, $R^2OH$ wherein $R^2$ is defined herein above, by methods well known in the art to provide compounds of formula I, wherein $R^3$ is H and all other symbols are defined herein above which may be further reacted with $R^3$-Hal wherein $R^3$ is defined herein above to provide the desired compound of formula (I) wherein $R^3$ is not H and all other symbols are as defined herein above.

The compound of formula (3a), wherein all symbols are defined earlier is prepared by means well known in the art (US2008/0194593).

A compound of formula (3a) is reacted with a carboxylic acid of formula (3b), (which is available commercially or prepared by means well known in the art), wherein all symbols are defined earlier, to yield a compound of formula (3c). The reaction may be carried out using a suitable coupling agent such as EDI, DCC, HBTU, HATU and the like in a protic solvent such as methanol, ethanol, propanol and the like or an aprotic solvent such as DMF, $CH_2Cl_2$ and the like at a temperature in the range of 20-30° C. for 4 to 16 hours to provide compound of formula (3c).

The compound (3c) may also be prepared from reaction of (3a) with an acid halide of (3b). The reaction is carried out in a solvent such as acetonitrile, THF and the like, in the presence of tertiary base such as triethyl amine. The reaction temperature may range from 0° C. to reflux temperature of the solvent(s) used. The reaction time may range from 4 to 48 hours. After completion of reaction the product of formula (3c) is isolated by conventional methods.

The compound of formula (3c) is cyclised to obtain compounds of formula (3d) by a cyclization reaction. The reaction may be carried out in the presence of hexamethyldisilazane and ammonium sulphate for about 24-48 hours at reflux temperature.

Compounds of formula (3d) may be converted to compounds of formula (3e) by treatment with dehydrating agent such as $POCl_3$ or in combination with $POCl_3$ and $PCl_5$, at reflux temperature for about 24 hours. Alternatively (3c) may be converted into compounds of formula (3e) by reaction with dehydrating agent such as $POCl_3$ or in combination with $POCl_3$—$PCl_5$, at reflux temperature for about 24 hours.

Dehalogenation of the compounds of formula (3e) may be carried out using hydrogenation or by transfer hydrogenation in the presence of a suitable catalyst such as Pd/C, $Pd(OH)_2$/C and the like. In general, the compound of formula (3e) may be dissolved in DMF and treated with ammonium formate in presence of 10% Pd/C and water at a temperature of about 60-65° C. The reaction time may range from 1 to 18 hours. After completion of reaction, the compounds of formula (I) wherein $R^2$ and $R^3$ are hydrogen and all other symbols are defined herein above may be isolated by conventional methods.

The compound of formula (4a) wherein all symbols are defined earlier is prepared by means well known in the art (J. Med. Chem., 2005, 48, 2420-2431, J. Org. Chem., 2000, 65, 2603-2605). The compound of formula (4a) can be converted to compound (4c) by reaction with appropriate isocyanate of formula (4b), wherein all symbols are defined earlier. The reaction may be carried out in an inert solvent, for example toluene, benzene and the like. The reaction temperature may range from room temperature to reflux temperature of the solvent used, preferably at room temperature. The reaction time may range from 1 to 24 hours. After completion of reaction, the product of formula (4c) is isolated by conventional method.

The compound of formula (4c) is then converted into a compound of general formula (4d) by a cyclization reaction. The reaction may be carried out in a protic solvent, for example methanol, ethanol, propanol and the like, preferably methanol, in presence of a base, for example alkali metal hydroxide such as potassium hydroxide, sodium hydroxide and the like, or sodium methoxide, sodium ethoxide, potassium tert-butoxide, preferably aqueous potassium hydroxide, at a temperature 50-100° C., preferably at 80° C. The reaction time may range from 1 to 12 hours, preferably about 6-10 hours. After completion of reaction the product of formula (4d) is isolated by conventional method.

Compounds of formula (4d) may be converted to compounds of formula (4e) by treatment with dehydrating agent $POCl_3$ or in combination with $POCl_3$—$PCl_5$, at reflux temperature for about 24 hours. After completion of reaction, (4e) is isolated conventionally.

Dehalogenation of the compounds of formula (4e) may be carried out using hydrogenation or by transfer hydrogenation in the presence of a suitable catalyst such as Pd/C, $Pd(OH)_2/C$ and the like. In general, the compound of formula (4e) may be dissolved in DMF and treated with ammonium formate in presence of 10% Pd/C and water at a temperature of about 60-65° C. The reaction time may range from 1 to 18 hours. After completion of reaction, the compounds of formula (I) wherein $R^2$ and $R^3$ are hydrogen and all other symbols are defined herein above may be isolated by conventional methods.

Alternatively, compounds of formula (4e) may be converted to compounds of formula (I) by reacting with $R^2$—$NH_2$, $R^2R^2NH$, $R^2$—$B(OH)_2$, $R^2MgBr$, $R^2ZnCl$, $R^2OH$ wherein $R^2$ is defined herein above, by methods well known in the art to provide compounds of formula I, wherein $R^3$ is H and all other symbols are defined herein above which may be further reacted with $R^3$-Hal wherein $R^3$ is defined herein above to provide the desired compound of formula (I) wherein $R^3$ is not H and all other symbols are as defined herein above.

Scheme 7:

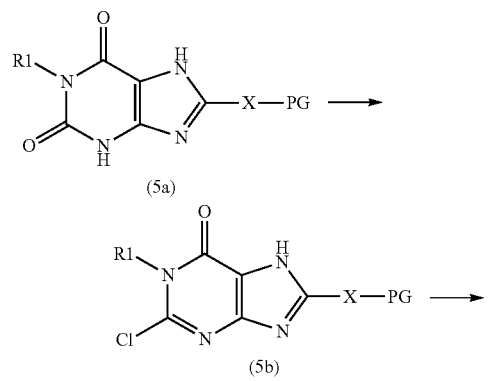

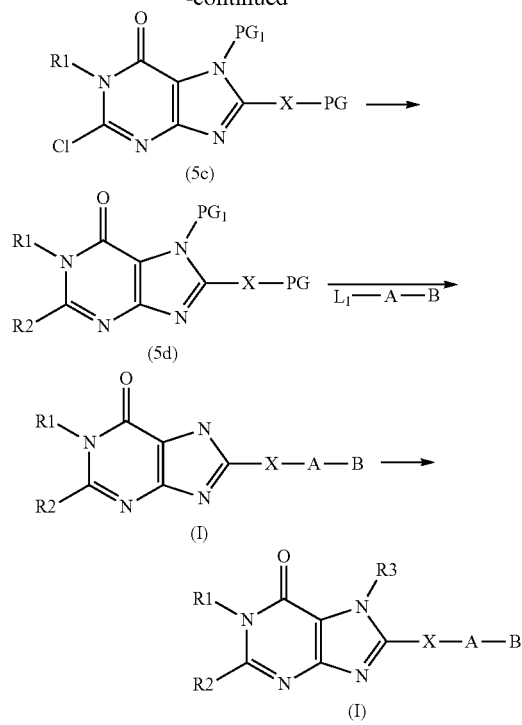

The compound of formula (5a) wherein all symbols are as defined earlier is prepared by means well known in the art. The compound of formula (5b) wherein all the symbols are defined as earlier is prepared by methods as described in Scheme 3. The compound of formula (5c), wherein all the symbols are as defined earlier and PG is the protecting group such as benzyl and the like, may be prepared from compound of formula (5b) by reaction with PG1-Hal wherein PG1 may be SEM, and the like. The reaction may be carried out using base such as $K_2CO_3$ and aprotic solvent for example DMF, DMSO, acetonitrile and the like. The reaction temperature may range from room temperature to reflux temperature of the solvent used, preferably at room temperature. The reaction time may range from 1 to 24 hours. After completion of reaction, the product of formula (5c) is isolated by conventional method.

The compounds of formula (5c) may be converted to compounds of formula (5d) by reacting with $R^2$—$NH_2$, $R^2R^2NH$, $R^2$—$B(OH)_2$, $R^2MgBr$, $R^2ZnCl$, $R^2OH$ wherein $R^2$ is defined herein above, by methods well known in the art to provide compounds of formula (5d).

The compounds of formula (5d) may be converted to compounds of formula (I) by deprotection of PG and followed by reaction with L1-A-B wherein A, B are defined herein above and L1 is leaving group such as halo (chloro, bromo, iodo etc), mesylate, tosylate and the like. The reaction may be carried out in a solvent such as acetone or DMF, in the presence of a base such as $K_2CO_3$, $Cs_2CO_3$ and the like. The reaction temperature may range from room temperature to reflux temperature of the solvent used, preferably at 50-80° C. The reaction time may range from 1 to 24 hours. The deprotection of PG1 can be carried out either using acidic condition or basic condition depending on the nature of PG1. After completion of reaction, the product of formula (I) is isolated by conventional method, wherein $R^3$ is H and all other symbols are defined herein above which may be further reacted with $R^3$-Hal wherein $R^3$ is defined herein above to provide the desired compound of formula (I) wherein $R^3$ is not H and all other symbols are as defined herein above.

Wherever desired or necessary, in any of the above mentioned processes, functional groups may be transformed to different functional groups such as an ester function being converted to an acid, amide, hydroxymethyl, keto, aldehyde as well as an ester. The said conversions may be carried out using reagents and conditions well documented in the literature.

Wherever desired or necessary, in any of the above mentioned processes, any of the compounds of formula (I) may be converted into a pharmaceutically acceptable salt or vice versa or converting one salt form into another pharmaceutically acceptable salt form. According to an embodiment, the compounds of the present invention are adenosine $A_{2B}$ receptor antagonists. Thus, the present invention provides a method for the modulation of adenosine $A_{2B}$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

According to another embodiment, it provides the use of compounds of formula II as adenosine $A_{2B}$ receptor antagonists. Thus, the present invention provides a method for the modulation of adenosine $A_{2B}$ receptor activity in mammals which method comprises administering to a mammal in need thereof a therapeutically effective amount of compound of formula II or its tautomers, polymorphs, stereoisomers, prodrugs, solvate or a pharmaceutically acceptable salts thereof.

According to an embodiment, the compounds of the present invention are adenosine $A_{2A}$ receptor antagonists. Thus, the present invention provides a method for the modulation of adenosine $A_{2A}$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

According to yet another embodiment, it provides the use of compound of formula II as adenosine $A_{2A}$ receptor antagonists. Thus, the present invention provides a method for the modulation of adenosine $A_{2A}$ receptor activity in mammals which method comprises administering to a mammal in need thereof a therapeutically effective amount of compound of formula II or its tautomers, polymorphs, stereoisomers, prodrugs, solvate or a pharmaceutically acceptable salts thereof.

According to yet another embodiment, the compounds of the present invention are adenosine $A_{2A}$ and $A_{2B}$ antagonist or adenosine $A_1$ and $A_{2B}$ antagonist or $A_1$, $A_{2A}$ and $A_{2B}$ antagonist thereby providing dual or pan antagonistic activity through additive/synergistic effect. Thus, the present invention provides a method for the modulation of adenosine $A_{2A}$ and $A_{2B}$ or $A_1$ and $A_{2B}$ or $A_1$, $A_{2A}$ and $A_{2B}$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

Yet in another embodiment it provides the use of compounds of formula II as adenosine $A_{2A}$ and $A_{2B}$ antagonist or adenosine $A_1$ and $A_{2B}$ antagonist or $A_1$, $A_{2A}$ and $A_{2B}$ antagonist thereby providing dual or pan antagonistic activity through additive/synergistic effect. Thus, the present invention provides a method for the modulation of adenosine $A_{2A}$ and $A_{2B}$ or $A_1$ and $A_{2B}$ or $A_1$, $A_{2A}$ and $A_{2B}$ receptor activity in mammals which method comprises administering to a mammal in need thereof a therapeutically effective amount of compound of formula II or its tautomers, polymorphs, stereoisomers, prodrugs, solvate or a pharmaceutically acceptable salts thereof.

The present invention also provides a method of prophylactic or therapeutic treatment of disease or disorder susceptible to improvement by antagonism of adenosine receptor comprising administering an effective amount of compound of formula I or its tautomers, polymorphs, stereoisomers, prodrugs, solvate or a pharmaceutically acceptable salts thereof, to a mammal in need of such treatment.

The present invention further provides a method of prophylactic or therapeutic treatment of disease or disorder susceptible to improvement by antagonism of adenosine receptor comprising administering an effective amount of compound of formula II or its tautomers, polymorphs, stereoisomers, prodrugs, solvate or a pharmaceutically acceptable salts thereof, to a mammal in need of such treatment.

As used throughout the specification and in the claims, the term "treatment" embraces all the different forms or modes of treatment as known to those of the pertinent art and in particular includes preventive, curative, delay of progression and palliative treatment.

The term "therapeutically effective amount" as used herein refers to an amount of a drug or a therapeutic agent that will elicit the desired biological or medical response of a tissue, system or an animal (including man) that is being sought by a researcher or clinician.

The term "mammal" or "patient" are used interchangeably herein and include, but are not limited to, humans, dogs, cats, horses, pigs, cows, sheep, monkeys, rabbits, mice and laboratory animals The preferred mammals are humans.

The present invention further provides pharmaceutical compositions comprising a therapeutically effective amount of a compound of the present invention, alone or in combination with one or more pharmaceutically acceptable carriers.

The pharmaceutical compositions according to the invention are those suitable for enteral, such as oral or rectal, transdermal and parenteral administration to mammals, including man, for the treatment of conditions mediated by the adenosine $A_{2A}$ receptor or adenosine $A_{2B}$ receptor. Such conditions include, but are not limited to, asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

Generally, the concentration of the compound(s) of the present invention in a liquid composition, such as a lotion, will be from about 0.01-about 25 wt %, preferably from about 0.1-about 10 wt %. The concentration in a semi-solid or a solid composition such as a gel or a powder will be about 0.1-about 5 wt %, preferably about 0.5-about 25 wt %.

The amount of a compound of the present invention required for use in treatment will vary not only with the particular salt selected but also with the route of administration, the nature of the condition being treated and the age and condition of the patient and will be ultimately at the discretion of the administering physician or clinician. In general, a suitable dose will be in the range of from about 0.001 mg/kg/day to about 20 mg/kg/day For example, a dosage may be from about 0.002 mg/kg to about 10 mg/kg of body weight per day, from about 0.01 mg/kg/day to about 1 mg/kg/day, and from about 0.1 mg/kg/day to about 5 mg/kg/day.

The compound is conveniently administered in unit dosage form, e.g., containing 5 to 1000 µg, about 10 to about 750 µg, about 50 to about 500 µg of active ingredient per unit dosage form.

The desired dose may conveniently be presented in a single dose or as divided doses administered at appropriate intervals, for example, as two, three, four or more sub-doses per day. The sub-dose itself may be further divided, e g, into a number of discrete loosely spaced administrations; such as multiple inhalations from an insufflator or by application of a plurality of drops into the eye Dosages above or below the range cited herein above are within the scope of the present invention and may be administered to the individual patient if desired and necessary.

Accordingly, in various embodiments, the present invention provides pharmaceutical compositions as described above for the treatment of conditions mediated by adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

In various embodiments, the present invention provides pharmaceutical compositions comprising a therapeutically effective amount of a compound of the invention in combination with a therapeutically effective amount of another therapeutic agent, preferably selected from anti-inflammatory agents, anti-diabetic agents, anti-hypertensive agents and anti-dyslipidemic agents.

According to an embodiment, the pharmaceutical compositions may contain a therapeutically effective amount of a compound of the invention as defined above, either alone or in a combination with another therapeutic agent, e.g., each at an effective therapeutic dose as reported in the art. Such therapeutic agents include: a) anti-inflammatory agents, such as anticholinergic or antimuscarinic agents; steroids; $LTB_4$ (leukotriene $B_4$) antagonists; dopamine receptor agonists; $PDE_4$ (phosphodiesterase 4) inhibitors; and beta-2 adrenergic receptor agonists; b) anti-diabetic agents, such as insulin, insulin derivatives and mimetics; insulin secretagogues; insulinotropic sulfonylurea receptor ligands; thiazolidone derivatives; GSK3 (glycogen synthase kinase-3) inhibitors; sodium-dependent glucose co-transporter inhibitors; glycogen phosphorylase A inhibitors; biguanides; alpha-glucosidase inhibitors; GLP-1 (glucagon like peptide-1), GLP-1 analogs and GLP-1 mimetics; modulators of PPARs (peroxisome proliferator-activated receptors); DPPIV (dipeptidyl peptidase IV) inhibitors; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products); c) anti-hypertensive agents, such as loop diuretics; angiotensin converting enzyme (ACE) inhibitors; inhibitors of the Na—K-ATPase membrane pump such as digoxin; neutralendopeptidase (NEP) inhibitors; ACE/NEP inhibitors; angiotensin II antagonists; renin inhibitors; β-adrenergic receptor blockers; inotropic agents; calcium channel blockers; aldosterone receptor antagonists; and aldosterone synthase inhibitors; and d) anti-dyslipidemic agents such as 3-hydroxy-3-methyl-glutaryl coenzyme A (HMG-CoA) reductase inhibitors; HDL increasing compounds such as cholesterol ester transfer protein (CETP) inhibitors; squalene synthase inhibitors; FXR (farnesoid X receptor) and LXR (liver X receptor) ligands; cholestyramine; fibrates; nicotinic acid; and aspirin.

According to another embodiment, the present invention provides pharmaceutical compositions comprising a therapeutically effective amount of a compound of formula I of the invention for the treatment of cancer such as cancers of the lung, liver, breast, pancreas, thyroid, skin, central nervous system, larynx, gastrointestine, colon, rectum, bladder, vascular endothelium, esophagus, colorectal, renal, prostate, cervical, ovaries, and endometrial, melanoma, squamous cell and basal cell carcinoma.

According to yet another embodiment, the present invention provides pharmaceutical compositions comprising a therapeutically effective amount of a compound of formula II for the treatment of cancer such as cancers of the lung, liver, breast, pancreas, thyroid, skin, central nervous system, larynx, gastrointestine, colon, rectum, bladder, vascular endothelium, esophagus, colorectal, renal, prostate, cervical, ovaries, and endometrial, melanoma, squamous cell and basal cell carcinoma.

According to yet another embodiment, the present invention provides pharmaceutical compositions comprising a therapeutically effective amount of a compound of formula I, for the treatment of Parkinson's disease either alone or in a combination with another therapeutic agent, e.g., each at an effective therapeutic dose as reported in the art. Such therapeutic agents include: L-DOPA, dopaminergic agonists, MAO-B inhibitors, DOPA decarboxylase inhibitors and catechol-O-methyltransferase (COMT) inhibitors.

In an another embodiment, the present invention provides pharmaceutical compositions comprising a therapeutically effective amount of a compound of formula II, for the treatment of Parkinson's disease either alone or in a combination with another therapeutic agent, e.g., each at an effective therapeutic dose as reported in the art. Such therapeutic agents include: L-DOPA, dopaminergic agonists, MAO-B inhibitors, DOPA decarboxylase inhibitors and catechol-O-methyltransferase (COMT) inhibitors.

As described above, a compound of the present invention may be administered either simultaneously, before or after another active ingredient, either separately by the same or different route of administration or together in the same pharmaceutical formulation.

The present invention further relates to pharmaceutical compositions as described above for use as a medicament.

The present invention further relates to use of pharmaceutical compositions or combinations as described above for the preparation of a medicament for the treatment of conditions mediated by adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

According to an embodiment, the present invention provides use of compound of formula (I) for the treatment of conditions mediated by adenosine receptor.

Further, in another embodiment, the present invention provides use of compound of formula II for the treatment of conditions mediated by adenosine receptor.

According to an embodiment, the present invention provides use of compound of formula (I) for the treatment of asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, autoimmune diseases. Parkinson's disease, Alzheimer's disease, restless leg syndrome, nocturnal myoclonus, cerebral ischaemia, Huntington's disease, Wilson's disease, multiple system atrophy and/or corticobasal degeneration.

Further, in another embodiment, it provides use of compound of formula (II) for the treatment of asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, autoimmune diseases. Parkinson's disease, Alzheimer's disease, restless leg syndrome, nocturnal myoclonus, cerebral ischaemia, Huntington's disease, Wilson's disease, multiple system atrophy and/or corticobasal degeneration.

According to an embodiment, the present invention provides use of compound of formula (I) for use in preparation of medicament useful in the treatment of conditions mediated by adenosine receptor.

According to an embodiment, the present invention provides a pharmaceutical composition comprising a therapeutically effective amount of a compound of formula II, or its tautomers, polymorphs, stereoisomers, prodrugs, solvate or a pharmaceutically acceptable salts thereof, for the treatment of asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, autoimmune diseases, Parkinson's disease, Alzheimer's disease, restless leg syndrome, nocturnal myoclonus, cerebral ischaemia, Huntington's disease, Wilson's disease, multiple system atrophy and/or corticobasal degeneration.

According to another embodiment, the present invention provides a pharmaceutical composition comprising a compound of formula II, or its tautomers, polymorphs, stereoisomers, prodrugs, solvate or a pharmaceutically acceptable salts thereof, in combination with one or more pharmaceutically acceptable therapeutically active agent. The pharmaceutically acceptable therapeutically active agent is selected from anti-inflammatory agent, anti-diabetic agent, anti-hypertensive agent, anti-dyslipidemic agent, anticholinergic agent, antimuscarinic agent, steroid, LTB4 (leukotriene B4) antagonist, dopamine receptor agonists, phosphodiesterase 4 inhibitor, beta-2 adrenergic receptor agonist, insulin, insulin derivatives and mimetics, insulin secretagogues, insulinotropic sulfonylurea receptor ligands, thiazolidone derivatives, glycogen synthase kinase-3 inhibitor, sodium-dependent glucose co-transporter inhibitor, glycogen phosphorylase A inhibitor, biguanide, alpha-glucosidase inhibitor, glucagon like peptide-1 (GLP-1), GLP-1 analogs and GLP-1 mimetics, modulators of peroxisome proliferator-activated receptors, dipeptidyl peptidase IV inhibitor, stearoyl-CoA desaturase-1 inhibitor, diacylglycerol acyltransferase 1 and 2 inhibitor, acetyl CoA carboxylase 2 inhibitor, and breakers of advanced glycation end products, loop diuretics, angiotensin converting enzyme inhibitor, inhibitor of the Na—K-ATPase membrane pump such as digoxin, neutralendopeptidase (NEP) inhibitor, ACE/NEP inhibitors, angiotensin II antagonists, renin inhibitors, β-adrenergic receptor blockers, inotropic agents, calcium channel blockers, aldosterone receptor antagonists, and aldosterone synthase inhibitors, 3-hydroxy-3-methyl-glutaryl coenzyme A reductase inhibitor, HDL increasing compounds such as cholesterol ester transfer protein inhibitor, squalene synthase inhibitor, farnesoid X receptor and liver X receptor ligand, cholestyramine, fibrates, nicotinic acid, or aspirin.

Further, in another embodiment, it provides use of compound of formula (II) for use in preparation of medicament useful in the treatment of asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

EXAMPLES

The invention is further illustrated by the following examples which in no way should be construed as being further limiting. One skilled in the art will readily appreciate that the specific methods and results described are merely illustrative. Structures of the intermediates as well as the final compounds were confirmed by nuclear magnetic resonance spectra for proton ($^1$H NMR) and LCMS.

Example 1

8-(1-Benzyl-1H-pyrazol-4-yl)-1-propyl-1,4,5,7-tetrahydro-purin-6-one

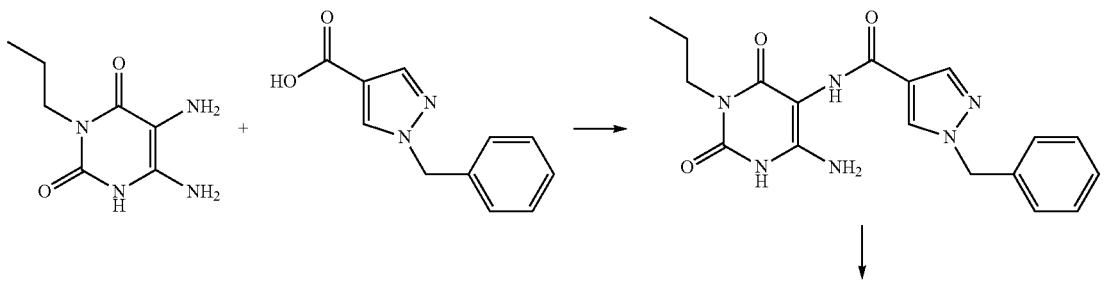

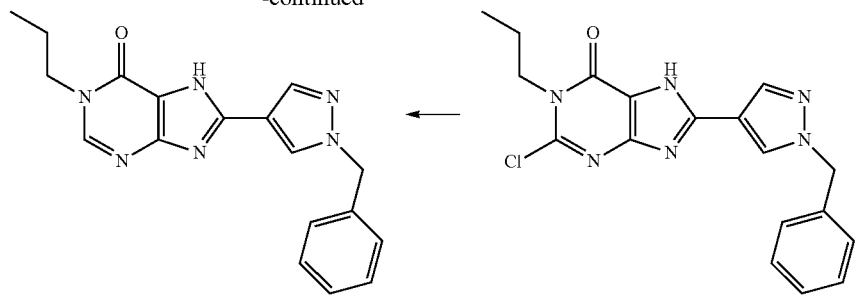

Step 1: 1-Benzyl-1H-pyrazole-4-carboxylic acid (6-amino-2,4-dioxo-3-propyl-1,2,3,4-tetrahydro-pyrimidin-5-yl)-amide A mixture of 5,6-diamino-3-propyl-1H-pyrimidine-2,4-dione (1.6 g, 8.55 mmol), 1-benzyl-1H-pyrazole-4-carboxylic acid (1.75 g, 8.65 mmol) in methanol (10 ml) were cooled to 0° C. and added EDCI.HCl (2.32 g, 12.11 mmol). The reaction mixture was stirred at 25° C. for 20 hours and the solvents were removed under reduced pressure. To this residue water (10 ml) was added and the precipitate was filtered off, and was washed sequentially with cold water (20 ml) and DCM (25 ml) to obtain 1-Benzyl-1H-pyrazole-4-carboxylic acid (6-amino-2,4-dioxo-3-propyl-1,2,3,4-tetrahydro-pyrimidin-5-yl)-amide (1.5 g, 47%) as a pale yellow solid.

$^1$HNMR (400 MHz, DMSO d6): δ 0.82 (t, J=7.6 Hz, 3H); 1.46-1.51 (m, 2H); 3.64 (t, J=7.2 Hz, 2H); 5.36 (s, 2H); 6.01 (s, 2H); 7.26-7.38 (m, 5H); 7.96 (s, 1H); 8.31 (s, 1H); 8.54 (s, 1H); 10.43 (s, 1H).

Step 2: 8-(1-Benzyl-1H-pyrazol-4-yl)-2-chloro-1-propyl-1,7-dihydro-purin-6-one A mixture of 1-benzyl-1H-pyrazole-4-carboxylicacid(6-amino-2,4-dioxo-3-propyl-1,2,3,4-tetrahydro-pyrimidin-5-yl)-amide (0.5 g, 13.5 mmol), POCl$_3$ (10 ml) and DMF (0.1 ml) were heated at 125-130° C. for 20 hours. Reaction mixture was cooled to 20-25° C. It was then concentrated under vacuum. The residue was triturated with diethyl ether, dried. The crude product was purified by column chromatography using silica gel (100-200 mesh) and 2 to 4% methanol in DCM as an eluent to obtain 8-(1-Benzyl-1H-pyrazol-4-yl)-2-chloro-1-propyl-1,7-dihydro-purin-6-one (0.04 g, 8%) as a pale brown solid.

$^1$HNMR (400 MHz, DMSO d6): δ 0.93 (t, J=7.6 Hz, 3H); 1.67-1.73 (m, 2H); 4.15 (t, J=7.6 Hz, 2H); 5.42 (s, 2H); 7.29-7.39 (m, 5H); 8.14 (s, 1H); 8.49 (s, 1H); 13.68 (bs, 1H).

Step 3: 8-(1-Benzyl-1H-pyrazol-4-yl)-1-propyl-1,7-dihydro-purin-6-one

A mixture of 8-(1-benzyl-1H-pyrazol-4-yl)-2-chloro-1-propyl-1,7-dihydro-purin-6-one (0.035 g, 0.094 mmol), Pd\C (10%) (0.025 g), in ethanol (20 ml) were stirred under hydrogen atmosphere for 20 hours. Reaction mixture was filtered through celite bed washed with methanol (20 ml), and the solvents were removed under vacuum. The crude product was purified by column chromatography using silica gel (100-200 mesh) and 2 to 4% methanol in DCM as an eluent to obtain 8-(1-Benzyl-1H-pyrazol-4-yl)-1-propyl-1,7-dihydro-purin-6-one (0.012 g, 39%) as off white solid.

$^1$HNMR (400 MHz, DMSO d6): δ 0.89 (t, J=7.2 Hz, 3H); 1.66-1.72 (m, 2H); 3.94 (t, J=7.6 Hz, 2H); 5.41 (s, 2H); 7.302-7.38 (m, 5H); 8.03 (s, 1H); 8.16 (s, 1H); 8.34 (s, 1H).

Example 2

2-Chloro-8-[1-(3-fluoro-4-trifluoromethyl-benzyl)-1H-pyrazol-4-yl]-1-propyl-1,7-dihydro-purin-6-one

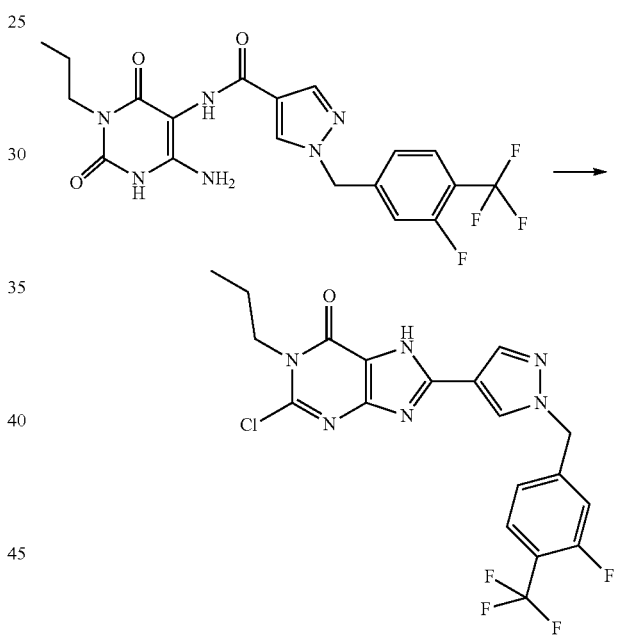

A mixture of 1-(3-fluoro-4-trifluoromethyl-benzyl)-1H-pyrazole-4-carboxylic acid (6-amino-2,4-dioxo-3-propyl-1,2,3,4-tetrahydro-pyrimidin-5-yl)-amide (0.8 g, 1.76 mmol), POCl$_3$ (25 ml) and PCl$_5$ (0.2 g) were heated at 125-130° C. for 20 hours. Reaction mixture was cooled to 20-25° C. and it was concentrated under vacuum. To this reaction mixture brine (50 ml) was added and extracted with ethyl acetate (3×2 ml). The combined organic layer was dried over Na$_2$SO$_4$ and evaporated to dryness. The crude product was purified by column chromatography using silica gel (100-200 mesh) and 2 to 4% methanol in DCM as an eluent to obtain 2-Chloro-8-[1-(3-fluoro-4-trifluoromethyl-benzyl)-1H-pyrazol-4-yl]-1-propyl-1,7-dihydro-purin-6-one (0.4 g, 50%) as a pale brown solid.

$^1$HNMR (400 MHz, CD$_3$OD): δ 1.05 (t, J=7.2 Hz, 3H); 1.83-1.85 (m, 2H); 4.31 (t, J=5.6 Hz, 2H); 5.57 (s, 2H); 7.26-7.29 (m, 2H); 7.70-7.74 (m, 1H); 8.16 (s, 1H); 8.40 (s, 1H).

Examples 3-7 were prepared in an analogous manner of Example 2 from appropriate intermediates.

| Example | IUPAC name |
|---|---|
| 3 | 2-Chloro-1-propyl-8-[1-(3-trifluoromethyl-benzyl)-1H-pyrazol-4-yl]-1,7-dihydro-purin-6-one |
| 4 | 2-Chloro-8-[1-(3-fluoro-benzyl)-1H-pyrazol-4-yl]-1-propyl-1,7-dihydro-purin-6-one |
| 5 | 2-Chloro-8-[1-(2,4-difluoro-benzyl)-1H-pyrazol-4-yl]-1-propyl-1,7-dihydro-purin-6-one |
| 6 | 2-Chloro-8-[1-(2,3-difluoro-benzyl)-1H-pyrazol-4-yl]-1-propyl-1,7-dihydro-purin-6-one |
| 7 | 2-Chloro-1-propyl-8-[1-(4-trifluoromethyl-benzyl)-1H-pyrazol-4-yl]-1,7-dihydro-purin-6-one |

Example 8

8-[1-(2,3-difluoro-benzyl)-1H-pyrazol-4-yl]-1-propyl-1,7-dihydro-purin-6-one

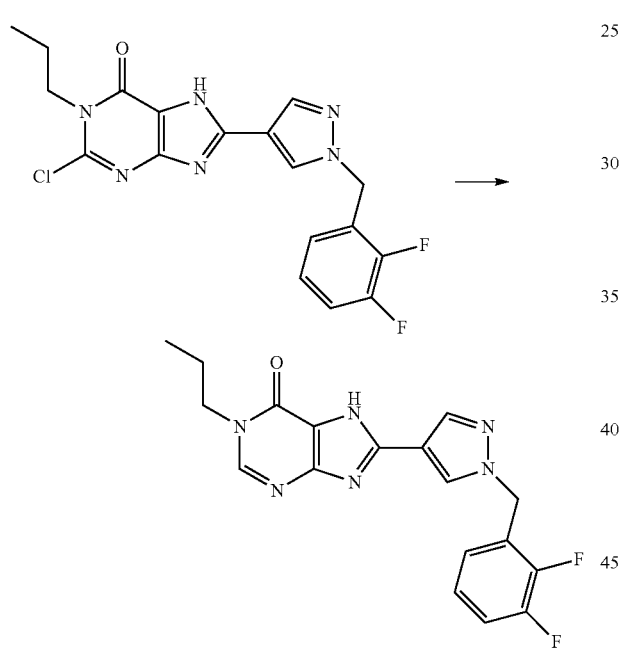

A mixture of 2-Chloro-8-[1-(2,3-difluoro-benzyl)-1H-pyrazol-4-yl]-1-propyl-1,7-dihydro-purin-6-one (0.04 g, 0.09 mmol), ammonium formate (0.134 g, 1.97 mmol), Pd\C (10%) (0.02 g), DMF (2 ml) and H₂O (0.5 ml) were heated at 85-90° C. for 15 hours. Reaction mixture was cooled to 20-25° C. and then it was filtered through celite bed washed with methanol (10 ml). The filtrate was concentrated under vacuum. To this residue water (1 ml) was added and acidified with citric acid up to pH (1-2). Solid precipitated was filtered off and washed sequentially with cold water, diethyl ether to obtain pure 8-[1-(2,3-difluoro-benzyl)-1H-pyrazol-4-yl]-1-propyl-1,7-dihydro-purin-6-one (0.01 g, 28%) as a off white solid.

¹HNMR (400 MHz, CD₃OD): δ 0.98 (t, J=7.2 Hz, 3H); 1.78-1.84 (m, 2H); 4.06 (t, J=6.8 Hz, 2H); 5.54 (s, 2H); 7.08-7.11 (m, 1H); 7.15-7.18 (m, 1H); 7.26-7.29 (m, 1H); 8.11 (s, 1H); 8.25 (s, 1H); 8.35 (s, 1H).

Examples 9-13 were prepared in an analogous manner of Example 8 from appropriate intermediates.

| Example | IUPAC name |
|---|---|
| 9 | 8-[1-(3-Fluoro-benzyl)-1H-pyrazol-4-yl]-1-propyl-1,7-dihydro-purin-6-one, |
| 10 | 8-[1-(2,4-Difluoro-benzyl)-1H-pyrazol-4-yl]-1-propyl-1,7-dihydro-purin-6-one |
| 11 | 1-Propyl-8-[1-(3-trifluoromethyl-benzyl)-1H-pyrazol-4-yl]-1,7-dihydro-purin-6-one |
| 12 | 1-Propyl-8-[1-(4-trifluoromethyl-benzyl)-1H-pyrazol-4-yl]-1,7-dihydro-purin-6-one |
| 13 | 8-[1-(3-fluoro-4-trifluoromethyl-benzyl)-1H-pyrazol-4-yl]-1-propyl-1,7-dihydro-purin-6-one |

Example 14

1-Propyl-8-(1H-pyrazol-4-yl)-1,7-dihydro-purin-6-one

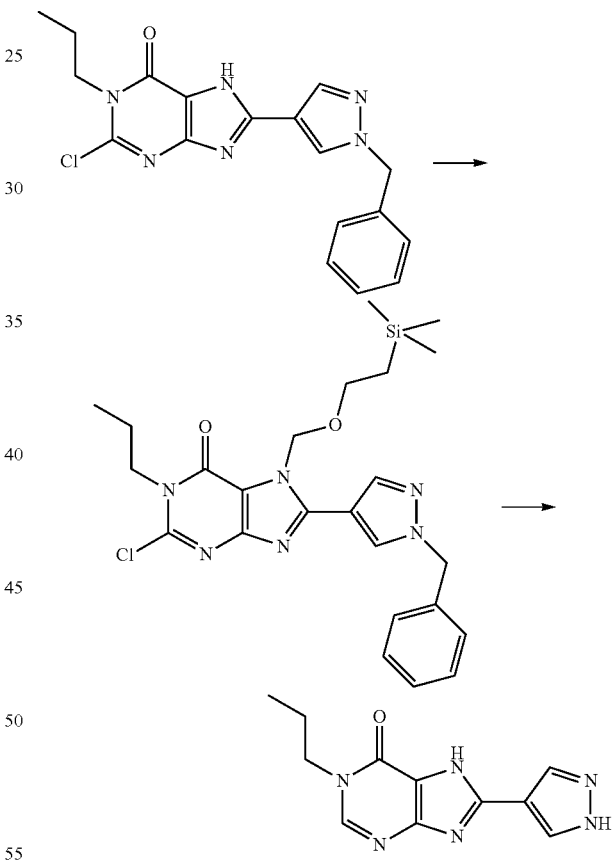

Step 1: 8-(1-Benzyl-1H-pyrazol-4-yl)-2-chloro-1-propyl-7-(2-trimethylsilanyl-ethoxymethyl)-1,7-dihydro-purin-6-one A mixture of 8-(1-benzyl-1H-pyrazol-4-yl)-2-chloro-1-propyl-1,7-dihydro-purin-6-one (0.9 g, 2.44 mmol), K₂CO₃ (1.01 g, 7.32 mmol) in DMF (10 ml) were cooled to 0° C. and added SEM-Cl (1.3 ml, 7.32 mmol). The reaction mixture was stirred at 25° C. for 20 hours. To this reaction mixture water (100 ml) was added and extracted with ethyl acetate (3×30 ml). The combined organic layer was washed with brine (30 ml) and dried over Na$_2$SO$_4$. The organic layer was evaporated to dryness and the crude product was purified by column chromatography using silica gel (100-200 mesh) and 10-15% ethyl acetate in hexane as an eluent to obtain 8-(1-Benzyl-1H-pyrazol-4-yl)-2-chloro-1-propyl-7-(2-trimethyl-silanyl-ethoxymethyl)-1,7-dihydro-purin-6-one (0.3 g, 25%) as a off white solid.

$^1$HNMR (400 MHz, CDCl$_3$): δ −0.01 (s, 9H); 0.94 (t, J=8.4 Hz, 3H); 1.04 (t, J=7.6 Hz, 2H); 1.79-1.85 (m, 2H); 3.77 (t, J=8.0 Hz, 2H); 4.28 (t, J=7.6 Hz, 2H); 5.40 (s, 2H); 5.86 (s, 2H); 7.31-7.41 (m, 5H); 8.28 (s, 1H); 8.35 (s, 1H).

Step 2: 1-Propyl-8-(1H-pyrazol-4-yl)-1,7-dihydro-purin-6-one

A mixture of 8-(1-Benzyl-1H-pyrazol-4-yl)-2-chloro-1-propyl-7-(2-trimethylsilanyl-ethoxymethyl)-1,7-dihydro-purin-6-one (0.1 g, 0.201 mmol), Pd (OH)$_2$ (20%) (0.2 g), in ethanol (4 ml) and cyclohexene were stirred under nitrogen balloon for 25 hrs. Reaction mixture was filtered through celite bed washed with methanol (20 ml). The filtrate was concentrated under vacuum and the crude product was purified by column chromatography using silica gel (100-200 mesh) and 5 to 6% methanol in DCM as an eluent to obtain 1-propyl-8-(1H-pyrazol-4-yl)-1,7-dihydro-purin-6-one (0.018 g, 24%) as white solid.

$^1$HNMR (400 MHz, CD$_3$OD): δ 1.02 (t, J=7.2 Hz, 3H); 1.82-1.88 (m, 2H); 4.10 (t, J=7.6 Hz, 2H); 8.20 (bs, 1H); 8.29 (bs, 1H); 8.36 (bs, 1H).

Example 15

8-(4-Hydroxy-phenyl)-1-propyl-1,7-dihydro-purin-6-one

Preparation of 4-benzyloxy-benzoic acid methyl ester

A mixture of methyl 4-hydroxy-benzoate (10.0 g, 0.066 mol) and potassium carbonate (12 g, 0.086 mol), were taken in acetone (50 ml) and heated at 50° C. for 1 hour. To the reaction mixture benzyl bromide (8.2 ml, 0.072 mol) was added. The mixture was heated at 80° C. for 5 hours. The mixture was cooled to room temperature and filtered through sintered funnel, washed with acetone. Solvent was removed to obtain pure 4-benzyloxy-benzoic acid methyl ester as white solid (16 g, 100%).

$^1$HNMR (400 MHz, CDCl$_3$): δ 3.85 (s, 3H); 5.17 (s, 2H); 6.99 (d, J=8.8 Hz, 2H); 7.38-7.42 (m, 5H); 8.00 (d, J=8.8 Hz, 2H)

Preparation of 4-benzyloxy-benzoic acid

The above product (19.0 g, 0.074 mol) was dissolved in a mixture of solvents THF:methanol:water (3:2:1, 250 ml) and NaOH (5.9 gm, 0.15 mol) was added to the reaction mixture and stirred at 50-55° C. for 3 hours. Solvents were removed and the residue was diluted with water (20 ml), washed with hexane (2×50 ml) and acidified with dil. HCl to obtain white precipitate, 4-benzyloxy-benzoic acid (15 g, 89%).

$^1$HNMR (400 MHz, CDCl$_3$): δ 5.14 (s, 2H); 7.02 (d, J=8.8 Hz, 2H); 7.4-7.42 (m, 5H); 8.05 (d, J=8.8 Hz, 2H).

Step 1: N-(6-Amino-2,4-dioxo-3-propyl-1,2,3,4-tetrahydro-pyrimidin-5-yl)-4-benzyloxy-benzamide A mixture of 4-benzyloxy-benzoic acid (7.44 g, 0.033 mol), 5,6-diamino-3-propyl-1H-pyrimidine-2,4-dione (5.0 g, 0.027 mol), methanol (60 ml), EDCI (10.0 g, 0.052 mol), were taken and stirred for 20 hours at 20-25° C. The reaction

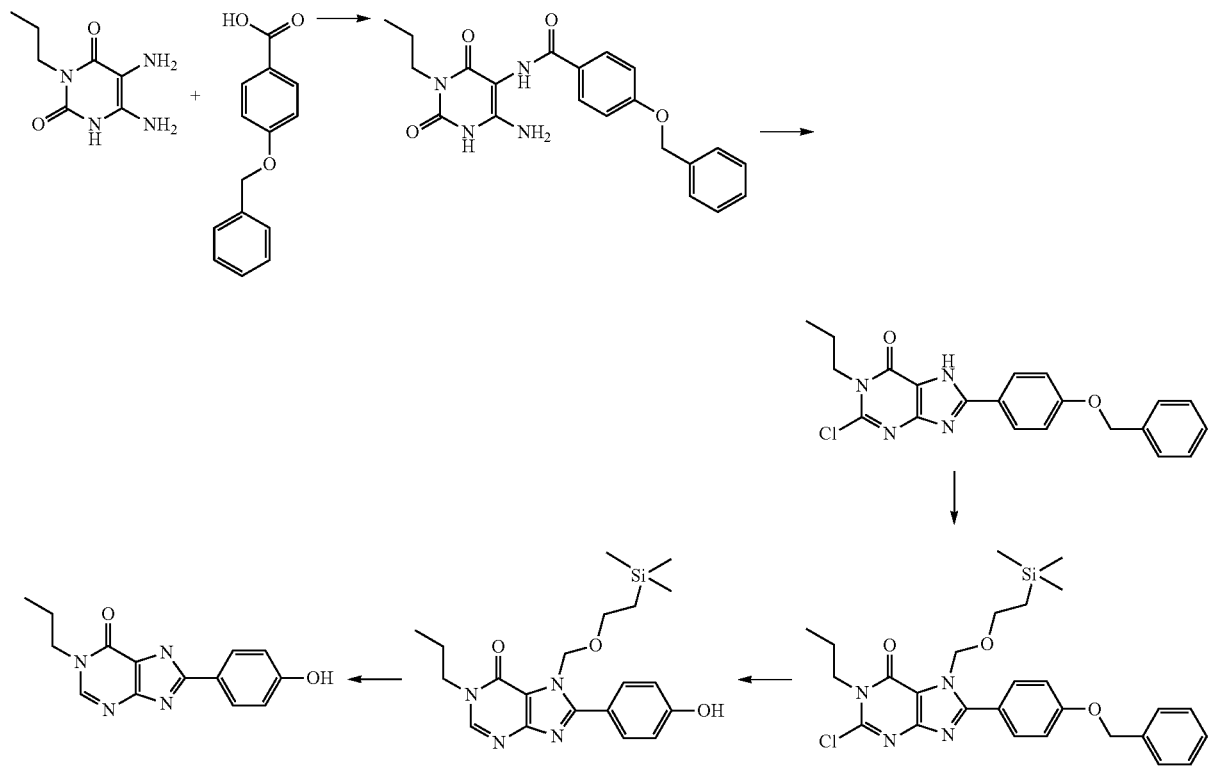

mixture was concentrated and water (50 ml) was added to obtain solid precipitate. The compound was purified by column chromatography to obtain N-(6-Amino-2,4-dioxo-3-propyl-1,2,3,4-tetrahydro-pyrimidin-5-yl)-4-benzyloxy-benzamide as light yellow solid (4.0 g, 38%).

$^1$HNMR (400 MHz, DMSO d6): δ 0.82-0.90 (m, 3H); 1.47-1.49 (m, 2H); 3.65 (t, J=6.8 Hz, 2H); 5.19 (s, 2H); 6.04 (s, 2H); 7.08 (d, J=8.4 Hz, 2H); 7.32-7.48 (m, 5H); 7.93 (d, J=8.4 Hz, 2H); 8.75 (s, 1H); 10.44 (s, 1H).

Step 2: 8-(4-Benzyloxy-phenyl)-2-chloro-1-propyl-1,7-dihydro-purin-6-one

The above N-(6-amino-2,4-dioxo-3-propyl-1,2,3,4-tetrahydro-pyrimidin-5-yl)-4-benzyloxy-benzamide (1.0 g, 0.0025 mol) and phosphorous pentachloride (0.64 g, 0.0025 mol) were taken in phosphorous oxy chloride (25 ml) and refluxed for 20 hours The mixture was cooled and solvent was removed. The residue was dissolved in water (20 ml) and extracted with DCM. (3×5 ml). The organic layer was washed with sat. NaHCO$_3$ (30 ml) followed by saturated brine solution (2×30 ml) and dried over Na$_2$SO$_4$. Solvent was removed and the residue was further purified by column chromatography to obtain pure 8-(4-benzyloxy-phenyl)-2-chloro-1-propyl-1,7-dihydro-purin-6-one (0.298 g, 30%) as a yellow solid.

$^1$HNMR (400 MHz, DMSO d6): δ 0.82-0.90 (m, 3H); 1.47-1.49 (m, 2H); 3.65 (t, J=6.8 Hz, 2H); 5.19 (s, 2H); 6.04 (s, 2H); 7.08 (d, J=8.4 Hz, 2H); 7.32-7.48 (m, 5H); 7.93 (d, J=8.4 Hz, 2H); 8.75 (s, 1H); 10.44 (s, 1H).

Step 3: 8-(4-Benzyloxy-phenyl)-2-chloro-1-propyl-7-(2-trimethylsilanyl-ethoxymethyl)-1,7-dihydro-purin-6-one A mixture of 8-(4-benzyloxy-phenyl)-2-chloro-1-propyl-1,7-dihydro-purin-6-one (0.298 g, 0.00075 mol) and potassium carbonate (0.311 g, 0.0023 mol), were taken in DMF (2 ml) and 2-(trimethylsilyl)ethoxymethyl chloride (0.4 ml, 0.0023 mol) was added drop wise at 0° C. and the mixture was stirred at 20° C. for 4 hours. The mixture was cooled to 10° C. and diluted with water (10 ml). The aqueous layer was extracted with ethyl acetate (2×10 ml). The organic layer was washed with saturated brine solution (2×15 ml) and dried over Na$_2$SO$_4$. Solvent was removed and the residue was further purified by column chromatography to obtain pure 8-(4-benzyloxy-phenyl)-2-chloro-1-propyl-7-(2-trimethylsilanyl-ethoxymethyl)-1,7-dihydro-purin-6-one (0.278 g, 70%) as off white solid.

$^1$HNMR (400 MHz, DMSO d6): δ −0.01 (s, 9H); 0.84-0.86 (m, 2H); 0.93 (t, J=7.6 Hz, 3H); 1.67-1.71 (m, 2H); 3.67 (t, J=8 Hz, 2H); 4.18 (t, J=7.6 Hz, 2H); 5.21 (s, 2H); 5.73 (s, 2H); 7.21 (d, J=8.8 Hz, 2H); 7.34-7.42 (m, 5H); 7.92 (d, J=8.8 Hz, 2H)

Step 4: 8-(4-Hydroxy-phenyl)-1-propyl-7-(2-trimethylsilanyl-ethoxymethyl)-1,7-dihydro-purin-6-one To a solution of 8-(4-benzyloxy-phenyl)-2-chloro-1-propyl-7-(2-trimethylsilanyl-ethoxymethyl)-1,7-dihydro-purin-6-one (0.25 g, 0.00048 mol) in DMF:water (2.5 ml), 10% Pd/C (0.130 g) and ammonium formate (0.66 g, 0.010 mol) were added and refluxed at 80° C. for 2 hours. The mixture was cooled and filtered through celite bed, solvent was removed and the residue was diluted with water (10 ml), acidified with citric acid and extracted with ethyl acetate (3×10 ml). The organic layer was washed with brine (2×15 ml). It was dried over Na$_2$SO$_4$ and the solvent was removed to obtain pale yellow solid of 8-(4-hydroxy-phenyl)-1-propyl-7-(2-trimethylsilanyl-ethoxymethyl)-1,7-dihydro-purin-6-one (0.153 g, 80%).

$^1$HNMR (400 MHz, DMSO d6): δ −0.01 (s, 9H); 0.83-0.90 (m, 5H); 1.68-1.74 (m, 2H); 3.68 (t, J=7.6 Hz, 2H); 3.99 (t, J=6.4 Hz, 2H); 5.76 (s, 2H); 6.93 (d, J=8.8 Hz, 2H); 7.82 (d, J=8.8 Hz, 2H); 8.38 (s, 1H); 10.1 (s, 1H).

Step 5: 8-(4-Hydroxy-phenyl)-1-propyl-1,7-dihydro-purin-6-one

A mixture of 8-(4-hydroxy-phenyl)-1-propyl-7-(2-trimethylsilanyl-ethoxymethyl)-1,7-dihydro-purin-6-one (0.03 g, 0.075 mmol), 2N HCl (1 ml), ethanol (2 ml) was heated at 85° C. for 2 hours. The mixture was cooled and the solvent was evaporated. The residue was washed with n-pentane to obtain 8-(4-Hydroxy-phenyl)-1-propyl-1,7-dihydro-purin-6-one (0.019 g, 95%) as a yellow solid.

$^1$HNMR (400 MHz, DMSO d6): δ 0.91 (t, J=7.2 Hz, 3H); 1.70-1.72 (m, 2H); 3.98 (t, J=7.2 Hz, 2H); 6.91 (d, J=8.4 Hz, 2H); 8.01 (d, J=8.4 Hz, 2H); 8.33 (s, 1H); 10.1 (bs, 1H).

Example 16

8-{4-[3-(4-Fluoro-phenyl)-prop-2-ynyloxy]-phenyl}-1-propyl-1,7-dihydro-purin-6-one

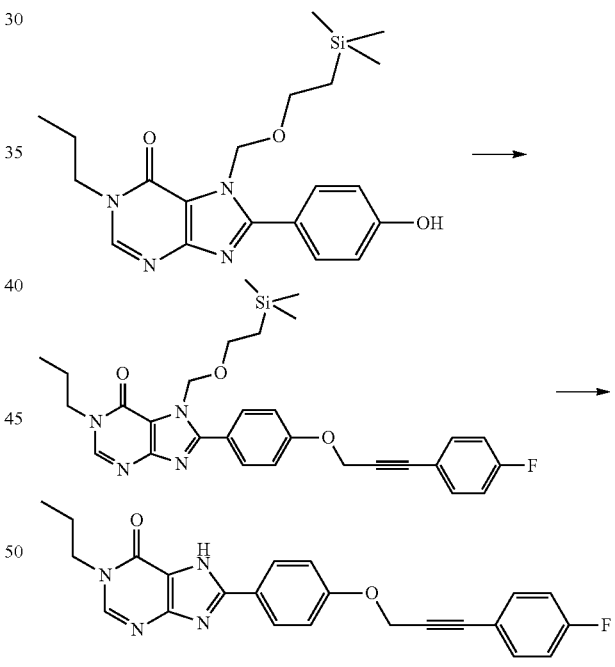

Step 1: 8-{4-[3-(4-Fluoro-phenyl)-prop-2-ynyloxy]-phenyl}-1-propyl-7-(2-trimethylsilanyl-ethoxymethyl)-1,7-dihydro-purin-6-one A mixture of 8-(4-hydroxy-phenyl)-1-propyl-7-(2-trimethylsilanyl-ethoxymethyl)-1,7-dihydro-purin-6-one (0.100 g, 0.25 mmol), potassium carbonate (0.086 g, 0.50 mmol), 1-(3-bromo-prop-1-ynyl)-4-fluoro-benzene (0.107 g, 0.50 mmol) were taken in acetone (10 ml).

The reaction mixture was heated at 80° C. for 2 hour. The mixture was cooled to room temperature and filtered through sintered funnel, washed with acetone. Solvent was evaporated and the residue was purified by preparative TLC to obtain pure 8-{4-[3-(4-fluoro-phenyl)-prop-2-ynyloxy]-phenyl}-1-propyl-7-(2-trimethylsilanyl-ethoxymethyl)-1,7-dihydro-purin-6-one (0.033 g, 25%) as pale yellow solid.

Step 2: 8-{4-[3-(4-Fluoro-phenyl)-prop-2-ynyloxy]-phenyl}-1-propyl-1,7-dihydro-purin-6-one A mixture of 8-{4-[3-(4-Fluoro-phenyl)-prop-2-ynyloxy]-phenyl}-1-propyl-7-(2-trimethylsilanyl-ethoxymethyl)-1,7-dihydro-purin-6-one (0.03 g, 0.056 mmol), 2N HCl (1 ml), ethanol (2 ml) was heated at 85° C. for 2 hours. The mixture was cooled and the solvent was evaporated. The residue was washed with n-pentane to obtain 8-{4-[3-(4-fluoro-phenyl)-prop-2-ynyloxy]-phenyl}-1-propyl-1,7-dihydro-purin-6-one (0.018 g, 78%) as off white solid.

$^1$HNMR (400 MHz, DMSO d6): δ 0.88 (t, J=7.2 Hz, 3H); 1.69-1.70 (m, 2H); 3.97 (t, J=7.2 Hz, 2H); 5.12 (s, 2H); 7.17-7.25 (m, 4H); 7.50-7.54 (m, 2H); 8.12 (d, J=8.8 Hz, 2H); 8.32 (s, 1H);

Examples 17-20 were prepared in an analogous manner of Example 16 from appropriate intermediates.

| Example | IUPAC name |
|---------|------------|
| 17 | 1-Propyl-8-{4-[3-(3-trifluoromethyl-phenyl)-prop-2-ynyloxy]-phenyl}-1,7-dihydro-purin-6-one |
| 18 | 8-{4-[5-Oxo-1-(4-trifluoromethoxy-phenyl)-pyrrolidin-3-ylmethoxy]-phenyl}-1-propyl-1,7-dihydro-purin-6-one |
| 19 | 8-{4-[5-Oxo-1-(3-trifluoromethyl-phenyl)-pyrrolidin-3-ylmethoxy]-phenyl}-1-propyl-1,7-dihydro-purin-6-one |
| 20 | [4-(6-Oxo-1-propyl-6,7-dihydro-1H-purin-8-yl)-phenoxy]-acetic acidethyl ester |

Example 21

N-(4-Cyano-phenyl)-2-[4-(6-oxo-1-propyl-6,7-dihydro-1H-purin-8-yl)-phenoxy]-acetamide

Step 1: 2-Chloro-N-(4-cyano-phenyl)-acetamide

A mixture of 4-Amino benzonitrile (1.0 g, 0.0084 mol) and triethyl amine (1 ml, 0.010 mol) was taken in DCM (15 ml). Chloro acetyl chloride (0.67 ml, 0.0084 mol) was added slowly and stirred for 22 hours at 25-27° C. Solvent was removed and the residue was dissolved in ethyl acetate (20 ml), washed with water (1×15 ml) followed by brine (2×15 ml). The organic layer was dried over Na$_2$SO$_4$ and the solvent was removed to get pure 2-chloro-N-(4-cyano-phenyl)-acetamide (1.51 g, 92%).

$^1$HNMR (400 MHz, CDCl$_3$): δ 4.22 (s, 2H); 7.66 (d, J=8.4 Hz, 2H); 7.71 (d, J=8.4 Hz, 2H); 8.38 (bs, 1H).

Step 2: N-(4-Cyano-phenyl)-2-{4-[6-oxo-1-propyl-7-(2-trimethylsilanyl-ethoxymethyl)-6,7-dihydro-1H-purin-8-yl]-phenoxy}-acetamide A mixture of 8-(4-hydroxy-phenyl)-1-propyl-7-(2-trimethylsilanyl-ethoxymethyl)-1,7-dihydro-purin-6-one (0.100 g, 0.25 mmol), potassium carbonate (0.052 g, 0.38 mmol), and 2-chloro-N-(4-cyano-phenyl)-acetamide (0.053 g, 0.28 mmol) in acetone (10 ml) was heated at 80° C. for 2 hours. The mixture was cooled to room temperature and filtered through sintered funnel, washed with acetone. The solvent was evaporated and the residue was purified by preparative TLC to obtain pure pale yellow solid of N-(4-cyano-phenyl)-2-{4-[6-oxo-1-propyl-7-(2-trimethylsilanyl-ethoxymethyl)-6,7-dihydro-1H-purin-8-yl]-phenoxy}-acetamide (0.110 g, 79%) as a off white solid.

Step 3: N-(4-cyano-phenyl)-2-[4-(6-oxo-1-propyl-6,7-dihydro-1H-purin-8-yl)-phenoxy]-acetamide The above compound N-(4-Cyano-phenyl)-2-{4-[6-oxo-1-propyl-7-(2-trimethylsilanyl-ethoxymethyl)-6,7-dihydro-1H-purin-8-yl]-phenoxy}-acetamide (0.110 g, 0.20 mmol) was taken in DCM (6 ml) and TFA (3 ml), stirred for 4 hrs. at 27° C. The solvent was evaporated and the residue was

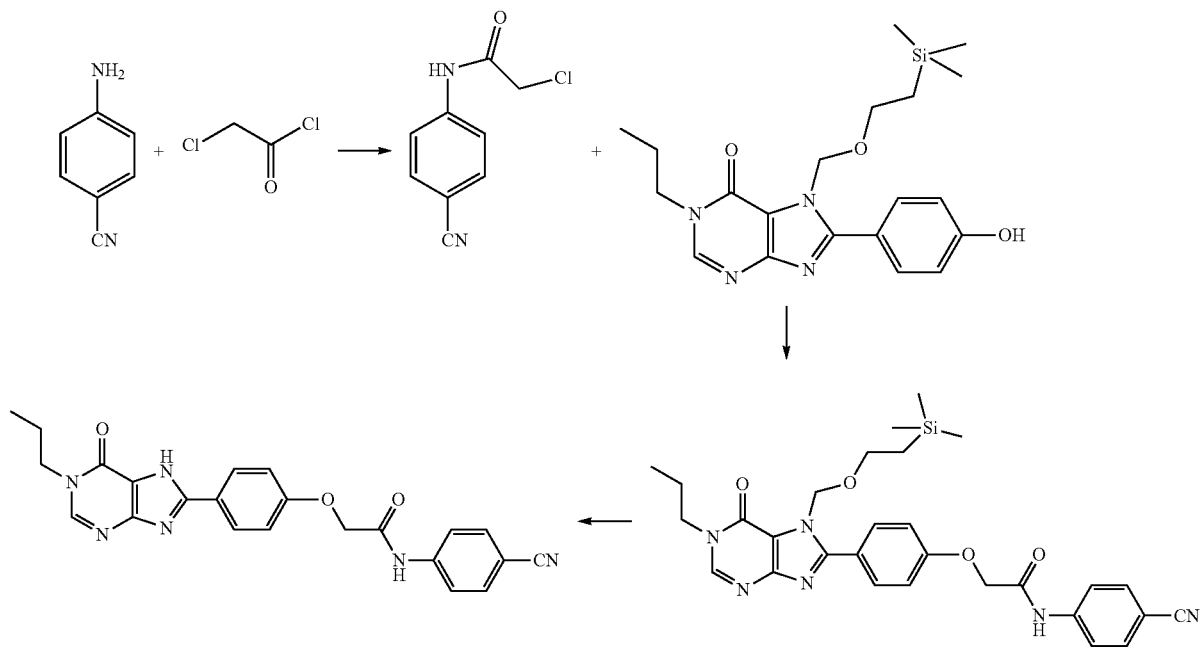

washed with saturated NaHCO₃ followed by water and n-pentane to obtain N-(4-cyano-phenyl)-2-[4-(6-oxo-1-propyl-6,7-dihydro-1H-purin-8-yl)-phenoxy]-acetamide (0.049 g, 58%).

¹HNMR (400 MHz, DMSO d6): δ 0.89 (t, J=7.2 Hz, 3H); 1.68-1.74 (m, 2H); 3.98 (t, J=7.2 Hz, 2H); 4.86 (s, 2H); 7.14 (d, J=8.8 Hz, 2H); 7.80-7.86 (m, 4H); 8.15-8.28 (m, 2H); 8.31 (s, 1H); 10.58 (s, 1H); 13.58 (bs, 1H).

Similarly, the following compound Example 22 has been made:

Example 22

8-[4-[2-oxo-2-[4-[3-(trifluoromethyl)phenyl]piperazin-1-yl]ethoxy]phenyl]-1-propyl-7H-purin-6-one Example 23

1-Propyl-8-thiophen-2-yl-1,7-dihydro-purin-6-one

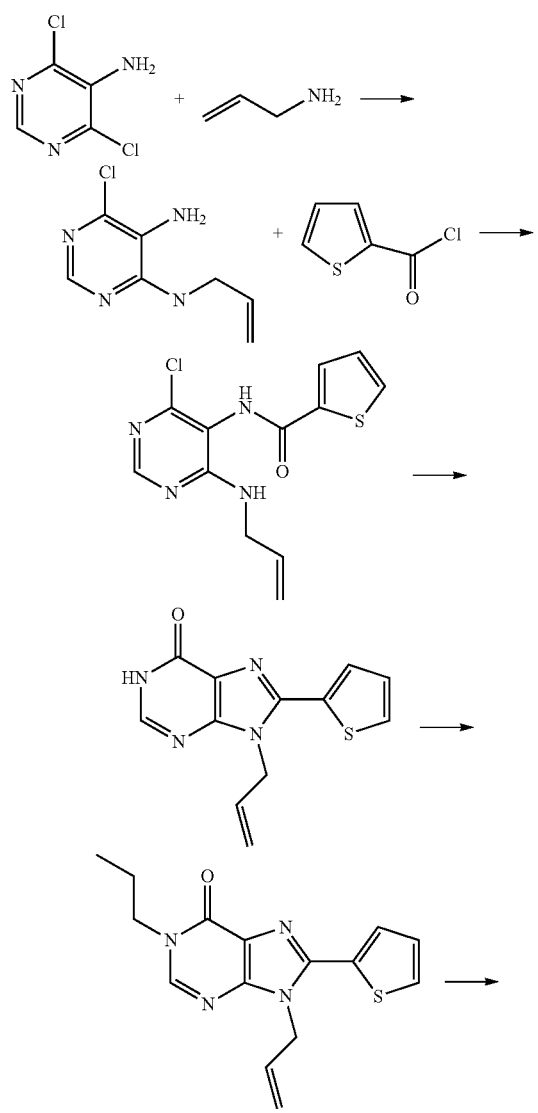

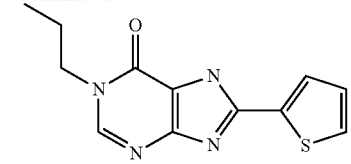

Step 1: N*4*-Allyl-6-chloro-pyrimidine-4,5-diamine

A mixture of 5-amino-4,6-dichloro pyrimidine (3.0 g, 0.018 mol) and allyl amine (1.5 ml, 0.020 mol) was taken in ethanol (30 ml) and heated at 80° C. for 16 hrs. Solvent was removed to get crude product which was further purified by column chromatography to get pure N*4*-Allyl-6-chloro-pyrimidine-4,5-diamine as off white solid (2.30 g, 68%).

¹HNMR (400 MHz, CDCl₃): δ 4.16-4.18 (m, 2H); 5.19-5.30 (m, 2H); 5.39 (s, 1H); 5.95-6.02 (m, 1H); 8.10 (s, 1H)

Step 2: Thiophene-2-carboxylic acid (4-allylamino-6-chloro-pyrimidin-5-yl)-amide N*4*-Allyl-6-chloro-pyrimidine-4,5-diamine (0.20 g, 0.0011 mol) was taken in NMP (3 ml). Thiophene-2-carbonyl chloride (0.14 ml, 0.0013 mol) was added slowly at 0° C. and stirred for 2 hrs at same temperature. The reaction mixture was diluted with water (10 ml) and extracted with DCM (3×5 ml). The organic layer was washed with saturated NaHCO₃ solution (10 ml), followed by brine (10 ml) and dried over Na₂SO₄. The solvent was removed to get thiophene-2-carboxylic acid (4-allylamino-6-chloro-pyrimidin-5-yl)-amide (0.281 g, 88%) as a pale yellow solid.

Step 3: 9-Allyl-8-thiophen-2-yl-1,9-dihydro-purin-6-one

The above compound (0.281 g, 0.95 mmol) was taken in a mixture of isopropanol (5 ml) and sulfuric acid (1 ml) and refluxed for 22 hours at 110° C. Solvent was removed and the residue was diluted with water (2 ml), and basified with Na₂CO₃. The aqueous layer was extracted with CHCl₃ (3×5 ml). The organic layer was washed with brine (10 ml), dried over Na₂SO₄. The solvent was evaporated and the crude product was purified by preparative TLC to get 9-Allyl-8-thiophen-2-yl-1,9-dihydro-purin-6-one (0.100 g, 41%).

Step 4: 9-Allyl-1-propyl-8-thiophen-2-yl-1,9-dihydro-purin-6-one

A mixture of 9-Allyl-8-thiophen-2-yl-1,9-dihydro-purin-6-one (0.100 g, 0.39 mmol), n-propyl iodide (0.04 ml, 0.4 mmol) and Cs₂CO₃ (0.192 g, 0.59 mmol) were taken in DMF (1 ml) and stirred for 20 hours at 27° C. The reaction mixture was diluted with water (5 ml) and extracted with ethyl acetate (3×10 ml). The organic layer was washed with brine (2×15 ml), dried over Na₂SO₄. Solvent was removed to get 9-allyl-1-propyl-8-thiophen-2-yl-1,9-dihydro-purin-6-one (0.100 g, 86%).

Step 5: 1-Propyl-8-thiophen-2-yl-1,7-dihydro-purin-6-one

The above compound, 9-allyl-1-propyl-8-thiophen-2-yl-1,9-dihydro-purin-6-one (0.100 g, 0.33 mmol) and Wilkinson's catalyst were taken in acetonitrile:water (6:1, 7 ml) and refluxed for 5 h at 100° C. Solvent was removed and further purified by preparative TLC to get pure 1-propyl-8-thiophen-2-yl-1,7-dihydro-purin-6-one (9 mg, 10%).

¹HNMR (400 MHz, DMSO d6): δ 0.79-0.86 (m, 3H); 1.63-1.67 (m, 2H); 3.90-3.94 (m, 2H); 7.16-7.18 (m, 1H); 7.65-7.71 (m, 1H); 7.92-7.93 (m, 1H); 8.28-8.31 (m, 1H); 13.23 (bs, 1H)

Example 24

8-(4-Benzyloxy-phenyl)-1-propyl-2-(3-trifluoromethyl-phenyl)-1,7-dihydro-purin-6-one

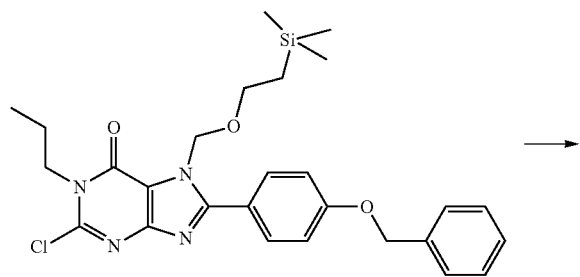

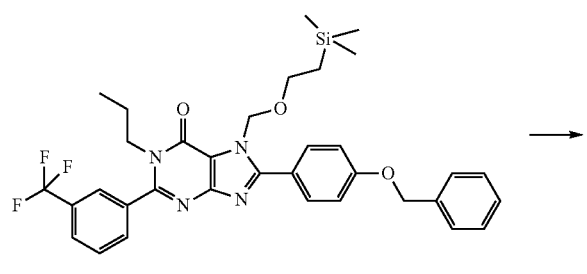

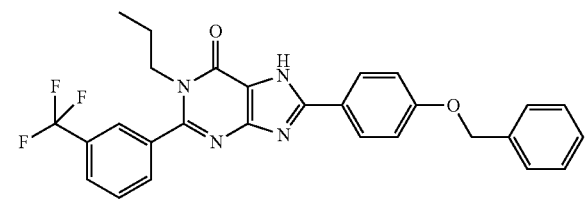

Step 1: 8-(4-Benzyloxy-phenyl)-1-propyl-2-(3-trifluoromethyl-phenyl)-7-(2-trimethylsilanyl-ethoxymethyl)-1,7-dihydro-purin-6-one A mixture of 8-(4-benzyloxy-phenyl)-2-chloro-1-propyl-7-(2-trimethylsilanyl-ethoxymethyl)-1,7-dihydro-purin-6-one (50.0 mg, 0.96 mmol), 3-Trifluoromethyl phenyl boronic acid (31.0 mg, 1.4 mmol) were taken in THF (5 ml) and degassed for 10 minutes. To above degassed solution NaHCO₃ (20.0 mg, 0.24 mmol) in water (1 ml) and Pd(PPh₃)₄ were added and degassed for another 20 minutes. The reaction mixture was stirred for 28 hours at 80-90° C. The mixture was cooled to 25-27° C. and diluted with water (5 ml). The aqueous layer was extracted with DCM (3×5 ml). The organic layer was washed with brine (2×10 ml), dried over Na₂SO₄, and the solvent was evaporated. The residue obtained was purified by preparative TLC (35% Ethyl acetate in hexane) to obtain pure 8-(4-Benzyloxy-phenyl)-1-propyl-2-(3-trifluoromethyl-phenyl)-7-(2-trimethylsilanyl-ethoxymethyl)-1,7-dihydro-purin-6-one (68 mg, quantitative) as a yellow solid.

¹HNMR (400 MHz, DMSO d6): −0.01 (s, 9H); 0.71-0.73 (m, 2H); 0.97-0.99 (m, 3H); 1.57-2.02 (m, 2H); 3.80 (t, J=7.6 Hz, 2H); 3.88-3.91 (m, 2H); 5.28 (s, 2H); 5.88 (s, 2H); 7.29 (d, J=8 Hz, 2H); 7.41-7.50 (m, 3H); 7.55 (d, J=8 Hz, 2H); 7.86-7.89 (m, 2H); 7.98-8.01 (m, 3H); 8.11 (s, 1H)

Step 2: 8-(4-Benzyloxy-phenyl)-1-propyl-2-(3-trifluoromethyl-phenyl)-1,7-dihydro-purin-6-one Step-2 was carried out as described in Step-2 of Example 16

¹HNMR (400 MHz, DMSO d6): 0.66 (t, J=6.8 Hz, 3H); 1.51-1.58 (m, 2H); 3.85 (t, J=6.8 Hz, 2H); 5.2 (s, 2H); 7.19 (d, J=8.4 Hz, 2H); 7.36-7.42 (m, 3H); 7.49 (d, J=6.8 Hz, 2H); 7.81-7.83 (m, 1H); 7.91-7.98 (m, 2H); 8.06 (s, 1H); 8.12 (d, J=7.6 Hz, 2H)

Example 25

8-{4-[3-(4-Fluoro-phenyl)-prop-2-ynyloxy]-phenyl}-1-propyl-2-(3-trifluoromethyl-phenyl)-1,7-dihydro-purin-6-one

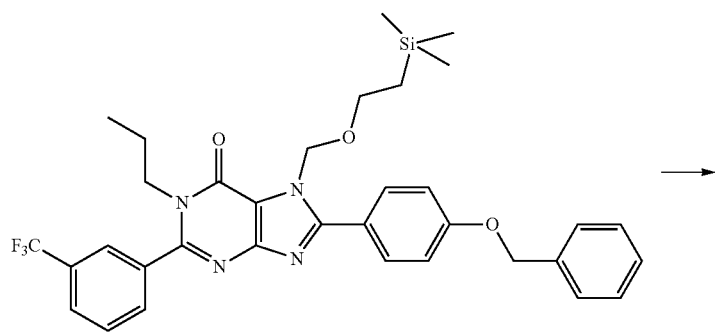

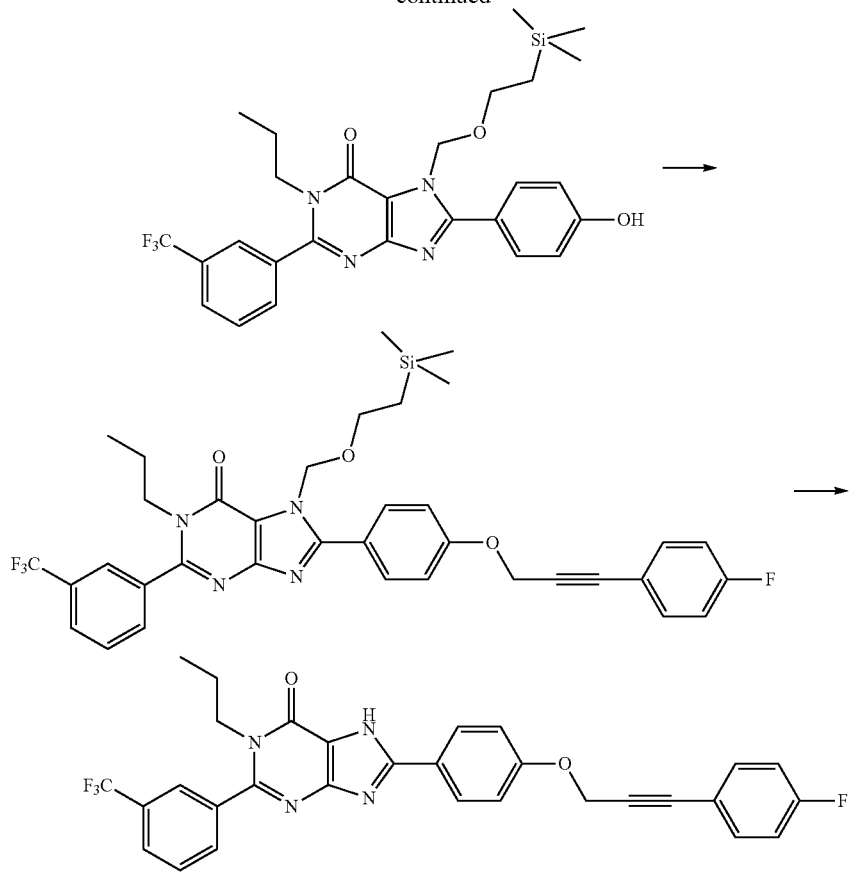

Step 1: 8-(4-Hydroxy-phenyl)-1-propyl-2-(3-trifluoromethyl-phenyl)-7-(2-trimethylsilanyl-ethoxymethyl)-1,7-dihydro-purin-6-one To a solution of 8-(4-Benzyloxy-phenyl)-1-propyl-2-(3-trifluoromethyl-phenyl)-7-(2-trimethylsilanyl-ethoxymethyl)-1,7-dihydro-purin-6-one (0.217 g, 0.24 mmol) in DMF:water (2.5 ml), 10% Pd/C (0.120 g) and ammonium formate (0.431 g, 6.8 mmol) were added and refluxed at 80° C. for 2 hours. The mixture was cooled and filtered through celite bed, solvent was evaporated and the residue was diluted with water (10 ml), acidified with citric acid and extracted with ethyl acetate (3×10 ml). The organic layer was washed with brine (2×15 ml). It was dried over $Na_2SO_4$ and the solvent was evaporated to obtain off white solid of 8-(4-Hydroxy-phenyl)-1-propyl-2-(3-trifluoromethyl-phenyl)-7-(2-trimethylsilanyl-ethoxymethyl)-1,7-dihydro-purin-6-one (0.237 g, quantitative).

$^1$HNMR (400 MHz, DMSO d6): δ −0.01-(−0.015) (s, 9H); 0.64-0.66 (m, 2H); 0.84-0.90 (m, 3H); 1.50-1.52 (m, 2H); 3.72 (t, J=7.6 Hz, 2H); 3.81-3.83 (m, 2H); 5.79 (s, 2H); 6.93 (d, J=8.4 Hz, 2H); 7.81-7.83 (m, 3H); 7.94 (d, J=7.6 Hz, 2H); 8.0 (s, 1H); 10.12 (s, 1H).

Step 2: 8-{4-[3-(4-Fluoro-phenyl)-prop-2-ynyloxy]-phenyl}-1-propyl-2-(3-trifluoromethyl-phenyl)-7-(2-trimethylsilanyl-ethoxymethyl)-1,7-dihydro-purin-6-one A mixture of 8-(4-Hydroxy-phenyl)-1-propyl-2-(3-trifluoromethyl-phenyl)-7-(2-trimethylsilanyl-ethoxymethyl)-1,7-dihydro-purin-6-one (0.115 g, 0.21 mmol), potassium carbonate (0.067 g, 0.48 mmol), 1-(3-bromo-prop-1-ynyl)-4-fluoro-benzene (0.67 g, 0.27 mmol) and acetone (10 ml) was heated at 60° C. for 2 hours. The mixture was cooled to room temperature and filtered through sintered funnel, washed with acetone. Solvent was evaporated and the residue was purified by preparative TLC to obtain pure 8-{4-[3-(4-Fluoro-phenyl)-prop-2-ynyloxy]-phenyl}-1-propyl-2-(3-trifluoromethyl-phenyl)-7-(2-trimethylsilanyl-ethoxymethyl)-1,7-dihydro-purin-6-one (0.061 g, 43%) as pale yellow oil.

$^1$HNMR (400 MHz, DMSO d6): δ −0.015 (s, 9H); 0.72 (t, J=6.8 Hz, 2H); 0.91-0.98 (m, 3H); 1.54-1.60 (m, 2H); 3.80 (t, J=8.4 Hz, 2H); 3.88-3.91 (m, 3H); 5.22 (s, 2H); 5.90 (s, 2H); 7.30-7.33 (m, 4H); 7.58-7.61 (m, 2H); 7.86-7.89 (m, 1H); 8.01-8.05 (m, 4H); 8.11 (s, 1H).

Step 3: 8-{4-[3-(4-Fluoro-phenyl)-prop-2-ynyloxy]-phenyl}-1-propyl-2-(3-trifluoromethyl-phenyl)-1,7-dihydro-purin-6-one A mixture of 8-{4-[3-(4-Fluoro-phenyl)-prop-2-ynyloxy]-phenyl}-1-propyl-2-(3-trifluoromethyl-phenyl)-7-(2-trimethylsilanyl-ethoxymethyl)-1,7-dihydro-purin-6-one (0.056 g, 0.083 mmol), 2N HCl (2 ml), ethanol (2 ml) was heated at 85° C. for 2 hours. The mixture was cooled and the solvent was evaporated. The residue was washed with n-pentane to obtain 8-{4-[3-(4-Fluoro-phenyl)-prop-2-ynyloxy]-phenyl}-1-propyl-2-(3-trifluoromethyl-phenyl)-1,7-dihydro-purin-6-one (0.021 g, 46%) as an off white solid.

$^1$HNMR (400 MHz, DMSO d6): δ −0.16-(−0.96) (m, 3H); 0.72-0.81 (m, 2H); 3.04-3.06 (m, 2H); 4.37 (s, 2H); 6.43-6.47

(m, 4H); 6.75-6.77 (m, 2H); 7.02-7.04 (m, 1H); 7.16-7.18 (m, 2H); 7.27-7.29 (m, 2H); 7.41-7.43 (m, 1H); 12.9-13 (bs, 1H).

Example 26

8-(4-Methoxy-phenyl)-1-propyl-2-(3-trifluoromethyl-phenyl)-1,7-dihydro-purin-6-one Obtained following analogous procedure of Example 25 starting from appropriate intermediates.

¹HNMR (400 MHz, DMSO d6): δ −0.67 (t, J=7.6 Hz, 3H); 1.51-1.55 (m, 2H); 3.41 (m, 2H); 3.84 (s, 3H); 7.11 (d, J=8.8 Hz, 2H); 7.80-7.83 (m, 1H); 7.94-7.97 (m, 2H); 8.06 (s, 1H); 8.13 (d, J=8.4 Hz, 2H).

Example 27

8-{1-[3-(4-Fluoro-phenyl)-prop-2-ynyl]-1H-pyrazol-4-yl}-1-propyl-2-pyrrolidin-1-yl-1,7-dihydro-purin-6-one

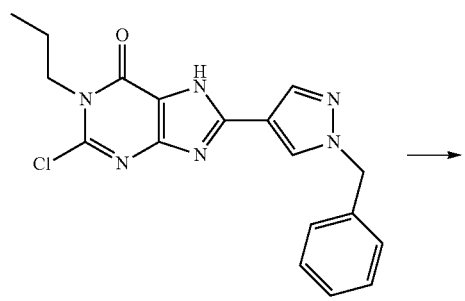

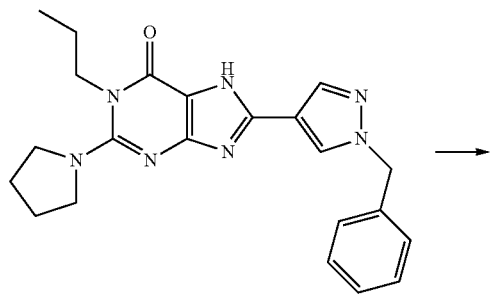

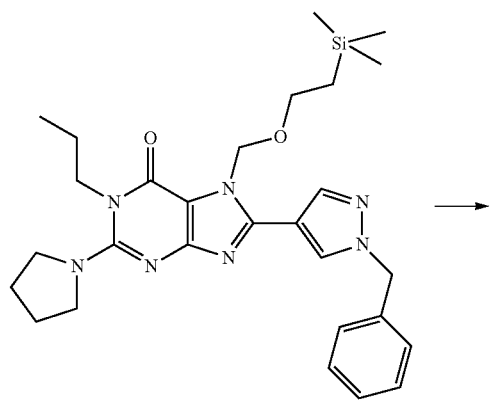

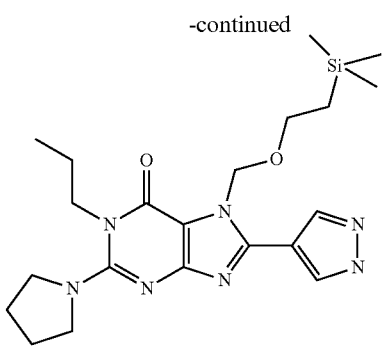

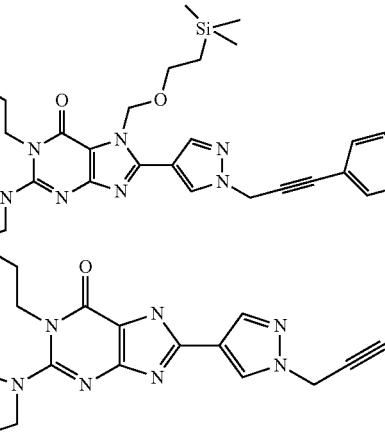

Step 1: 8-(r-Benzyl-1H-pyrazol-4-yl)-1-propyl-2-pyrrolidin-1-yl-1,7-dihydro-purin-6-one A mixture of 8-(1-benzyl-1H-pyrazol-4-yl)-2-chloro-1-propyl-1,7-dihydro-purin-6-one (prepared as given in Example 1) (1.2 g, 3.2 mmol), pyrrolidine (0.34 g, 4.8 mmol), Diisopropyl ethyl amine (0.826 g, 6.4 mmol) and N-methyl pyrrolidone (12 ml) were heated at 80-90° C. for 20 hours. Reaction mixture was cooled to 20-25° C. and water (20 ml) was added, solid separated out. The solid material was filtered off and purified by column chromatography to get pure 8-(1-Benzyl-1-pyrazol-4-yl)-1-propyl-2-pyrrolidin-1-yl-1,7-dihydro-purin-6-one as off white solid (0.83 g, 64%).

¹HNMR (400 MHz, DMSO d6): δ 0.80-0.86 (m, 3H); 1.66-1.70 (m, 2H); 1.87-1.94 (m, 4H); 3.29-3.32 (m, 2H); 3.41-3.44 (m, 2H); 4.01-4.04 (m, 2H); 5.4 (s, 2H); 7.28-7.39 (m, 5H); 8.02 (s, 1H); 8.3 (s, 1H); 13.03 (s, 1H)

Step 2: 8-(1-Benzyl-1H-pyrazol-4-yl)-1-propyl-2-pyrrolidin-1-yl-7-(2-trimethylsilanyl-ethoxymethyl)-1,7-dihydro-purin-6-one A mixture of 8-(1-Benzyl-1H-pyrazol-4-yl)-1-propyl-2-pyrrolidin-1-yl-1,7-dihydro-purin-6-one (0.83 g, 2.1 mmol) and potassium carbonate (0.857 g, 6.2 mmol) was taken in DMF (5 ml) and 2-(trimethylsilyl)ethoxymethyl chloride (1.0 ml, 6.2 mmol) was added drop wise at 0° C. and the mixture was stirred at 20° C. for 4 hours. The mixture was cooled to 10° C. and diluted with water (10 ml). The aqueous layer was extracted with ethyl acetate (3×15 ml). The organic layer was washed with saturated brine solution (2×15 ml) and dried over Na₂SO₄. Solvent was evaporated and the residue was further purified by column chromatography to obtain the above product as pale yellow semisolid (0.325 g, 30%)

¹HNMR (400 MHz, DMSO d6): δ −0.004-(−0.01) (m, 9H); 0.9-0.97 (m, 5H); 1.75-1.80 (m, 2H); 1.96-2.0 (m, 4H); 3.40-3.44 (m, 2H); 3.50-3.56 (m, 2H); 3.74 (t, J=8 Hz, 2H); 4.12-4.14 (m, 2H); 5.55 (s, 2H); 5.91 (s, 2H); 7.41-7.48 (m, 5H); 8.12 (s, 1H); 8.52 (s, 1H).

Step 3: 1-Propyl-8-(1H-pyrazol-4-yl)-2-pyrrolidin-1-yl-7-(2-trimethylsilanyl-ethoxymethyl)-1,7-dihydro-purin-6-one A mixture of 8-(1-Benzyl-1H-pyrazol-4-yl)-1-propyl-2-pyrrolidin-1-yl-7-(2-trimethylsilanyl-ethoxymethyl)-1,7-dihydro-purin-6-one (0.154 g, 0.29 mmol), and DMSO (0.2 ml, 2.9 mmol) was taken in THF (10 ml). 0.5M solution of KO$^t$Bu (4 ml, 2.0 mmol) in THF was added at 0° C. and stirred for 18 hours. After adding saturated NH$_4$Cl solution, the compound was extracted with ethyl acetate (2×10 ml). Organic layer was washed with brine (2×10 ml), dried over Na$_2$SO$_4$. Solvent was evaporated and purified by preparative TLC to get pure 1-Propyl-8-(1H-pyrazol-4-yl)-2-pyrrolidin-1-yl-7-(2-trimethylsilanyl-ethoxymethyl)-1,7-dihydro-purin-6-one as white solid (89 mg, 70%)

¹HNMR (400 MHz, DMSO d6): δ 0.004-(−0.01) (m, 9H); 0.88-0.97 (m, 5H); 1.74-1.80 (m, 2H); 1.96-2.0 (m, 4H); 3.40-3.44 (m, 2H); 3.50-3.52 (m, 2H); 3.74 (t, J=7.6 Hz, 2H); 4.12 (t, J=6.8 Hz, 2H); 5.90 (s, 2H); 8.25 (s, 2H)

Step 4: 8-{1-[3-(4-Fluoro-phenyl)-prop-2-ynyl]-1H-pyrazol-4-yl}-1-propyl-2-pyrrolidin-1-yl-7-(2-trimethylsilanyl-ethoxymethyl)-1,7-dihydro-purin-6-one A mixture of 1-Propyl-8-(1H-pyrazol-4-yl)-2-pyrrolidin-1-yl-7-(2-trimethylsilanyl-ethoxymethyl)-1,7-dihydro-purin-6-one (0.111 g, 0.25 mmol), potassium carbonate (0.052 g, 0.38 mmol), 1-(3-bromo-prop-1-ynyl)-4-fluoro-benzene (0.69 g, 0.33 mmol) was taken in acetone (10 ml). The reaction mixture was heated at 80° C. for 2 hours. The mixture was cooled to room temperature and filtered through sintered funnel, washed with acetone. Solvent was evaporated and the residue was purified by preparative TLC to obtain pure 8-{1-[3-(4-Fluoro-phenyl)-prop-2-ynyl]-1H-pyrazol-4-yl}-1-propyl-2-pyrrolidin-1-yl-7-(2-trimethylsilanyl-ethoxymethyl)-1,7-dihydro-purin-6-one (0.025 g, 22%) as colourless oil.

Step 5: 8-{1-[3-(4-Fluoro-phenyl)-prop-2-ynyl]-1H-pyrazol-4-yl}-1-propyl-2-pyrrolidin-1-yl-1,7-dihydro-purin-6-one A mixture of 8-{1-[3-(4-Fluoro-phenyl)-prop-2-ynyl]-1H-pyrazol-4-yl}-1-propyl-2-pyrrolidin-1-yl-7-(2-trimethylsilanyl-ethoxymethyl)-1,7-dihydro-purin-6-one (0.025 g, 0.043 mmol), 2N HCl (0.5 ml), ethanol (2 ml) was heated at 85° C. for 2 hours. The mixture was cooled and the solvent was evaporated. The residue was washed with n-pentane to obtain pure 8-{1-[3-(4-Fluoro-phenyl)-prop-2-ynyl]-1H-pyrazol-4-yl)}-1-propyl-2-pyrrolidin-1-yl-1,7-dihydro-purin-6-one (0.021 g, quantitative) as yellow solid.

¹HNMR (400 MHz, DMSO d6): δ 0.92 (t, J=7.6 Hz, 3H); 1.75-1.80 (m, 2H); 1.99-2.02 (m, 4H); 3.60-3.64 (m, 4H); 4.18 (t, J=7.2 Hz, 2H); 5.38 (s, 2H); 7.11-7.15 (m, 2H); 7.52-7.55 (m, 2H); 8.19 (s, 1H); 8.65 (s, 1H).

Example 28

1-Propyl-8-[6-(3-trifluoromethyl-benzylamino)-pyridin-3-yl]-1,7-dihydro-purin-6-one

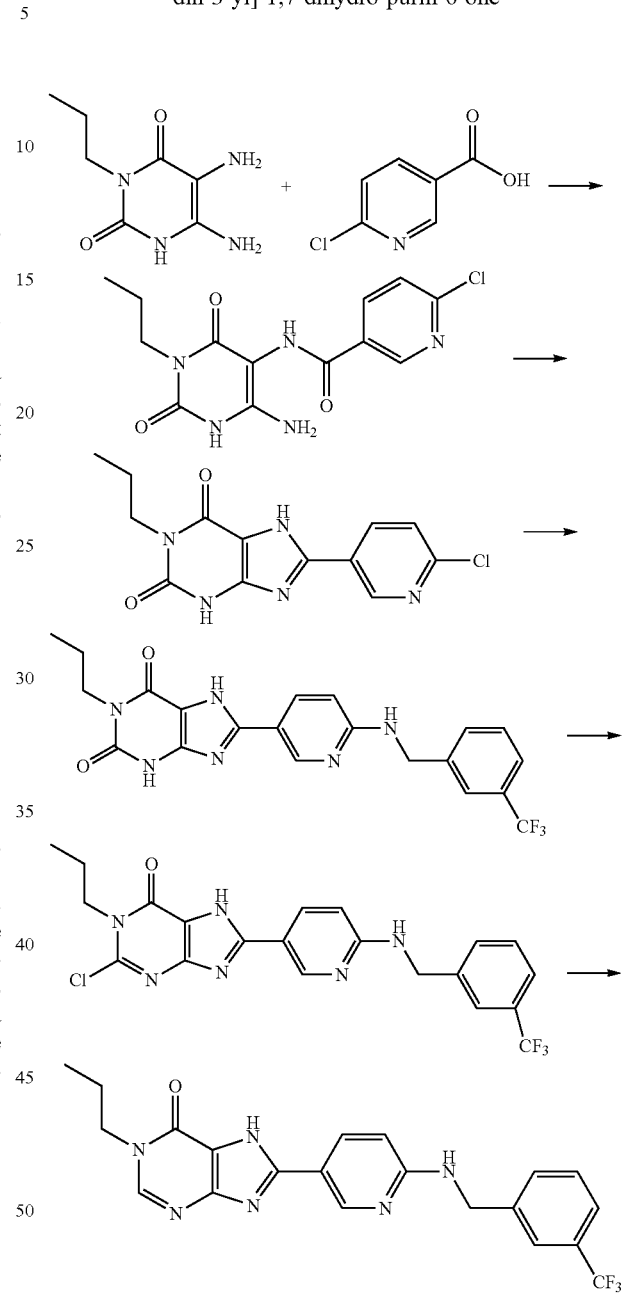

Step 1: N-(6-Amino-2,4-dioxo-3-propyl-1,2,3,4-tetrahydro-pyrimidin-5-yl)-6-chloro-nicotinamide A mixture of 5,6-diamino-3-propyl-1H-pyrimidine-2,4-dione (2.0 g, 11.0 mmol), 6-Chloro nicotinic acid (1.86 g, 11.8 mmol) in methanol (40 ml) were cooled to 0° C. and added EDCI.HCl (4.2 g, 22 mmol). The reaction mixture was stirred at 25° C. for 20 hours and the solvents were removed under reduced pressure. To this residue water (20 ml) was added and the precipitate was filtered off, and washed sequentially with cold water (20 ml) and methanol (5 ml) to obtain N-(6-Amino-2,4-dioxo-3-propyl-1,2,3,4-tetrahydro-pyrimidin-5-yl)-6-chloro-nicotinamide as an off white solid. (2.47 g, 70%).

¹HNMR (400 MHz, DMSO d6): δ0.81 (t, J=7.6 Hz, 3H); 1.45-1.51 (m, 2H); 3.64 (t, J=7.2 Hz, 2H); 6.24 (s, 2H); 7.65 (d, J=8.4 Hz, 1H); 8.29 (dd, J=8.4 Hz, 2.4 Hz, 1H); 8.90 (d, J=2 Hz, 1H); 9.17 (s, 1H); 10.54 (s, 1H)

Step 2: 8-(6-Chloro-pyridin-3-yl)-1-propyl-3,7-dihydro-purine-2,6-dione

A mixture of N-(6-Amino-2,4-dioxo-3-propyl-1,2,3,4-tetrahydro-pyrimidin-5-yl)-6-chloro-nicotinamide (2.47 g, 7.6 mmol), P₂O₅ was taken in DMF (20 ml) and heated at 100-102° C. for 30 minute. Reaction mixture was cooled to room temperature and cold water (60 ml) was added. Precipitated solid was filtered off to get 8-(6-Chloro-pyridin-3-yl)-1-propyl-3,7-dihydro-purine-2,6-dione as pale yellow solid (1.8 g, 77%).

¹HNMR (400 MHz, DMSO d6): δ 0.84-0.90 (m, 3H); 1.53-1.59 (m, 2H); 3.79-3.09 (m, 2H); 7.69 (d, J=8 Hz, 1H); 8.42 (dd, J=8.8 Hz, 2.4 Hz, 1H); 9.04 (d, J=2.4 Hz, 1H); 11.99 (s, 1H); 14.01 (s, 1H)

Step 3: 1-Propyl-8-[6-(3-trifluoromethyl-benzylamino)-pyridin-3-yl]-3,7-dihydro-purine-2,6-dione A mixture of 8-(6-Chloro-pyridin-3-yl)-1-propyl-3,7-dihydro-purine-2,6-dione (0.5 g, 1.6 mmol) and 3-Trifluoromethyl-benzylamine (3 ml) was stirred in sealed tube for 48 hours at 200° C. Reaction mixture was cooled and filtered, washed with ethanol to get 1-Propyl-8-[6-(3-trifluoromethyl-benzylamino)-pyridin-3-yl]-3,7-dihydro-purine-2,6-dione as off white solid (0.61 g, 84%).

¹HNMR (400 MHz, DMSO d6): δ 0.87 (t, J=7.4 Hz, 3H); 1.53-1.59 (m, 2H); 3.80 (t, J=7.6 Hz, 2H); 4.64 (d, J=6 Hz, 2H); 6.65 (d, J=8.8 Hz, 1H); 7.54-7.68 (m, 4H); 7.79 (m, 1H); 8.01-8.04 (dd, J=8 Hz, 2.3 Hz, 1H); 8.68 (d, J=2 Hz, 1H); 11.8 (bs, 1H); 13.30 (bs, 1H)

Step 4: 2-Chloro-1-propyl-8-[6-(3-trifluoromethyl-benzylamino)-pyridin-3-yl]-1,7-dihydro-purin-6-one A mixture of 1-Propyl-8-[6-(3-trifluoromethyl-benzylamino)-pyridin-3-yl]-3,7-dihydro-purine-2,6-dione (0.2 g, 0.45 mmol), POCl₃ (5 ml) and NH₄Cl (0.486 g, 9 mmol) were heated at 125-130° C. for 20 hours. Reaction mixture was cooled to 20-25° C. It was then concentrated under vacuum. The residue was dissolved in water (50 ml) and precipitated solid was filtered off. The solid obtained was further purified by column chromatography to obtain pure 2-Chloro-1-propyl-8-[6-(3-trifluoromethyl-benzylamino)-pyridin-3-yl]-1,7-dihydro-purin-6-one as pale yellow solid (0.054 g, 26%).

¹HNMR (400 MHz, DMSO d6): δ 0.91 (t, J=7.6 Hz, 3H); 1.65-1.71 (m, 2H); 4.14 (t, J=7.6 Hz, 2H); 4.63 (d, J=5.2 Hz, 2H); 6.65 (d, J=8.8 Hz, 1H); 7.53-7.67 (m, 4H); 7.78 (s, 1H); 8.07 (s, 1H); 8.75 (s, 1H); 13.61 (bs, 1H)

Similarly following compounds have been made starting from appropriate intermediates: 2-Chloro-8-[6-(3-fluoro-benzylamino)-pyridin-3-yl]-1-propyl-1,7-dihydro-purin-6-one ¹HNMR (400 MHz, DMSO d6): δ 0.94 (t, J=7.6 Hz, 3H); 1.68-1.74 (m, 2H); 4.16 (t, J=7.2 Hz, 2H); 4.58 (d, J=6.0 Hz, 2H); 6.65 (d, J=8.8 Hz, 1H); 7.04-7.19 (m, 3H); 7.34-7.40 (m, 1H); 7.74 (s, 1H); 8.08 (s, 1H); 8.75 (s, 1H); 13.61 (bs, 1H)

Step 5: 1-Propyl-8-[6-(3-trifluoromethyl-benzylamino)-pyridin-3-yl]-1,7-dihydro-purin-6-one A mixture of 2-Chloro-1-propyl-8-[6-(3-trifluoromethyl-benzylamino)-pyridin-3-yl]-1,7-dihydro-purin-6-one (0.094 g, 0.2 mmol), Ammonium formate (0.256 g, 0.4 mmol), Pd/C (0.094 g) and DMF (4 ml) were stirred for 30 minutes at 60° C. The reaction mixture was cooled to room temperature and filtered through celite bed. The organic volatiles were evaporated and the residue was acidified with citric acid. The solid precipitated out was filtered to get pure 1-Propyl-8-[6-(3-trifluoromethyl-benzylamino)-pyridin-3-yl]-1,7-dihydro-purin-6-one as off white solid (16 mg, 40%). ¹HNMR (400 MHz, DMSO d6): δ 0.84-0.90 (m, 3H); 1.66-1.73 (m, 2H); 3.94-3.99 (m, 2H); 4.65 (d, J=5.6 Hz, 2H); 6.66 (d, J=9.2 Hz, 1H); 7.55-7.79 (m, 4H); 8.13 (dd, J=8.8 Hz, 2.4 Hz, 1H); 8.30 (s, 1H); 8.78 (d, J=2.4 Hz, 1H); 13.56 (s, 1H)

Example 29

2-Amino-1-propyl-8-[1-(3-trifluoromethyl-benzyl)-1H-pyrazol-4-yl]-1,7-dihydro-purin-6-one

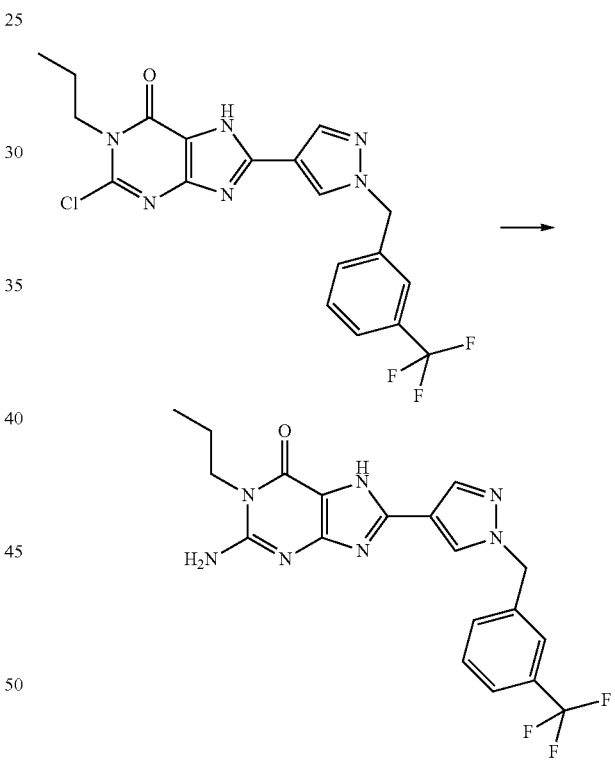

A mixture of 2-Chloro-1-propyl-8-[1-(3-trifluoromethyl-benzyl)-1H-pyrazol-4-yl]-1,7-dihydro-purin-6-one (0.2 g, 0.45 mmol) (prepared as given in Example 1), ammonia solution (20 ml) was heated at 125-130° C. in a sealed tube for 5 days. Reaction mixture was cooled to 0° C. and solid was filtered, washed with methanol, dried and purified by column chromatography using silica gel (100-200 mesh) and 6 to 8% methanol in DCM as an eluent to obtain 2-Amino-1-propyl-8-[1-(3-trifluoromethyl-benzyl)-1H-pyrazol-4-yl]-1,7-dihydro-purin-6-one (0.079 g, 41%) as a white solid.

¹HNMR (400 MHz, CD₃OD): δ 1.02 (t, J=7.4 Hz, 3H); 1.72-1.77 (m, 2H); 4.02 (t, J=7.8 Hz, 2H); 5.54 (s, 2H); 7.60-7.68 (m, 4H); 8.11 (s, 1H); 8.33 (s, 1H).

Example 30

2-Fluoro-1-propyl-8-[1-(3-trifluoromethyl-benzyl)-1H-pyrazol-4-yl]-1,7dihydro-purin-6-one

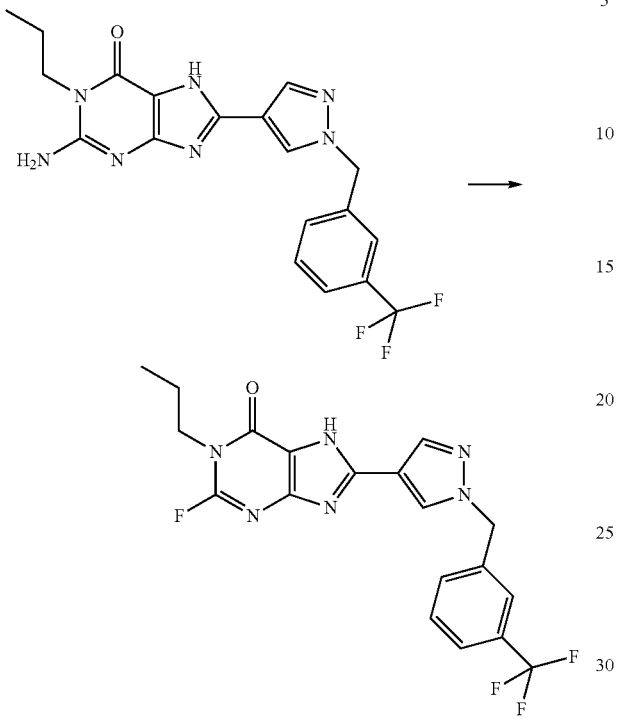

To a mixture of 2-Amino-1-propyl-8-[1-(3-trifluoromethyl-benzyl)-1H-pyrazol-4-yl]-1,7-dihydro-purin-6-one (0.112 g, 0.27 mmol) and tert-butyl nitrite (0.07 ml, 0.54 mmol), 70% HF in pyridine (0.6 ml) was added at 0° C. and stirred for 3 hours at room temperature. Reaction mixture was diluted with DCM (10 ml) and washed with water (10 ml) followed by brine (2×10 ml). Organic layer was dried over $Na_2SO_4$, concentrated and further purified by preparative HPLC to get pure 2-Fluoro-1-propyl-8-[1-(3-trifluoromethyl-benzyl)-1H-pyrazol-4-yl]-1,7 dihydro-purin-6-one as light brown solid (0.016 g, 2%).

$^1$HNMR (400 MHz, DMSO d6): δ 0.99 (t, J=7.2 Hz, 3H); 1.74-1.78 (m, 2H); 4.06-4.11 (m, 2H); 5.53 (s, 2H); 7.56-7.63 (m, 4H); 8.11 (s, 1H); 8.35 (s, 1H)

Example 31

1-Propyl-2-trifluoromethyl-8-[1-(3-trifluoromethyl-benzyl)-1H-pyrazol-4-yl]-1,7-dihydro-purin-6-one

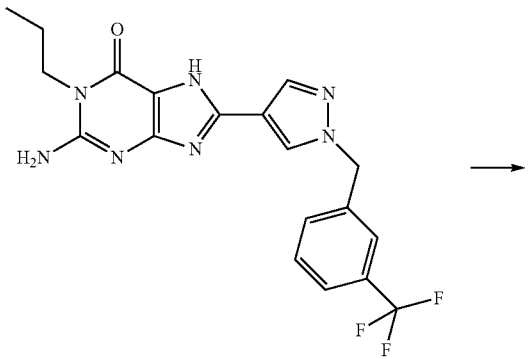

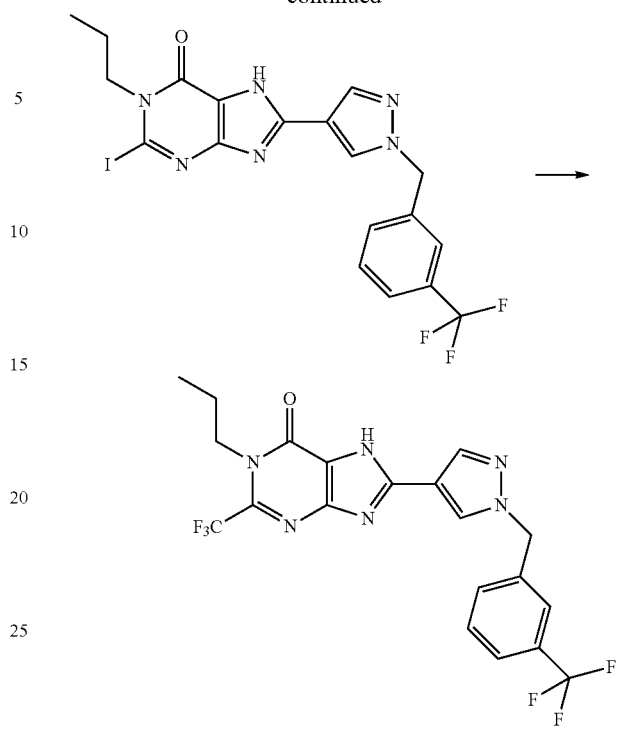

Step 1: 2-Iodo-1-propyl-8-[1-(3-trifluoromethyl-benzyl)-1H-pyrazol-4-yl]-1,7-dihydro-purin-6-one A mixture of 2-Amino-1-propyl-8-[1-(3-trifluoromethyl-benzyl)-1H-pyrazol-4-yl]-1,7-dihydro-purin-6-one (prepared as given in Example 13) (0.169 g, 0.41 mmol), isoamyl nitrite (0.2 ml, 1.5 mmol), iodine (83 mg, 0.32 mmol) was taken in THF (5 ml) and stirred for 2 hours at 80° C. Reaction mixture was cooled and saturated solution of $Na_2S_2O_3$ was added and extracted with ethyl acetate (3×5 ml). The organic layer was washed with brine (10 ml), dried over $Na_2SO_4$ and evaporated to obtain 2-Iodo-1-propyl-8-[1-(3-trifluoromethyl-benzyl)-1H-pyrazol-4-yl]-1,7-dihydro-purin-6-one (93 mg, 44%).

Step 2: 1-Propyl-2-trifluoromethyl-8-[1-(3-trifluoromethyl-benzyl)-1H-pyrazol-4-yl]-1,7-dihydro-purin-6-one A mixture of 2-Iodo-1-propyl-8-[1-(3-trifluoromethyl-benzyl)-1H-pyrazol-4-yl]-1,7-dihydro-purin-6-one (36 mg, 0.068 mmol), Zn dust (10 mg, 0.136 mmol) and THF (2 ml) was stirred for 2 hours at room temperature. Trifluoromethyl iodide gas was passed through the reaction mixture and HMPA (2 ml) was added and heated at 120° C. for 18 hours. The reaction mixture was cooled to room temperature, organic volatile solvent was evaporated and the residue was extracted with DCM (2×10 ml). The organic layer was washed with brine (10 ml), dried over $Na_2SO_4$, evaporated and purified by preparative HPLC to get 1-Propyl-2-trifluoromethyl-8-[1-(3-trifluoromethyl-benzyl)-1H-pyrazol-4-yl]-1,7-dihydro-purin-6-one as pale yellow solid (4.5 mg, 14%).

¹HNMR (400 MHz, DMSO d6): δ 0.93 (t, J=7.6 Hz, 3H); 1.65-1.69 (m, 2H); 3.98-4.01 (m, 2H); 5.54 (s, 2H); 7.59-7.63 (m, 2H); 7.68-7.70 (m, 2H); 8.18 (s, 1H); 8.58 (s, 1H); 13.95 (s, 1H)

Example 32

2-Cyclopropyl-1-propyl-8-[1-(3-trifluoromethyl-benzyl)-1H-pyrazol-4-yl]-1,7-dihydro-purin-6-one

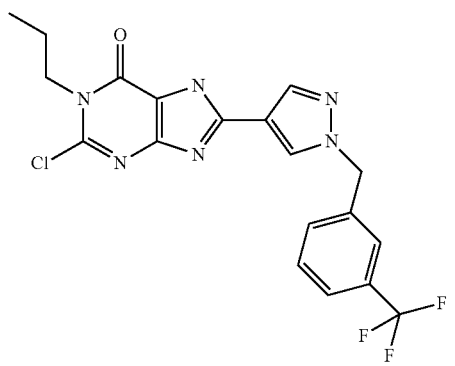

A mixture of 2-Chloro-1-propyl-8-[1-(3-trifluoromethyl-benzyl)-1H-pyrazol-4-yl]-1,7-dihydro-purin-6-one (prepared using same procedure as given in Example 2) (0.1 g, 0.23 mmol), Pd(PPh₃)⁴ (0.319 g, 0.28 mmol) and cyclopropyl zinc chloride solution (10 ml, 0.5 M solution) were heated at 100° C. for 30 minutes. Reaction mixture was cooled, diluted with DCM (10 ml). Organic layer washed with brine (2×10 ml), dried over Na₂SO₄, evaporated and purified by preparative TLC to obtain pure 2-Cyclopropyl-1-propyl-8-[1-(3-trifluoromethyl-benzyl)-1H-pyrazol-4-yl]-1,7-dihydro-purin-6-one as white solid (23 mg, 23%)

¹HNMR (400 MHz, DMSO d6): δ 1.05 (t, J=7.6 Hz, 3H); 1.11-1.13 (m, 4H); 1.81-1.86 (m, 2H); 2.21-2.26 (m, 1H); 4.33 (t, J=7.6 Hz, 2H); 5.51 (s, 2H); 7.24-7.42 (m, 2H); 7.49-7.63 (m, 2H); 8.09 (s, 1H); 8.33 (s, 1H)

Example 33

1-Propyl-8-[1-(3-trifluoromethyl-benzyl)-1H-pyrazol-4-yl]-2-(4-trifluoromethyl-phenyl)-1,7-dihydro-purin-6-one

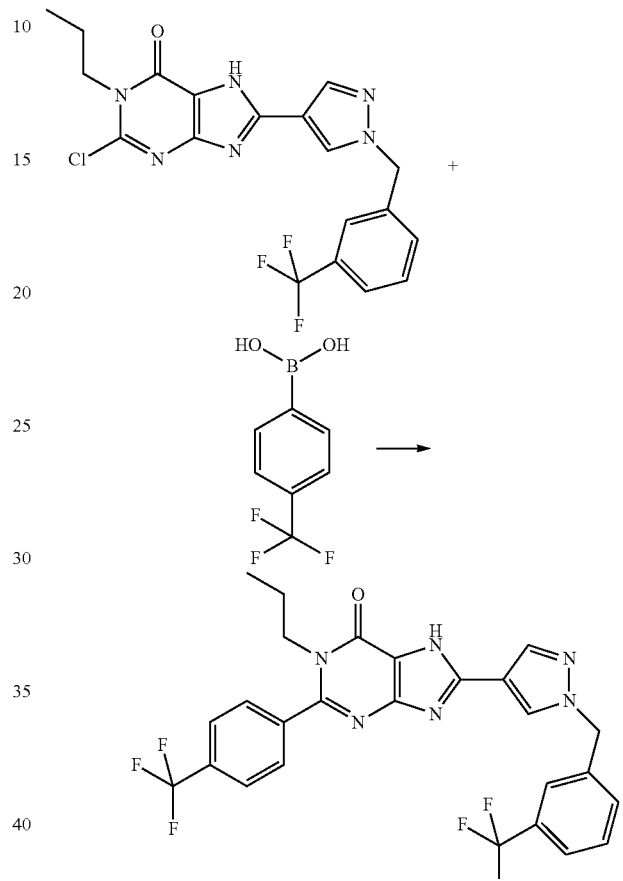

Step 1: 1-Propyl-8-[1-(3-trifluoromethyl-benzyl)-1H-pyrazol-4-yl]-2-(4-trifluoromethyl-phenyl)-1,7-dihydro-purin-6-one A mixture of 2-Chloro-1-propyl-8-[1-(3-trifluoromethyl-benzyl)-1H-pyrazol-4-yl]-1,7-dihydro-purin-6-one (0.1 g, 0.239 mmol) and 4-Trifluoromethylphenyl boronic acid (0.038 g, 0.239 mmol) in THF (5 ml) were stirred at room temperature under argon and added 1M aqueous NaHCO₃ (0.04 g, 0.478 mmol) and Pd(PPh₃)₄ (0.013 g, 0.0119 mmol). The reaction mixture was heated at 80° C. for overnight and the solvent was removed under reduced pressure. The residue was purified by column chromatography to obtain 1-Propyl-8-[1-(3-trifluoromethyl-benzyl)-1H-pyrazol-4-yl]-2-(4-trifluoromethyl-phenyl)-1,7-dihydro-purin-6-one (0.05 g, 36%) as a white solid.

¹HNMR (400 MHz, DMSO d6): δ 0.65 (t, J=7.2 Hz, 3H); 1.49-1.51 (m, 2H); 3.83 (t, J=7.2 Hz, 2H); 5.54 (s, 2H); 7.61-7.71 (m, 4H); 7.83-7.93 (m, 4H); 8.19 (s, 1H); 8.61 (s, 1H); 13.62 (bs, 1H).

Examples 34-36 were prepared in an analogous manner of Example 33 from appropriate intermediates.

| Example | IUPAC name |
|---|---|
| 34 | 1-Propyl-8-[1-(3-trifluoromethyl-benzyl)-1H-pyrazol-4-yl]-2-(3-trifluoromethyl-phenyl)-1,7-dihydro-purin-6-one |
| 35 | 2-(3-Fluoro-phenyl)-1-propyl-8-[1-(3-trifluoromethyl-benzyl)-1H-pyrazol-4-yl]-1,7-dihydro-purin-6-one |
| 36 | 8-(1-Benzyl-1H-pyrazol-4-yl)-2-furan-2-yl-1-propyl-1,7-dihydro-purin-6-one |

Examples 38-40 were prepared in an analogous manner of Example 37 from appropriate intermediates.

| Example | IUPAC name |
|---|---|
| 38 | 1,2-Dipropyl-8-[1-(3-trifluoromethyl-benzyl)-1H-pyrazol-4-yl]-1,7-dihydro-purin-6-one |
| 39 | 2-Methyl-1-propyl-8-[1-(3-trifluoromethyl-benzyl)-1H-pyrazol-4-yl]-1,7-dihydro-purin-6-one |
| 40 | 2-Benzyl-1-propyl-8-[1-(3-trifluoromethyl-benzyl)-1H-pyrazol-4-yl]-1,7-dihydro-purin-6-one |

Example 37

2-Ethyl-1-propyl-8-[1-(3-trifluoromethyl-benzyl)-1H-pyrazol-4-yl]-1,7-dihydro-purin-6-one

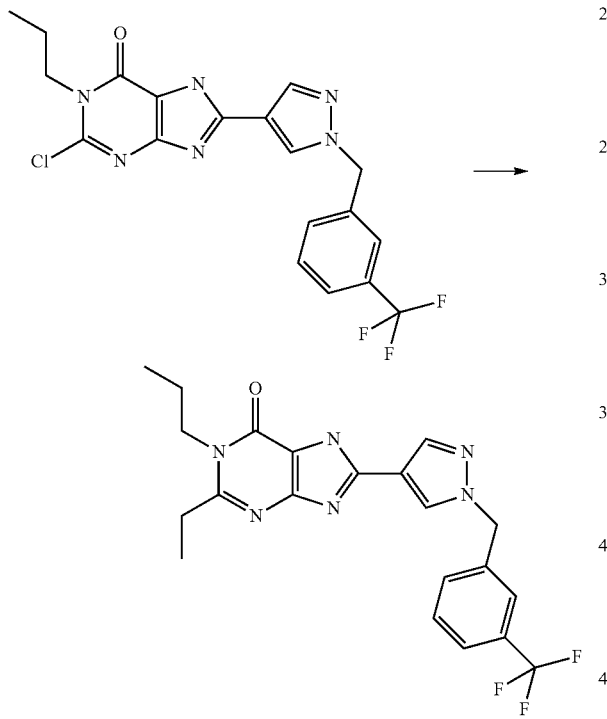

Step 1: 2-Ethyl-1-propyl-8-[1-(3-trifluoromethyl-benzyl)-1H-pyrazol-4-yl]-1,7-dihydro-purin-6-one To a solution of 2-Chloro-1-propyl-8-[1-(3-trifluoromethyl-benzyl)-1H-pyrazol-4-yl]-1,7-dihydro-purin-6-one (0.1 g, 0.239 mmol) in dioxane (5 ml) under argon was added ethyl magnesium bromide (0.05 g, 1.146 mmol, 1M solution) and 1M zinc chloride (0.031 g, 2.39 mmol, 1M). To this solution Pd(PPh$_3$)$_4$ (0.026 g, 0.0239 mmol) was added. The reaction mixture was heated at 50° C. for overnight. The reaction mixture was filtered through celite pad and the solvents were removed under reduced pressure. The residue was purified by column chromatography to obtain 2-Ethyl-1-propyl-8-[1-(3-trifluoromethyl-benzyl)-1H-pyrazol-4-yl]-1,7-dihydro-purin-6-one (0.01 g, 10%) as a white solid.

$^1$HNMR (400 MHz, DMSO d6): δ 1.03 (t, J=7.2 Hz, 3H); 1.38 (t, J=7.4 Hz, 3H); 1.74-1.75 (m, 2H); 2.94-2.96 (m, 2H); 4.12 (t, J=7.2 Hz, 2H); 5.52 (s, 2H); 7.57-7.63 (m, 4H); 8.12 (s, 1H); 8.35 (s, 1H)

Example 41

8-(1-Benzyl-1H-pyrazol-4-yl)-2-methylamino-1-propyl-1,7-dihydro-purin-6-one

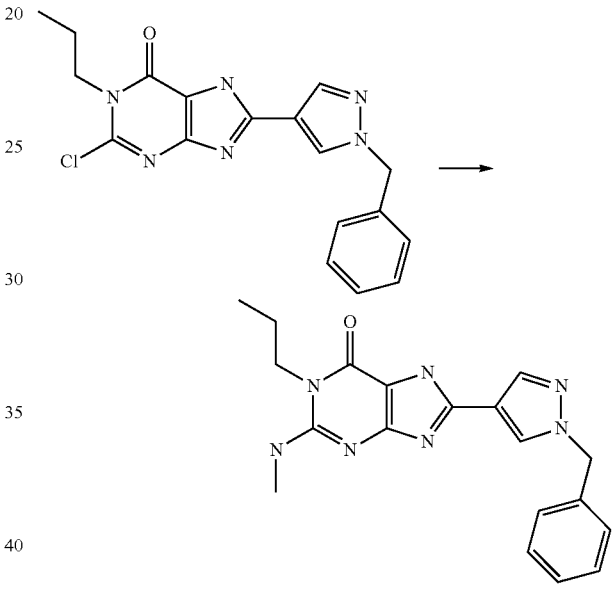

Step 1: 8-(1-Benzyl-1H-pyrazol-4-yl)-2-methylamino-1-propyl-1,7-dihydro-purin-6-one To a solution of 8-(1-Benzyl-1H-pyrazol-4-yl)-2-chloro-1-propyl-1,7-dihydro-purin-6-one (0.05 g, 0.136 mmol) in THF (5 ml) under argon was added Diisopropyl ethyl amine (0.05 g, 0.407 mmol) and 1M methyl amine in THF (0.042 g, 1.36 mmol). The reaction mixture was heated at 50° C. for overnight. The reaction mixture concentrated under reduced pressure. The residue obtained was purified by column chromatography to obtain 8-(1-Benzyl-1H-pyrazol-4-yl)-2-methylamino-1-propyl-1,7-dihydro-purin-6-one (0.025 g, 51%) as a white solid.

$^1$HNMR (400 MHz, DMSO d6): δ 0.89 (t, J=7.2 Hz, 3H); 1.52-1.54 (m, 2H); 2.83 (s, 3H); 3.89 (t, J=7.2 Hz, 2H); 5.39 (s, 2H); 7.28-7.36 (m, 5H); 7.93-8.33 (m, 2H); 12.70 (bs, 1H).

Example 42

2-Dimethylamino-1-propyl-8-[1-(3-trifluoromethyl-benzyl)-1H-pyrazol-4-yl]-1,7-dihydro-purin-6-one Obtained following analogous procedure of Example 41 starting from appropriate intermediates.

¹HNMR (400 MHz, DMSO d6): δ 0.8 (t, J=7.2 Hz, 3H); 1.58-1.64 (m, 2H); 2.74 (s, 6H); 4.02 (t, J=7.2 Hz, 2H); 5.55 (s, 2H); 7.58-7.68 (m, 4H); 8.10-8.44 (m, 2H).

Example 43

8-(1-Benzyl-1H-pyrazol-4-yl)-2-methoxy-1-propyl-1,7-dihydro-purin-6-one

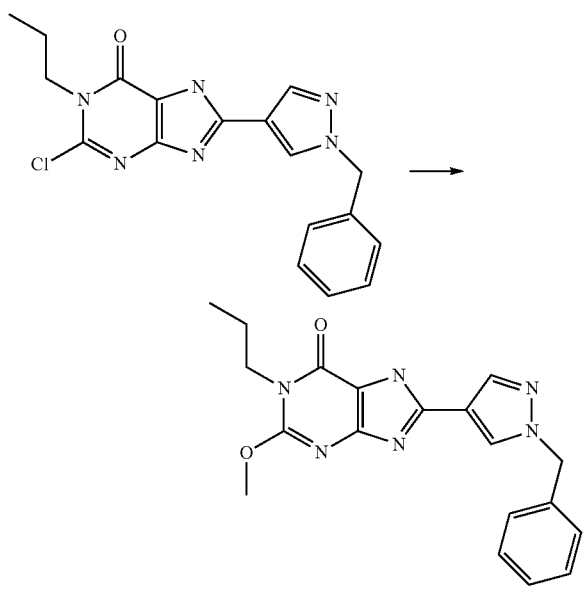

Step 1: 8-(1-Benzyl-1H-pyrazol-4-yl)-2-methoxy-1-propyl-1,7-dihydro-purin-6-one To a solution of 8-(1-Benzyl-1H-pyrazol-4-yl)-2-chloro-1-propyl-1,7-dihydro-purin-6-one (0.05 g, 0.136 mmol) in THF (5 ml) under argon was added Diisopropyl ethyl amine (0.05 g, 0.407 mmol) and 1M dimethyl amine in methanol (0.061 g, 1.36 mmol). The reaction mixture was heated at 50° C. for overnight. The reaction mixture concentrated under reduced pressure. The residue obtained was purified by column chromatography to obtain 8-(1-Benzyl-1H-pyrazol-4-yl)-2-methoxy-1-propyl-1,7-dihydro-purin-6-one (0.005 g, 10%) as a white solid.

¹HNMR (400 MHz, DMSO d6): δ 0.86 (t, J=7.2 Hz, 3H); 1.57 (m, 2H); 3.89 (m, 2H); 3.93 (s, 3H); 5.39 (s, 2H); 7.27-7.37 (m, 5H); 8.06 (s, 1H); 8.36 (s, 1H); 13.23 (bs, 1H).

Example 44

8-(1-Benzyl-1H-pyrazol-4-yl)-1-propyl-2-(4-trifluoromethyl-benzylamino)-1,7-dihydro-purin-6-one

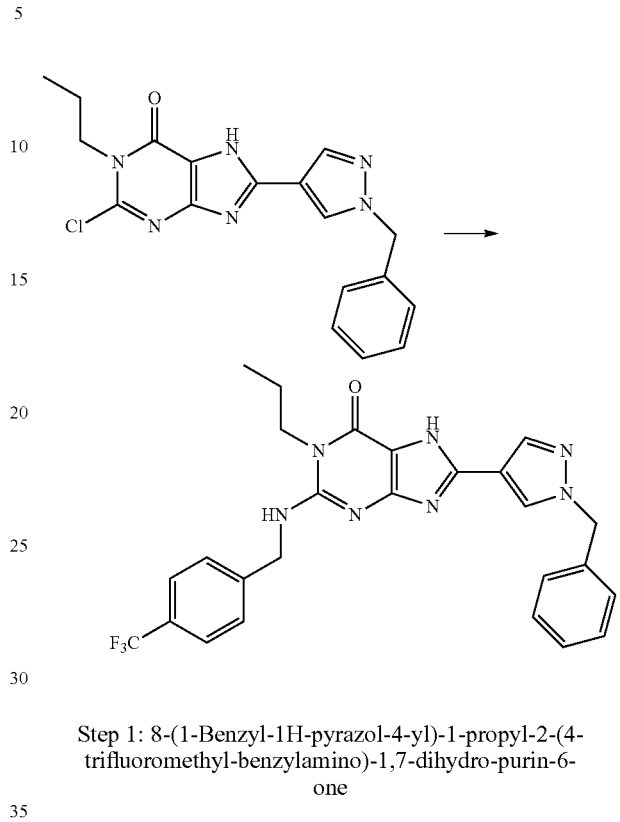

Step 1: 8-(1-Benzyl-1H-pyrazol-4-yl)-1-propyl-2-(4-trifluoromethyl-benzylamino)-1,7-dihydro-purin-6-one To a solution of 8-(1-Benzyl-1H-pyrazol-4-yl)-2-chloro-1-propyl-1,7-dihydro-purin-6-one (0.05 g, 0.136 mmol) in NMP (1 ml) under argon was added Diisopropyl ethyl amine (0.035 g, 0.27 mmol) and 4-Trifluoromethyl-benzylamine (0.035 g, 0.203 mmol). The reaction mixture was heated at 110° C. for overnight. The reaction mixture concentrated under reduced pressure. The residue was obtained was purified by preparative HPLC to obtain 8-(1-Benzyl-1H-pyrazol-4-yl)-2-methylamino-1-propyl-1,7-dihydro-purin-6-one (0.022 g, 32%) as a white solid.

¹HNMR (400 MHz, DMSO d6): δ 0.95 (t, J=7.2 Hz, 3H); 1.63 (m, 2H); 4.00 (t, J=7.2 Hz, 2H); 4.65 (s, 2H); 5.36 (s, 2H); 7.27-7.69 (m, 9H); 8.03 (s, 1H); 8.31 (s, 1H); 12.6 (bs, 1H).

Examples 45-79 were prepared in an analogous manner of Example 44 from appropriate intermediates.

| Example | IUPAC name |
|---|---|
| 45 | 8-(1-Benzyl-1H-pyrazol-4-yl)-1-propyl-2-(3-trifluoromethyl-benzylamino)-1,7-dihydro-purin-6-one |
| 46 | 8-(1-Benzyl-1H-pyrazol-4-yl)-2-[2-(4-methoxy-phenyl)-ethylamino]-1-propyl-1,7-dihydro-purin-6-one |
| 47 | 8-(1-Benzyl-1H-pyrazol-4-yl)-2-phenethylamino-1-propyl-1,7-dihydro-purin-6-one |
| 48 | 8-(1-Benzyl-1H-pyrazol-4-yl)-2-(4-methyl-piperazin-1-yl)-1-propyl-1,7-dihydro-purin-6-one |
| 49 | 8-(1-Benzyl-1H-pyrazol-4-yl)-2-piperidin-1-yl-1-propyl-1,7-dihydro-purin-6-one |

| Example | IUPAC name |
|---|---|
| 50 | 1-Propyl-2-pyrrolidin-1-yl-8-[1-(3-trifluoromethyl-benzyl)-1H-pyrazol-4-yl]-1,7-dihydro-purin-6-one |
| 51 | 2-Methylamino-1-propyl-8-[1-(3-trifluoromethyl-benzyl)-1H-pyrazol-4-yl]-1,7-dihydro-purin-6-one |
| 52 | 2-Cyclobutylamino-1-propyl-8-[1-(3-trifluoromethyl-benzyl)-1H-pyrazol-4-yl]-1,7-dihydro-purin-6-one |
| 53 | 2-Morpholin-4-yl-1-propyl-8-[1-(3-trifluoromethyl-benzyl)-1H-pyrazol-4-yl]-1,7-dihydro-purin-6-one |
| 54 | 2-(2-Hydroxy-ethylamino)-1-propyl-8-[1-(3-trifluoromethyl-benzyl)-1H-pyrazol-4-yl]-1,7-dihydro-purin-6-one |
| 55 | 2-((S)-2-Methoxymethyl-pyrrolidin-1-yl)-1-propyl-8-[1-(3-trifluoromethyl-benzyl)-1H-pyrazol-4-yl]-1,7-dihydro-purin-6-one |
| 56 | 2-((S)-2-Hydroxymethyl-pyrrolidin-1-yl)-1-propyl-8-[1-(3-trifluoromethyl-benzyl)-1H-pyrazol-4-yl]-1,7-dihydro-purin-6-one |
| 57 | 2-((R)-3-Hydroxy-pyrrolidin-1-yl)-1-propyl-8-[1-(3-trifluoromethyl-benzyl)-1H-pyrazol-4-yl]-1,7-dihydro-purin-6-one |
| 58 | 1-Propyl-2-(tetrahydro-pyran-4-ylamino)-8-[1-(3-trifluoromethyl-benzyl)-1H-pyrazol-4-yl]-1,7-dihydro-purin-6-one |
| 59 | (S)-1-{6-Oxo-1-propyl-8-[1-(3-trifluoromethyl-benzyl)-1H-pyrazol-4-yl]-6,7-dihydro-1H-purin-2-yl}-pyrrolidine-2-carboxylic acid amide |
| 60 | (2R,4R)-4-Hydroxy-1-{6-oxo-1-propyl-8-[1-(3-trifluoromethyl-benzyl)-1H-pyrazol-4-yl]-6,7-dihydro-1H-purin-2-yl}-pyrrolidine-2-carboxylic acid |
| 61 | 2-(2,3-Dihydroxy-propylamino)-1-propyl-8-[1-(3-trifluoromethyl-benzyl)-1H-pyrazol-4-yl]-1,7-dihydro-purin-6-one |
| 62 | 2-(2-Methoxy-ethylamino)-1-propyl-8-[1-(3-trifluoromethyl-benzyl)-1H-pyrazol-4-yl]-1,7-dihydro-purin-6-one |
| 63 | 2-{6-Oxo-1-propyl-8-[1-(3-trifluoromethyl-benzyl)-1H-pyrazol-4-yl]-6,7-dihydro-1H-purin-2-ylamino}-ethanesulfonic acid |
| 64 | 2-Isobutylamino-8-(1-methyl-1H-pyrazol-4-yl)-1-propyl-1,7-dihydro-purin-6-one |
| 65 | 8-(1-Methyl-1H-pyrazol-4-yl)-1-propyl-2-pyrrolidin-1-yl-1,7-dihydro-purin-6-one |
| 66 | 8-(1-Methyl-1H-pyrazol-4-yl)-2-phenethylamino-1-propyl-1,7-dihydro-purin-6-one |
| 67 | 2-[2-(4-Methoxy-phenyl)-ethyl amino]-8-(1-methyl-1H-pyrazol-4-yl)-1-propyl-1,7-dihydro-purin-6-one |
| 68 | 1-[8-(1-Methyl-1H-pyrazol-4-yl)-6-oxo-1-propyl-6,7-dihydro-1H-purin-2-yl]-pyrrolidine-2-carboxylic acid methyl ester |
| 69 | 2-Benzylamino-8-(1-methyl-1H-pyrazol-4-yl)-1-propyl-1,7-dihydro-purin-6-one |
| 70 | 2-(4-Methyl-piperazin-1-yl)-8-(1-methyl-1H-pyrazol-4-yl)-1-propyl-1,7-dihydro-purin-6-one |
| 71 | 2-[4-(4-Fluoro-phenyl)-piperazin-1-yl]-8-(1-methyl-1H-pyrazol-4-yl)-1-propyl-1,7-dihydro-purin-6-one |
| 72 | 2-Cyclopropylamino-8-(1-methyl-1H-pyrazol-4-yl)-1-propyl-1,7-dihydro-purin-6-one |
| 73 | 8-(1-Methyl-1H-pyrazol-4-yl)-1-propyl-2-(3-trifluoromethyl-benzylamino)-1,7-dihydro-purin-6-one |
| 74 | 2-(3-Hydroxymethyl-piperidin-1-yl)-1-propyl-8-[1-(3-trifluoromethyl-benzyl)-1H-pyrazol-4-yl]-1,7-dihydropurin-6-one |
| 75 | 2-(4-Hydroxymethyl-piperidin-1-yl)-1-propyl-8-[1-(3-trifluoromethyl-benzyl)-1H-pyrazol-4-yl]-1,7-dihydropurin-6-one |
| 76 | 2-(4-Hydroxy-piperidin-1-yl)-1-propyl-8-[1-(3-trifluoromethyl-benzyl)-1H-pyrazol-4-yl]-1,7-dihydro-purin-6-one |
| 77 | 2-(3-Hydroxy-piperidin-1-yl)-1-propyl-8-[1-(3-trifluoromethyl-benzyl)-1H-pyrazol-4-yl]-1,7-dihydro-purin-6-one |
| 78 | 2-Morpholin-4-yl-1-propyl-8-[1-(4-trifluoromethyl-benzyl)-1H-pyrazol-4-yl]-1,7-dihydro-purin-6-one |
| 79 | 2-(2-Hydroxy-ethylamino)-1-propyl-8-[1-(4-trifluoromethyl-benzyl)-1H-pyrazol-4-yl]-1,7-dihydro-purin-6-one |

Example 80

{6-Oxo-1-propyl-8-[1-(3-trifluoromethyl-benzyl)-1H-pyrazol-4-yl]-6,7-dihydro-1H-purin-2-ylamino}-acetic acid

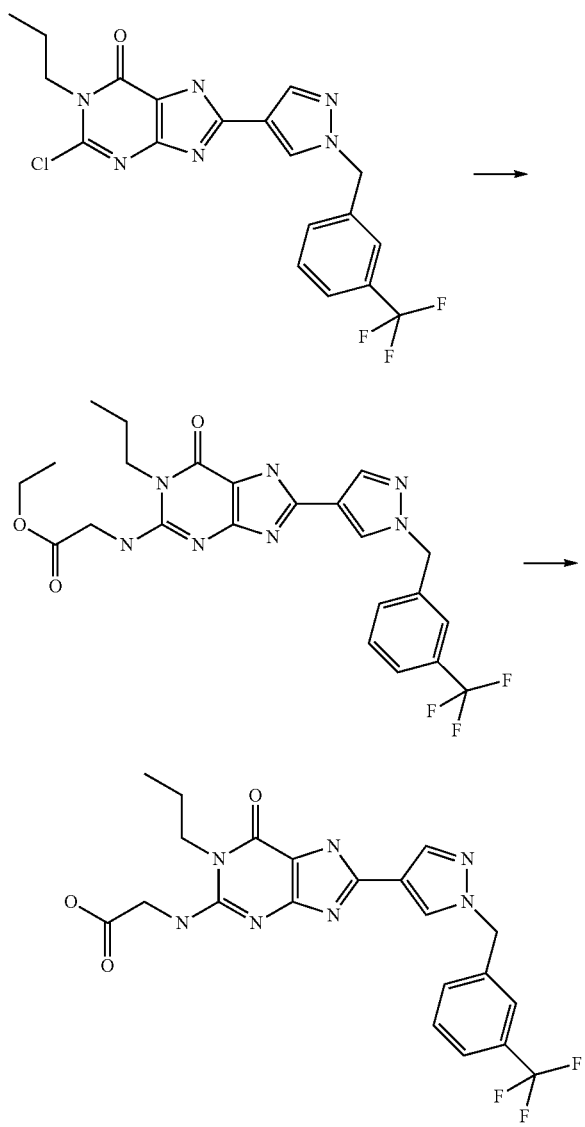

Step 1: {6-Oxo-1-propyl-8-[1-(3-trifluoromethyl-benzyl)-1H-pyrazol-4-yl]-6,7-dihydro-1H-purin-2-ylamino}-acetic acid ethyl ester To a solution of 2-Chloro-1-propyl-8-[1-(3-trifluorom-ethyl-benzyl)-1H-pyrazol-4-yl]-1,7-dihydro-purin-6-one (0.1 g, 0.22 mmol) in NMP (1.5 ml) under argon was added triethyl amine (0.113 g, 1.118 mmol) and ethyl glycine hydrochloride (0.096 g, 0.68 mmol). The reaction mixture was heated at 100° C. for 16 hours. To the reaction mixture ethyl acetate was added and it was washed with water and brine. Ethyl acetate layer was dried over sodium sulphate, filtered and concentrated under reduced pressure and residue obtained was purified by column chromatography to obtain {6-Oxo-1-propyl-8-[1-(3-trifluoromethyl-benzyl)-1H-pyrazol-4-yl]-6,7-dihydro-1H-purin-2-ylamino}-acetic acid ethyl ester (0.080 g, 69%) as an off white solid.

$^1$HNMR (400 MHz, DMSO d6): δ 0.91 (t, J=7.2 Hz, 3H); 1.2 (t, J=7.2 Hz, 3H); 1.52-1.54 (m, 2H); 3.90-4.04 (m, 2H); 4.00-4.16 (m, 4H); 5.52 (s, 2H); 7.58-7.74 (m, 4H); 7.98-8.43 (m, 2H); 12.70 (bs, 1H).

Step 2: {6-Oxo-1-propyl-8-[1-(3-trifluoromethyl-benzyl)-1H-pyrazol-4-yl]-6,7-dihydro-1H-purin-2-ylamino}-acetic acid A mixture of {6-Oxo-1-propyl-8-[1-(3-trifluoromethyl-benzyl)-1H-pyrazol-4-yl]-6,7-dihydro-1H-purin-2-ylamino}-acetic acid ethyl ester in THF (2 ml), MeOH (1 ml) and Water (1 ml) was added lithium hydroxide (0.02 g, 0.476 mmol) at 0° C. The reaction mixture was stirred at room temperature for overnight. The reaction mixture was concentrated and water was added. It was extracted with ethyl acetate. Ethyl acetate layer was washed with water and brine. Ethyl acetate layer was dried over sodium sulphate, filtered and concentrated under reduced pressure and the residue obtained was purified by column chromatography to obtain {6-Oxo-1-propyl-8-[1-(3-trifluoromethyl-benzyl)-1H-pyrazol-4-yl]-6,7-dihydro-1H-purin-2-ylamino}-acetic acid (0.035 g, 46%) as a yellow solid.

$^1$HNMR (400 MHz, CD$_3$OD): δ 0.99 (t, J=7.2 Hz, 3H); 1.70-1.80 (m, 2H); 4.05 (t, J=7.2 Hz, 2H); 4.12 (s, 2H); 5.48 (s, 2H); 7.54-7.68 (m, 4H); 8.04 (s, 1H); 8.26 (s, 1H).

Examples 81-86 were prepared in an analogous manner of Example 80 from appropriate intermediates.

| Example | IUPAC name |
|---|---|
| 81 | [8-(1-Benzyl-1H-pyrazol-4-yl)-6-oxo-1-propyl-6,7-dihydro-1H-purin-2-ylamino]-acetic acid ethyl ester |
| 82 | (Methyl-{6-oxo-1-propyl-8-[1-(3-trifluoromethyl-benzyl)-1H-pyrazol-4-yl]-6,7-dihydro-1H-purin-2-yl}-amino)-acetic acid |
| 83 | (S)-1-{6-Oxo-1-propyl-8-[1-(3-trifluoromethyl-benzyl)-1H-pyrazol-4-yl]-6,7-dihydro-1H-purin-2-yl}-pyrrolidine-2-carboxylic acid |
| 84 | 1-{6-Oxo-1-propyl-8-[1-(3-trifluoromethyl-benzyl)-1H-pyrazol-4-yl]-6,7-dihydro-1H-purin-2-yl}-piperidine-3-carboxylic acid |
| 85 | (R)-3-Methyl-2-{6-oxo-1-propyl-8-[1-(3-trifluoromethyl-benzyl)-1H-pyrazol-4-yl]-6,7-dihydro-1H-purin-2-ylamino}-butyric acid |
| 86 | 1-{6-Oxo-1-propyl-8-[1-(3-trifluoromethyl-benzyl)-1H-pyrazol-4-yl]-6,7-dihydro-1H-purin-2-yl}-piperidine-4-carboxylic acid |

Example 87

Preparation of 2-(3-Fluoro-phenoxy)-8-(1-methyl-1H-pyrazol-4-yl)-1-propyl-1,7dihydro-purin-6-one

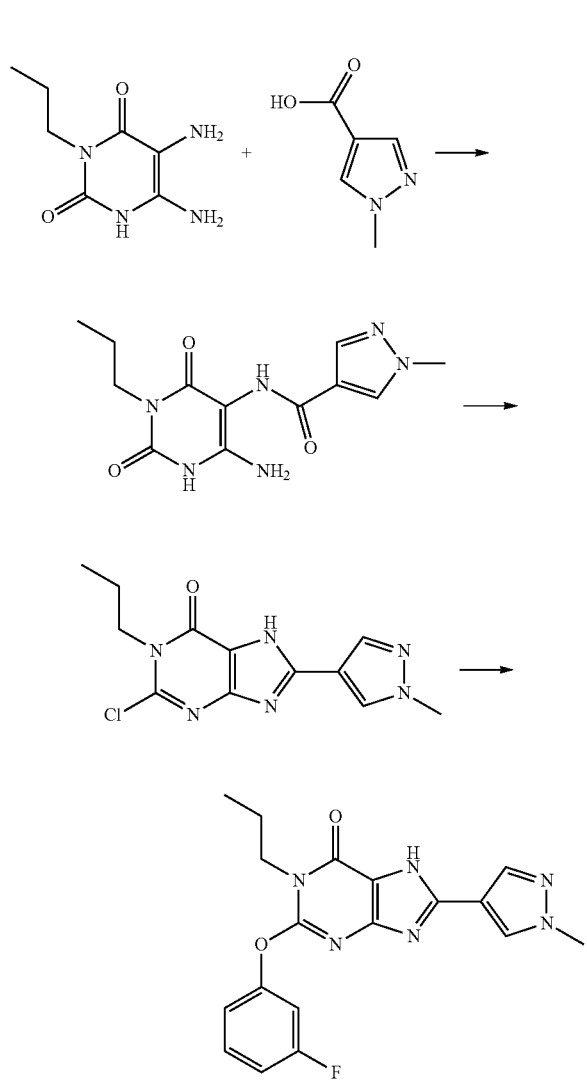

The first two steps were carried out as described earlier. A mixture of 2-Chloro-8-(1-methyl-1H-pyrazol-4-yl)-1-propyl-1,7-dihydro-purin-6-one (0.1 g, 0.34 mmol), N-methyl pyrrolidone (2 ml), potassium carbonate (0.093 g, 0.68 mmol) and 3-Fluoro phenol (0.036 ml, 0.4 mmol), were heated at 85-90° C. for 20 hours. The reaction mixture was cooled to 0° C. and then added water (10 ml). The solid obtained was filtered, washed with cold water, then washed with diethyl ether, dried to obtain -(3-Fluoro-phenoxy)-8-(1-methyl-1H-pyrazol-4-yl)-1-propyl-1,7dihydro-purin-6-one (0.093 g, 75%) as an off white solid.

$^1$HNMR (400 MHz, DMSO d6): δ 0.96 (t, J=7.2 Hz, 3H); 1.75-1.77 (m, 2H); 3.89 (s, 3H); 4.11-4.12 (m, 2H); 7.20-7.25 (m, 2H); 7.33-7.37 (m, 1H); 7.50-7.56 (m, 1H); 8.00 (s, 1H); 8.22 (s, 1H); 13.37 (bs, 1H).

Example 88

Preparation of 2-(4-methoxy-phenylamino)-8-(1-methyl-1H-pyrazol-4-yl)-1-propyl-1,7-dihydro-purin-6-one

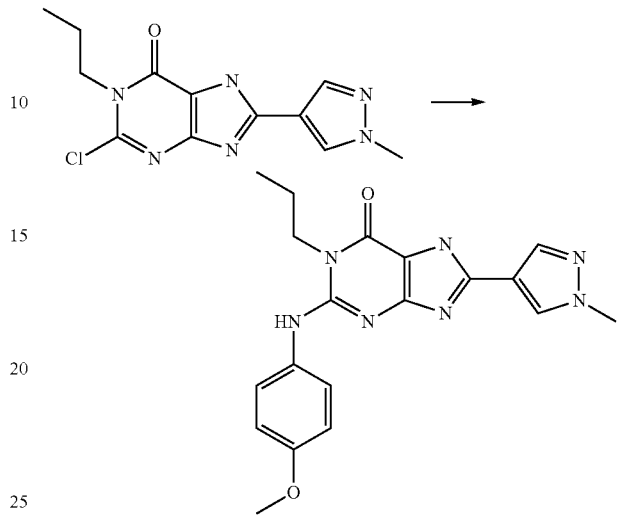

A mixture of 2-Chloro-8-(1-methyl-1H-pyrazol-4-yl)-1-propyl-1,7-dihydro-purin-6-one (0.1 g, 0.34 mmol), p-anisidine (0.049 g, 0.4 mmol) and 1-butanol (5 ml), were heated at reflux temperature for 20 hours. The reaction mixture was cooled to 20-25° C. and evaporated to dryness, then added water (20 ml) to the residue and extracted with ethyl acetate (4×20 ml). The organic layers were mixed and washed with brine (30 ml), dried over Na$_2$SO$_4$ and evaporated to dryness and the crude product was washed with diethyl ether and dried to obtain 2-(4-Methoxy-phenylamino)-8-(1-methyl-1H-pyrazol-4-yl)-1-propyl-1,7-dihydro-purin-6-one (0.0625 g, 48%) as an off white solid.

$^1$HNMR (400 MHz, CD$_3$OD): δ 1.04 (t, J=7.2 Hz, 3H); 1.80-1.82 (m, 2H); 4.21-4.23 (m, 2H); 4.59 (s, 6H); 6.92 (d, J=8.4 Hz, 2H); 7.38 (d, J=8.8 Hz, 2H); 7.96 (s, 1H); 8.09 (s, 1H).

Example 89

Preparation of 2-Methoxy-1-propyl-8-[1-(3-trifluoromethyl-benzyl)-1H-pyrazol-4-yl]-1,7-dihydro-purin-6-one

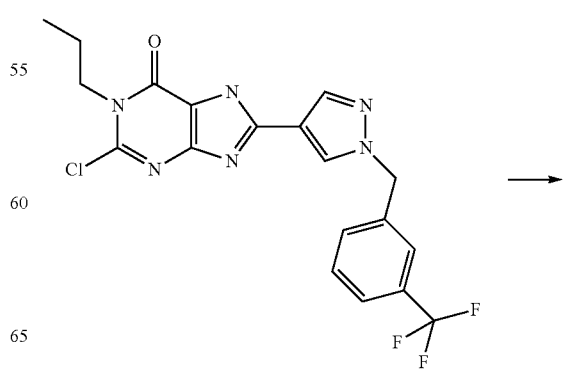

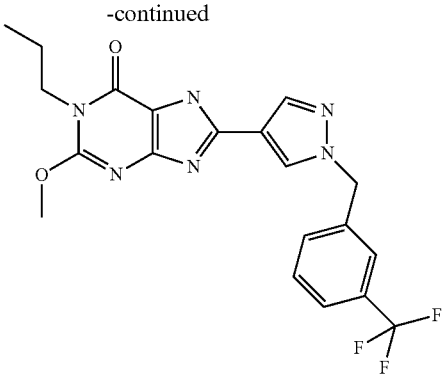

To the mixture of methanol (2 ml) and NaH (45 mg, 1.1 mmol), 2-Chloro-1-propyl-8-[1-(3-trifluoromethyl-benzyl)-1H-pyrazol-4-yl]-1,7-dihydro-purin-6-one (50 mg, 0.11 mmol) was added and refluxed for 2 hours at 80° C. Reaction mixture was cooled, diluted with ethyl acetate (10 ml) and quenched with saturated NH$_4$Cl solution. The organic layer was separated and washed with brine (2×10 ml), dried over Na$_2$SO$_4$, filtered and evaporated. The residue obtained was purified by preparative HPLC to obtain pure 2-Methoxy-1-propyl-8-[1-(3-trifluoromethyl-benz)-1H-pyrazol-4-yl]-1,7-dihydro-purin-6-one (26 mg, 53%) as an off white solid.

$^1$HNMR (400 MHz, CD$_3$OD): δ 0.87-0.96 (m, 3H); 1.68-1.71 (m, 2H); 4.02-4.25 (m, 5H); 5.50 (s, 2H); 7.54-7.61 (m, 4H); 8.07 (s, 1H); 8.30 (s, 1H)

Examples 90-93 were prepared in an analogous manner of Example 89 from appropriate intermediates.

| Example | IUPAC name |
|---|---|
| 90 | 2-Cyclopentyloxy-1-propyl-8-[1-(3-trifluoromethyl-benzyl)-1H-pyrazol-4-yl]-1,7-dihydro-purin-6-one |
| 91 | {6-Oxo-1-propyl-8-[1-(3-trifluoromethyl-benzyl)-1H-pyrazol-4-yl]-6,7-dihydro-1H-purin-2-yloxy}-acetic acid ethyl ester |
| 92 | 1-Propyl-2-(2,2,2-trifluoro-ethoxy)-8-[1-(3-trifluoromethyl-benzyl)-1H-pyrazol-4-yl]-1,7-dihydro-purin-6-one |
| 93 | 2-(2-Methoxy-ethoxy)-1-propyl-8-[1-(3-trifluoromethyl-benzyl)-1H-pyrazol-4-yl]-1,7-dihydro-purin-6-one |

Example 94

Preparation of 6-Oxo-1-propyl-8-[1-(3-trifluoromethyl-benzyl)-1H-pyrazol-4-yl]-6,7-dihydro-1H-purine-2-carboxylic acid amide

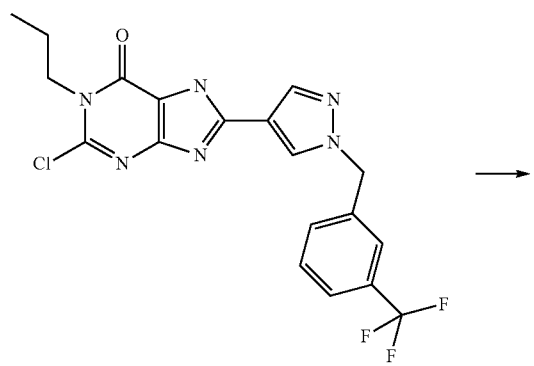

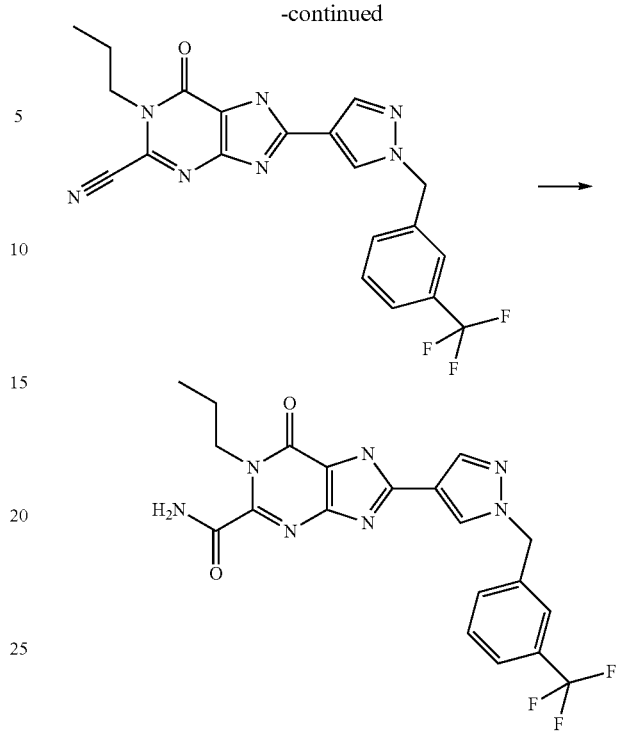

Step 1: 6-Oxo-1-propyl-8-[1-(3-trifluoromethyl-benzyl)-1H-pyrazol-4-yl]-6,7-dihydro-1H-purine-2-carbonitrile A mixture of 2-Chloro-1-propyl-8-[1-(3-trifluoromethyl-benzyl)-1H-pyrazol-4-yl]-1,7-dihydro-purin-6-one (4.0 g, 9.16 mmol), NaCN (0.67 g, 13.74 mmol), NaI (2.0 g, 9.16 mmol) and DMF (30 ml) were stirred for 48 hrs at 60° C. Reaction mixture was cooled to 20-25° C. and water was added and solid filtered off. The crude product was purified by column chromatography using silica gel (100-200 mesh) and 2 to 4% methanol in DCM as an eluent to obtain 6-Oxo-1-propyl-8-[1-(3-trifluoromethyl-benzyl)-1H-pyrazol-4-yl]-6,7-dihydro-1H-purine-2-carbonitrile (2.6 g, 67%) as an off white solid.

$^1$HNMR (400 MHz, DMSO d6): δ 0.92 (t, J=7.2 Hz, 3H); 1.71-1.77 (m, 2H); 4.12 (t, J=7.6 Hz, 2H); 5.51 (s, 2H); 7.57-7.67 (m, 4H); 8.14 (s, 1H); 8.55 (s, 1H); 14.01 (bs, 1H)

Step 2: 6-Oxo-1-propyl-8-[1-(3-trifluoromethyl-benzyl)-1H-pyrazol-4-yl]-6,7-dihydro-1H-purine-2-carboxylic acid amide A mixture of 6-Oxo-1-propyl-8-[1-(3-trifluoromethyl-benzyl)-1H-pyrazol-4-yl]-6,7-dihydro-1H-purine-2-carbonitrile (40 mg, 0.0934 mmol), NaOH (6 mg, 0.140 mmol) and Ethanol:water (3:1) (2 ml) were stirred at 50° C. for 18 hours. Reaction mixture was cooled and organic volatiles were evaporated and the residue obtained was dissolved in DCM (10 ml) and washed with brine (10 ml). Organic layer was dried over Na$_2$SO$_4$ and evaporated to obtain pure 6-Oxo-1-propyl-8-[1-(3-trifluoromethyl-benzyl)-1H-pyrazol-4-yl]-6,7-dihydro-1H-purine-2-carboxylic acid amide (32 mg, 78%) as an off white solid.

$^1$HNMR (400 MHz, CD$_3$OD): δ 0.96 (t, J=7.6 Hz, 3H); 1.78-1.84 (m, 2H); 4.22 (t, J=8 Hz, 2H); 5.51 (s, 2H); 7.55-7.61 (m, 4H); 8.13 (s, 1H); 8.34 (s, 1H).

Example 95

8-[1-(3-Fluoro-4-trifluoromethyl-benzyl)-1H-pyrazol-4-yl]-6-oxo-1-propyl-6,7-dihydro-1H-purine-2-carbonitrile Obtained following analogous procedure of Example 94 starting from appropriate intermediates.

$^1$HNMR (400 MHz, CD$_3$OD): 1.03 (t, J=7.6 Hz, 3H); 1.85-1.87 (m, 2H); 4.28 (t, J=7.6 Hz, 2H); 5.52 (s, 2H); 7.22-7.24 (m, 2H); 7.65-7.69 (m, 1H); 8.14 (s, 1H); 8.39 (s, 1H).

Example 96

8-[1-(3-Fluoro-4-trifluoromethyl-benzyl)-1H-pyrazol-4-yl]-6-oxo-1-propyl-6,7-dihydro-1H-purine-2-carboxylic acid

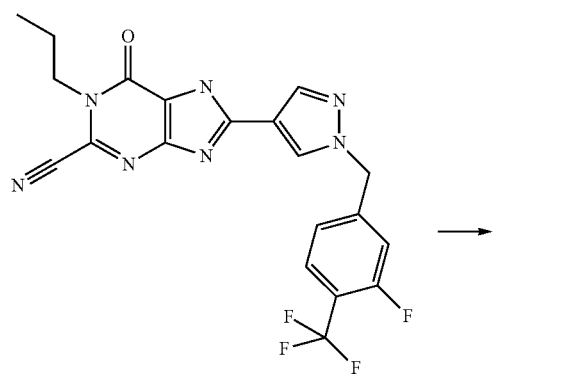

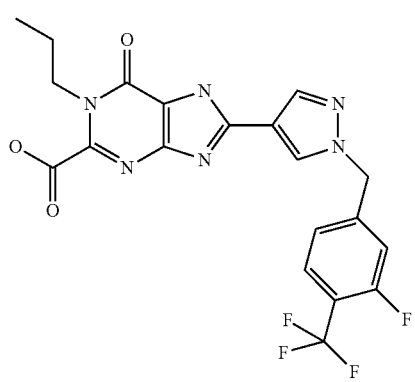

A mixture of 8-[1-(3-Fluoro-4-trifluoromethyl-benzyl)-1H-pyrazol-4-yl]-6-oxo-1-propyl-6,7-dihydro-1H-purine-2-carbonitrile (65 mg, 0.145 mmol), NaOH (11 mg, 0.290 mmol) and Ethanol:water (3:1) (6 ml) were stirred at 55-60° C. for 2 hours. Reaction mixture was cooled and organic volatiles were evaporated and to the residue water (2 ml) was added and acidified by 2N HCl up to pH (1-2), solid filtered off. The crude product was purified by preparative HPLC to obtain pure 8-[1-(3-Fluoro-4-trifluoromethyl-benzyl)-1H-pyrazol-4-yl]-6-oxo-1-propyl-6,7-dihydro-1H-purine-2-carboxylic acid (21 mg, 31%) as a white solid.

$^1$HNMR (400 MHz, CD$_3$OD): δ0.98 (t, J=9.2 Hz, 3H); 1.68-1.74 (m, 2H); 3.99 (t, J=7.2 Hz, 2H); 5.50 (s, 2H); 7.54-7.61 (m, 4H); 8.07 (s, 1H); 8.28 (s, 1H).

Example 97

7-Methyl-1-propyl-8-[1-(3-trifluoromethyl-benzyl)-1H-pyrazol-4-yl]-1,7-dihydro-purin-6-one

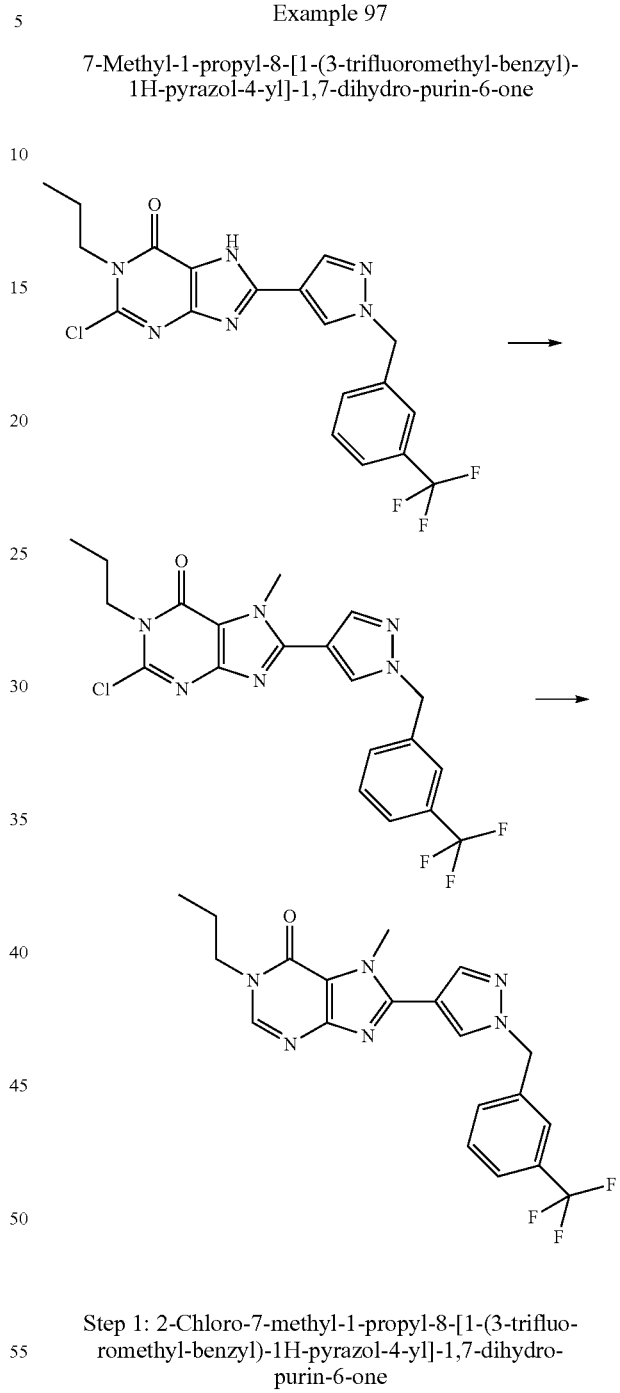

Step 1: 2-Chloro-7-methyl-1-propyl-8-[1-(3-trifluoromethyl-benzyl)-1H-pyrazol-4-yl]-1,7-dihydro-purin-6-one A mixture of 2-Chloro-1-propyl-8-[1-(3-trifluoromethyl-benzyl)-1H-pyrazol-4-yl]-1,7-dihydro-purin-6-one (200 mg, 0.46 mmol), K$_2$CO$_3$ (95 mg, 0.69 mmol), MeI (85 mg, 0.60 mmol) and DMF (2 ml) were stirred at 60° C. for 2 hours. Reaction mixture was cooled, diluted with water (10 ml) and extracted with ethyl acetate (2×5 ml). The organic layer was washed with brine (2×10 ml), dried over Na$_2$SO$_4$ and evaporated to obtain 2-Chloro-7-methyl-1-propyl-8-[1-(3-trifluoromethyl-benzyl)-1H-pyrazol-4-yl]-1,7-dihydro-purin-6-one (120 mg, 58%)

¹HNMR (400 MHz, DMSO d6): δ 0.91-0.95 (m, 3H); 1.66-1.71 (m, 2H); 4.12 (s, 3H); 4.15-4.18 (m, 2H); 5.55 (s, 2H); 7.62-7.63 (m, 2H); 7.69-7.72 (m, 2H); 8.12 (s, 1H); 8.68 (s, 1H)

Step 2: Preparation of 7-Methyl-1-propyl-8-[1-(3-trifluoromethyl-benzyl)-1H-pyrazol-4-yl]-1,7-dihydro-purin-6-one Step-2 was carried out as described in Step-5 of Example 28

¹HNMR (400 MHz, CD₃OD): δ 0.87 (t, J=7.6 Hz, 3H); 1.66-1.71 (m, 2H); 3.84 (s, 3H); 3.97 (t, J=7.6 Hz, 2H); 5.56 (s, 2H); 7.61-7.63 (m, 2H); 7.69-7.71 (m, 2H); 8.11 (s, 1H); 8.39 (s, 1H); 8.66 (s, 1H)

Example 98

2-Chloro-8-[1-(3-fluoro-4-trifluoromethyl-benzyl)-1H-pyrazol-4-yl]-7-methyl-1-propyl-1,7-dihydro-purin-6-one Obtained following analogous procedure of Example 97 starting from appropriate intermediates.
¹HNMR (400 MHz, DMSO d6): δ 0.94 (t, J=7.2 Hz, 3H); 1.71-1.74 (m, 2H); 4.14-4.20 (m, 5H); 5.59 (s, 2H); 7.31 (d, J=7.6 Hz, 1H); 7.45 (d, J=12 Hz, 1H); 7.82 (dd, J=7.6 Hz, 1H); 8.15 (d, J=6 Hz, 1H); 8.69 (d, J=13.6 Hz, 1H);

Example 99

Preparation of {6-Oxo-1-propyl-8-[1-(3-trifluoromethyl-benzyl)-1H-pyrazol-4-yl]-6,7-dihydro-1H-purin-2-yloxy}-acetic acid A mixture of {6-Oxo-1-propyl-8-[1-(3-trifluoromethyl-benzyl)-1H-pyrazol-4-yl]-6,7-dihydro-1H-purin-2-yloxy}-acetic acid ethyl ester (56 mg, 0.11 mmol), LiOH:6H₂O (14 mg, 0.33 mmol) and THF:MeOH:Water (3:2:1) (1 ml) were stirred for 3 hours at ambient temperature. Organic volatiles were evaporated and the residue was acidified with 1N HCl to obtain {6-Oxo-1-propyl-8-[1-(3-trifluoromethyl-benzyl)-1H-pyrazol-4-yl]-6,7-dihydro-1H-purin-2-yloxy}-acetic acid as an off white solid (20 mg, 38%)
¹HNMR (400 MHz, CD₃OD): δ 0.99 (t, J=7.6 Hz, 3H); 1.77-1.82 (m, 2H); 4.13 (t, J=7.6 Hz, 2H); 5.03 (s, 2H); 5.54 (s, 2H); 7.59-7.67 (m, 4H); 8.12 (s, 1H); 8.36 (s, 1H)

Example 100

Preparation of 2-Difluoromethoxy-1-propyl-8-[1-(3-trifluoromethyl-benzyl)-1H-pyrazol-4-yl]-1,7-dihydro-purin-6-one

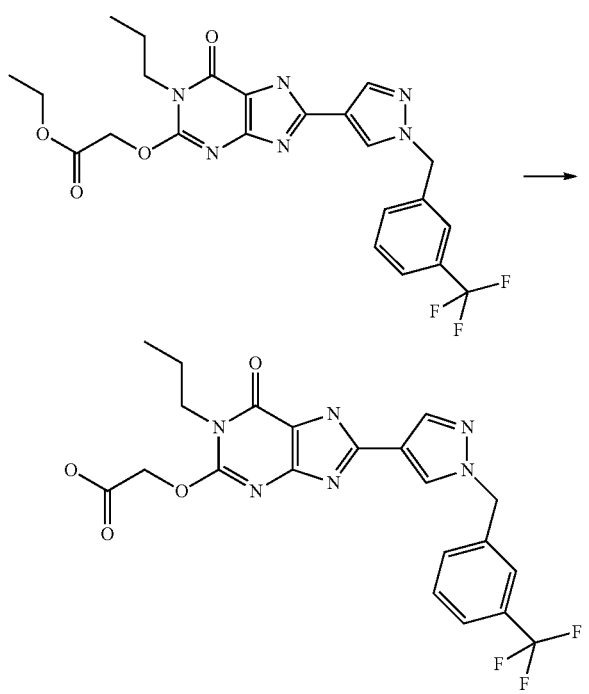

A mixture of 1-Propyl-8-[1-(3-trifluoromethyl-benzyl)-1H-pyrazol-4-yl]-3,7-dihydro-purine-2,6-dione (100 mg, 0.24 mmol), Sodium chloro difluoroacetate (47 mg, 0.31 mmol), Cs₂CO₃ (117 mg, 0.36 mmol) and DMF (2 ml) were stirred at 60° C. for 18 hours. Reaction mixture was cooled and diluted with water (10 ml), solid materials were filtered off and it was purified by preparative HPLC to obtain 2-Difluoromethoxy-1-propyl-8-[1-(3-trifluoromethyl-benzyl)-1H-pyrazol-4-yl]-1,7-dihydro-purin-6-one as off white solid (1 mg, 10%) and ¹HNMR (400 MHz, DMSO d6): δ 0.86 (t, J=7.6 Hz, 3H); 1.53-1.58 (m, 2H); 3.79 (t, J=7.6 Hz, 2H); 5.56 (s, 2H); 7.60-7.61 (m, 2H); 7.68-7.70 (m, 2H); 7.99 (s, 1H); 8.16 (t, J=55.8 Hz, 1H); 8.6 (s, 1H); 12.22 (bs, 1H)

3-Difluoromethyl-1-propyl-8-[1-(3-trifluoromethyl-benzyl)-1H-pyrazol-4-yl]-3,7-dihydro-purine-2,6-dione ¹HNMR (400 MHz, DMSO d6): δ 0.87 (t, J=7.6 Hz, 3H); 1.53-1.58 (m, 2H); 3.79-3.83 (m, 2H); 5.55 (s, 2H); 7.60-7.71 (m, 4H); 7.80 (t, J=55.6.8 Hz, 1H); 7.90 (s, 1H); 8.46 (s, 1H); 12.44 (bs, 1H)

Example 101

Preparation of 1-Propyl-8-(1-pyridin-3-ylmethyl-1H-pyrazol-4-yl)-1,7-dihydro-purin-6-one

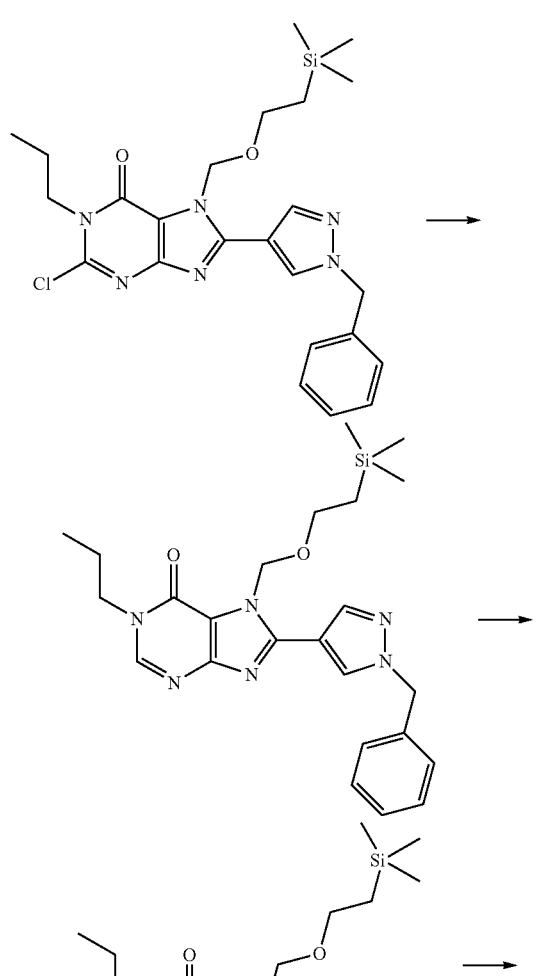

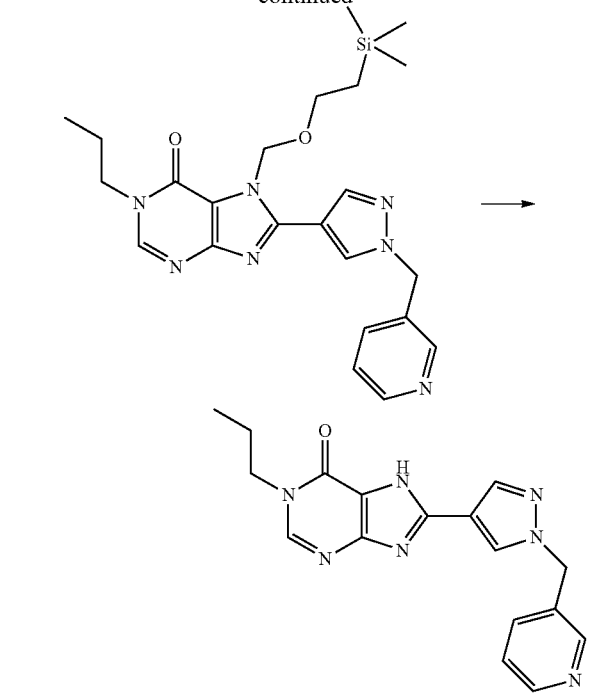

Step 1: 8-(1-Benzyl-1H-pyrazol-4-yl)-1-propyl-7-(2-trimethylsilanyl-ethoxymethyl)-1,7-dihydro-purin-6-one Step-1 was carried out as described in Step-5 of Example 28

Step 2: 1-Propyl-8-(1H-pyrazol-4-yl)-7-(2-trimethyl-silanyl-ethoxymethyl)-1,7-dihydro-purin-6-one Step-2 was carried out as described in Step-3 of Example 27

Step 3: 1-Propyl-8-(1-pyridin-3-ylmethyl-1H-pyrazol-4-yl)-7-(2-trimethylsilanyl-ethoxymethyl)-1,7-dihydro-purin-6-one A mixture of 1-Propyl-8-(1H-pyrazol-4-yl)-7-(2-trimethylsilanyl-ethoxymethyl)-1,7-dihydro-purin-6-one (100 mg, 0.2 mmol), 3-Bromomethylpyridine (55 mg, 0.3 mmol), K₂CO₃ (50 mg, 0:3 mmol) and DMF were stirred at 60° C. for 2 hours. Organic volatiles were evaporated and purified to obtain pure 1-Propyl-8-(1-pyridin-3-ylmethyl-1H-pyrazol-4-yl)-7-(2-trimethylsilanyl-ethoxymethyl)-1,7-dihydro-purin-6-one (8 mg, 6%) as an colourless oil.

Step 4: 1-Propyl-8-(1-pyridin-3-ylmethyl-1H-pyrazol-4-yl)-1,7-dihydro-purin-6-one Step-4 was carried out as described in Step-5 of Example 15

¹HNMR (400 MHz, DMSO d6): δ 0.99 (t, J=7.6 Hz, 3H); 1.80-1.86 (m, 2H); 4.10 (t, J=7.2 Hz, 2H); 5.81 (s, 2H); 8.11-8.14 (dd, J=8.8 Hz, 4.2 Hz, 1H); 8.26 (s, 1H); 8.46 (s, 1H); 8.63 (d, J=8.4 Hz, 1H); 8.73 (s, 1H); 8.88 (d, J=4.8 Hz, 1H); 8.98 (s, 1H)

Example 102

1-Propyl-8-[1-(6-trifluoromethyl-pyridin-3-ylmethyl)-1H-pyrazol-4-yl]-1,7-dihydro-purin-6-one Obtained following analogous procedure of Example 101 starting from appropriate intermediates.

¹HNMR (400 MHz, DMSO d6): δ 0.87 (t, J=7.6 Hz, 3H); 1.66-1.71 (m, 2H); 3.96 (t, J=7.6 Hz, 2H); 5.63 (s, 2H); 7.91-7.94 (m, 2H); 8.20 (s, 1H); 8.36 (s, 1H); 8.60 (s, 1H); 8.75 (s, 1H)

Example 103

Preparation of 8-{1-[1-(2,4-Difluoro-phenyl)-5-oxo-pyrrolidin-3-ylmethyl]-1H-pyrazol-4-yl}-1-propyl-1,7-dihydro-purin-6-one

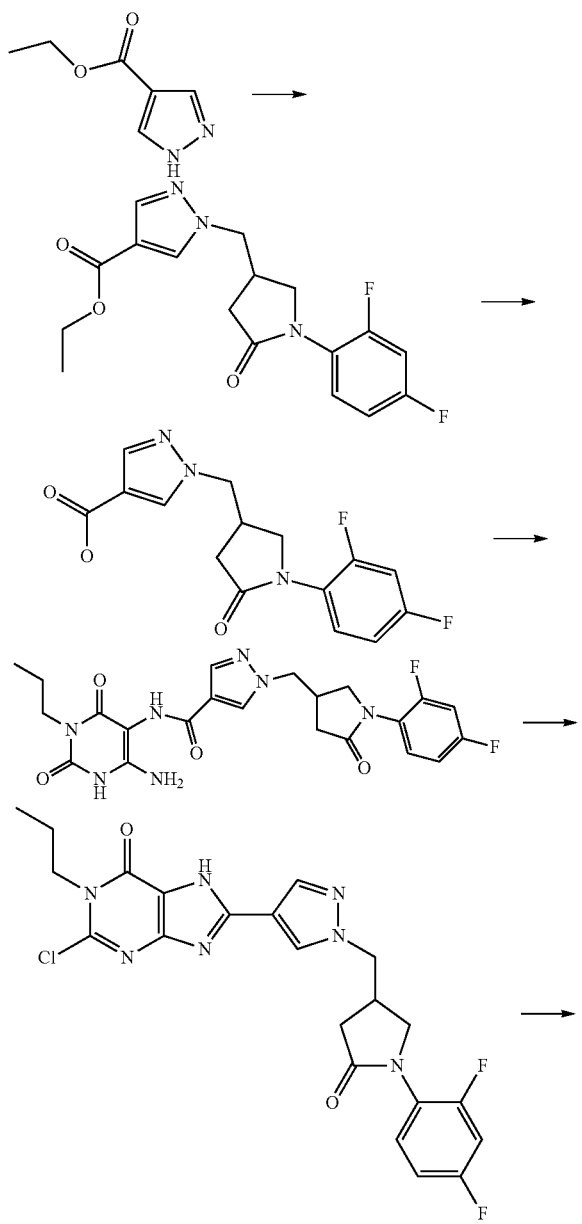

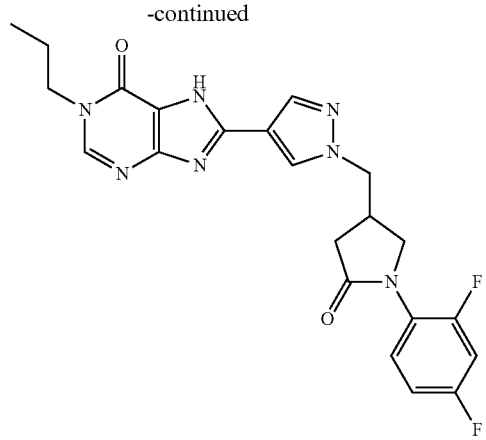

Step 1: 1-[1-(2,4-Difluoro-phenyl)-5-oxo-pyrrolidin-3-ylmethyl]-1H-pyrazole-4-carboxylic acid ethyl ester A mixture of 1H-Pyrazole-4-carboxylic acid ethyl ester (0.100 g, 0.713 mmol), potassium carbonate (0.019 g, 1.42 mmol), Methanesulfonic acid 1-(2,4-difluoro-phenyl)-5-oxo-pyrrolidin-3-ylmethyl ester (0.32 g, 1.07 mmol) were taken in DMF (2 ml). The reaction mixture was heated at 55-60° C. for 20 hour. The mixture was cooled to room temperature and then to this reaction mixture water (20 ml) was added and extracted with ethyl acetate (3×25 ml), organic layers were combined and washed with brine (25 ml), dried over Na₂SO₄ and evaporated to dryness to obtain 1-[1-(2,4-Difluoro-phenyl)-5-oxo-pyrrolidin-3-ylmethyl]-1H-pyrazole-4-carboxylic acid ethyl ester (0.22 g, 91%) as a brownish sticky mass.

¹HNMR (400 MHz, CDCl₃): δ 1.36 (t, J=6.8 Hz, 3H); 2.39 (dd, J=6.0, 17.2 Hz, 1H); 2.78 (dd, J=8.8, 17.2 Hz, 1H); 3.17-3.22 (m, 1H); 3.62 (dd, J=4.8, 10.0 Hz, 1H); 3.86 (dd, J=7.6, 10.0 Hz, 1H); 4.27-4.34 (m, 4H); 6.90-6.94 (m, 2H); 7.32-7.38 (m, 1H); 7.94 (s, 1H); 8.04 (s, 1H).

Step 2: 1-[1-(2,4-Difluoro-phenyl)-5-oxo-pyrrolidin-3-ylmethyl]-1H-pyrazole-4-carboxylic acid 1-[1-(2,4-Difluoro-phenyl)-5-oxo-pyrrolidin-3-ylmethyl]-1H-pyrazole-4-carboxylic acid ethyl ester (0.222 g, 0.62 mmol) was dissolved in a mixture of solvents Methanol:water (3:1, 5 ml) and KOH (0.07 g, 125 mmol) was added to the reaction mixture and then stirred at 50-55° C. for 3 hours. Solvents were removed and the residue was diluted with water (3 ml) and washed with DCM (3×10 ml) and acidified with dil. HCl. It was extracted with ethyl acetate (3×15 ml), organic layers were mixed and washed with brine (20 ml), dried over Na₂SO₄ and evaporated to dryness to obtain 1-[1-(2,4-Difluoro-phenyl)-5-oxo-pyrrolidin-3-ylmethyl]-1H-pyrazole-4-carboxylic acid (0.18 g, 90%) as a brownish sticky mass.

¹HNMR (400 MHz, CDCl₃): δ 2.42 (dd, J=4.4, 17.6 Hz, 1H); 2.80 (dd, J=8.8, 17.6 Hz, 1H); 3.17-3.25 (m, 1H); 3.63-3.67 (m, 1H); 3.87-3.91 (m, 1H); 4.32-4.34 (m, 2H); 6.91-6.96 (m, 2H); 7.34-7.38 (m, 1H); 8.01 (s, 1H); 8.04 (s, 1H).

Step 3: 1-[1-(2,4-Difluoro-phenyl)-5-oxo-pyrrolidin-3-ylmethyl]-1H-pyrazole-4-carboxylic acid (6-amino-2,4-dioxo-3-propyl-1,2,3,4-tetrahydro-pyrimidin-5-yl)-amide A mixture of 5,6-Diamino-3-propyl-1H-pyrimidine-2,4-dione (0.12 g, 0.67 mmol) and 1-[1-(2,4-Difluoro-phenyl)-5- oxo-pyrrolidin-3-ylmethyl]-1H-pyrazole-4-carboxylic acid (0.18 g, 0.56 mmol) in methanol (6 ml) was cooled to 0° C. and added EDCI.HCl (0.15 g, 0.78 mmol) and stirred at 25° C. for 20 hours. Solvents were removed under reduced pressure and to this reaction mixture water (10 ml) was added. Solid obtained was filtered off and washed with cold water (20 ml) followed by diethyl ether (25 ml). It was then dried and the crude product was purified by column chromatography using silica gel (100-200 mesh) and 6% methanol in DCM as an eluent to obtain 1-[1-(2,4-Difluoro-phenyl)-5-oxo-pyrrolidin-3-ylmethyl]-1H-pyrazole-4-carboxylic acid (6-amino-2,4-dioxo-3-propyl-1,2,3,4-tetrahydro-pyrimidin-5-yl)-amide (0.165 g, 60%) as an off white solid.

$^1$HNMR (400 MHz, DMSO d6): δ 0.82 (t, J=7.2 Hz, 3H); 1.46-1.51 (m, 2H); 2.31 (dd, J=6.4, 16.8 Hz, 1H); 2.58 (dd, J=8.8, 16.8 Hz, 1H); 3.02-3.04 (m, 1H); 3.55 (dd, J=5.6, 9.6 Hz, 1H); 3.64 (t, J=8.0 Hz, 2H); 3.78 (t, J=8.0 Hz, 1H); 4.31 (d, J=7.2 Hz, 2H); 5.99 (s, 2H); 7.12-7.17 (m, 1H); 7.33-7.39 (m, 1H); 7.44-7.48 (m, 1H); 7.98 (s, 1H); 8.30 (s, 1H); 8.53 (s, 1H); 10.42 (s, 1H).

Step 4: 2-Chloro-8-{1-[1-(2,4-difluoro-phenyl)-5-oxo-pyrrolidin-3-ylmethyl]-1H-pyrazol-4-yl}-1-propyl-1,7-dihydro-purin-6-one A mixture of 1-[1-(2,4-Difluoro-phenyl)-5-oxo-pyrrolidin-3-ylmethyl]-1H-pyrazole-4-carboxylic acid (6-amino-2,4-dioxo-3-propyl-1,2,3,4-tetrahydro-pyrimidin-5-yl)-amide (0.165 g, 0.338 mmol), phenyl phosphoric dichloride (5 ml) were heated at 125-130° C. for 30 hours. Reaction mixture was cooled to 20-25° C. and then solvents were removed under reduced pressure and residue was washed with diethyl ether. The crude product was purified by column chromatography using silica gel (100-200 mesh) and 4-5% methanol in DCM as an eluent to obtain 2-Chloro-8-{1-[1-(2,4-difluoro-phenyl)-5-oxo-pyrrolidin-3-ylmethyl]-1H-pyrazol-4-yl}-1-propyl-1,7-dihydro-purin-6-one (0.04 g, 24%) as a yellow solid.

$^1$HNMR (400 MHz, CD$_3$OD): δ 0.92 (t, J=7.2 Hz, 3H); 1.69-1.73 (m, 2H); 2.39-2.45 (m, 1H); 2.62-2.68 (m, 1H); 3.10-3.14 (m, 1H); 3.60-3.65 (m, 1H); 3.80-3.85 (m, 1H); 4.34 (t, J=7.2 Hz, 2H); 4.46-4.48 (m, 2H); 6.89-6.83 (m, 1H); 6.96-7.01 (m, 1H); 7.29-7.33 (m, 1H); 8.13 (s, 1H); 8.36 (s, 1H).

Step 5: 8-{1-[1-(2,4-Difluoro-phenyl)-5-oxo-pyrrolidin-3-ylmethyl]-1H-pyrazol-4-yl}-1-propyl-1,7-dihydro-purin-6-one A mixture of 2-Chloro-8-{1-[1-(2,4-difluoro-phenyl)-5-oxo-pyrrolidin-3-ylmethyl]-1H-pyrazol-4-yl}-1-propyl-1,7-dihydro-purin-6-one (25.0 mg, 0.051 mmol), Pd/C (10%) (5.0 mg), DMF (1 ml) and H$_2$O (0.25 ml) and ammonium formate (64 mg, 1.02 mmol) were heated at 85-90° C. for 1 hour. Reaction mixture was cooled to 20-25° C. and then it was filtered through celite bed, washed with methanol (10 ml). Solvents were removed under reduced pressure and to this residue water (1 ml) was added and acidified with citric acid to get pH (1-2). Solid obtained was filtered off and washed with cold water, followed by diethyl ether. Solid crude product was purified by column chromatography using preparative TLC to obtain 8-{1-[1-(2,4-Difluoro-phenyl)-5-oxo-pyrrolidin-3-ylmethyl]-1H-pyrazol-4-yl}-1-propyl-1,7-dihydro-purin-6-one (5.5 mg, 33%) as a pale yellow solid.

$^1$HNMR (400 MHz, CD$_3$OD): δ 1.00 (t, J=7.2 Hz, 3H); 1.80-1.86 (m, 2H); 2.52 (dd, J=6.4, 17.2 Hz, 1H); 2.76 (dd, J=8.8, 17.2 Hz, 1H); 3.18-3.23 (m, 1H); 3.72 (dd, J=5.6, 10.0 Hz, 1H); 3.93 (dd, J=8.0, 10.0 Hz, 1H); 4.08 (t, J=7.6 Hz, 2H); 4.44 (d, J=7.2 Hz, 2H); 7.00-7.04 (m, 1H); 7.07-7.13 (m, 1H); 7.40-7.46 (m, 1H); 8.13 (s, 1H); 8.26 (s, 1H); 8.34 (s, 1H).

Biological Activity

Radioligand Binding for A$_{2B}$ Adenosine Receptor

Human A$_{2B}$ adenosine receptor cDNA was stably transfected into HEK-293 cells. HEK-A2B cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM Tris (pH 7.4). The cells were sonicated on ice for 6 min with six intermittent pulses of 9 second each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4), 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 1.6 nM [$^3$H]-MRS-1754 with various concentrations of test compounds and 10 μg membrane protein in Reaction buffer (50 mM Tris pH 6.5, 5 mM MgCl$_2$, 1 mM EDTA) supplemented with 1 U/ml Adenosine deaminase. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 μM NECA. Radioligand binding was read at Liquid scintillation counter (Perkin Elmer) and the affinities of compounds (i.e. K$_i$ values) were calculated using GraphPad software.

Compounds tested had micromolar to nanomolar activity.

Radioligand Binding for A$_1$ Adenosine Receptor

Human A$_1$ adenosine receptor cDNA was stably transfected into HEK-293 cells. HEK-A$_1$ cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM Tris (pH 7.4). The cells were sonicated on ice for 6 min with six intermittent pulses of 9 seconds each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4), 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, (pH-7.4) supplemented with 1 Unit/ml ADA and 10% sucrose. Frozen aliquots were stored at −80° C.

Competition assays were started by mixing 1 nM [$^3$H]-DPCPX with various concentrations of test compounds and 5 μg membrane protein in Reaction buffer (50 mM Tris pH 7.4, 1 mM EDTA) supplemented with 1 Unit/ml ADA. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 μM NECA. Radioligand binding was read at Liquid scintillation counter (Perkin Elmer) and the affinities of compounds (i.e. $K_i$ values) were calculated using Graph-Pad software.

Compounds tested had micromolar to nanomolar activity.

Radioligand Binding for $A_{2A}$ Adenosine Receptor

Human $A_{2A}$ adenosine receptor cDNA was stably transfected into HEK-293 cells. HEK-A2A cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM (Tris pH 7.4). The cells were sonicated on ice for 6 min with six intermittent pulses of 9 second each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4) supplemented with 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 2 nM [$^3$H]-ZM-241385 with various concentrations of test compounds and 5 μg membrane protein in Reaction buffer (50 mM Tris pH 7.4, 1 mM EDTA) supplemented with 1 Unit/ml ADA. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 μM NECA. Radioligand binding was read at Liquid scintillation counter (Perkin Elmer) and the affinities of compounds (i.e. $K_i$ values) were calculated using GraphPad software.

Compounds tested had micromolar to nanomolar activity.

Radioligand Binding for $A_3$ Adenosine Receptor

Human $A_3$ adenosine receptor cDNA was stably transfected into HEK-293 cells. HEK-$A_3$ cells were harvested by trypsinization with 0.25% Trypsin-EDTA (Sigma), and washed in 1×PBS at 1500 rpm for 5 minutes at room temperature. The cells were washed twice in wash buffer containing 10 mM EDTA, 10 mM HEPES (pH-7.4) at 1500 rpm for 10 minutes at room temperature and incubated for 10 min at 4° C. in sonication buffer containing 1 mM EDTA, 10 mM HEPES (pH 7.4). The cells were sonicated on ice for 6 min with six intermittent pulses of 9 seconds each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 10 mM HEPES (pH 7.4) supplemented with 1 Unit/ml adenosine deaminase (ADA) and incubated for 30 minutes at room temperature. The lysate was washed twice with buffer containing 1 mM EDTA, 10 mM HEPES (pH-7.4) at 49,000×g for 45 minutes at 4° C. and the protein pellet was resuspended in buffer containing 1 mM EDTA, 5 mM Tris (pH-7.4) supplemented with 1 Unit/ml ADA and 10% sucrose. Frozen aliquots were stored at −80° C.

Competition assays were started by mixing 2 nM [3H]-HEM-ADO with various concentrations of test compounds and 5 μg membrane protein in Reaction buffer (50 mM Tris pH 7.4, 1 mM EDTA, 10 mM $MgCl_2$) supplemented with 1 Unit/ml ADA. The assay reactions were incubated for 90 minutes at room temperature and stopped by filtration using 96 well-plate harvester (Molecular Devices) and washed four times with ice cold 50 mM Tris pH 7.4. Non specific binding was determined in presence of 200 M NECA. Radioligand binding was read at Liquid scintillation counter (Perkin Elmer) and the affinities of compounds (i.e. $K_i$ values) were calculated using GraphPad software.

Compounds tested had micromolar to nanomolar activity.

Although the subject matter has been described in considerable detail with reference to certain preferred embodiments thereof, other embodiments are possible. As such, the spirit and scope of the appended claims should be limited to the description of the preferred embodiment contained therein.

We claim:

1. A compound of formula (I)

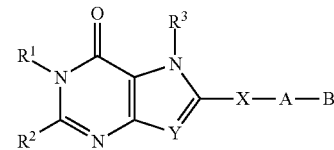

or its tautomers, stereoisomers, or pharmaceutically acceptable salts thereof, wherein Y is N or CR; R is H, hydroxy, alkoxy, alkyl, or aryl;

$R^1$ is selected from the group consisting of alkyl, alkenyl and alkynyl, wherein one or more methylene groups are optionally replaced by hetero atoms or groups selected from —O—, —S(O)$_p$—, —N($R^a$)—, or —C(O), provided that the heteroatom is not adjacent to N in the ring; p is 0, 1 or 2;

wherein alkyl, alkenyl and alkynyl are unsubstituted or substituted independently with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy, carboxyalkyl, —SO$_3$H, aminocarbonylamino, hydroxyamino, alkoxyamino, nitro, —S(O)$_2$NR$^a$R$^a$, —NR$^a$S(O)$_2$R$^a$, or —S(O)$_p$R$^a$;

$R^2$ is selected from the group consisting of halogen, cyano, nitro, carboxy, acyl, aminocarbonyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, arylalkyl, and aryloxy;

wherein alkoxy, carboxyalkyl, cycloalkyl, cycloalkylalkyl, cycloalkyloxy, arylalkyl, aryloxy, and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxy, alkoxy, halogen, haloalkyl, haloalkoxy, amino, substituted amino, cyano and —S(O)$_p$R$^d$;

R$^3$ is selected from the group consisting of hydrogen, alkyl, alkenyl, alkynyl, alkoxyalkyl, cycloalkyl, cycloalkylalkyl, aryl, arylalkyl, heteroaryl and heteroarylalkyl;

wherein alkyl, alkenyl, alkynyl, alkoxyalkyl, cycloalkyl, cycloalkylalkyl, aryl, arylalkyl, heteroaryl, and heteroarylalkyl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxy, alkoxy, halogen, haloalkyl, haloalkoxy, amino, substituted amino, cyano and —S(O)$_p$R$^d$;

X is optionally substituted arylene or optionally substituted heteroarylene;

A is (C$_1$-C$_6$)alkylene, (C$_2$-C$_6$)alkenylene or (C$_2$-C$_6$)alkynylene group, wherein 1 to 4 methylene groups are optionally replaced by groups independently selected from the group consisting of O, —S(O)$_p$—, —N(R$^b$)—, and —C(O)—;

wherein alkylene, alkenylene, and alkynylene are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxy, alkoxy, halogen, CF$_3$, amino, substituted amino, cyano and —S(O)$_p$R$^d$;

B is heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano and —S(O)$_p$R$^d$;

R$^a$ is independently selected from the group consisting of hydrogen and alkyl;

R$^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

R$^c$ is selected from the group consisting of hydrogen, alkyl, aryl, heteroaryl and heterocyclyl;

R$^d$ is selected from the group consisting of alkyl, cycloalkyl, aryl, heterocyclyl and heteroaryl;

and p is 0, 1 or 2.

2. A compound of formula (I) as claimed in claim 1 or its tautomers, stereoisomers, or pharmaceutically acceptable salts thereof, wherein Y is N;

R$^1$ is selected from the group consisting of alkyl, alkenyl and alkynyl, wherein alkyl, alkenyl and alkynyl are unsubstituted or substituted independently with alkoxy, acyl, acylamino, acyloxy, amino, monoalkylamino, dialkylamino, aminocarbonyl, alkoxycarbonylamino, azido, cyano, halogen, haloalkyl, hydroxyl, hydroxyalkyl, keto, thiocarbonyl, carboxy, alkylcarboxy or carboxyalkyl;

R$^2$ is selected from the group consisting of halogen, cyano, nitro, carboxy, acyl, aminocarbonyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, arylalkyl, and aryloxy;

wherein alkoxy, carboxyalkyl, cycloalkyl, cycloalkylalkyl, cycloalkyloxy, arylalkyl, aryloxy, and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxyl, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxyl, alkoxy, halogen, haloalkyl, haloalkoxy, amino, substituted amino, cyano and —S(O)$_p$R$^d$;

R$^3$ is selected from the group consisting of hydrogen, alkyl, alkenyl, alkynyl, alkoxyalkyl, cycloalkyl, cycloalkylalkyl, aryl, arylalkyl, heteroaryl and heteroarylalkyl;

wherein alkyl, alkenyl, alkynyl, alkoxyalkyl, cycloalkyl, cycloalkylalkyl, aryl, arylalkyl, heteroaryl, and heteroarylalkyl are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxyl, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, $S(O)_2NR^cR^c$, $-NR^cS(O)_2R^c$ or $-S(O)_pR^d$;

wherein each substituent is unsubstituted or substituted with 1, 2, or 3 substituents independently selected from the group consisting of alkyl, carboxy, carboxyalkyl, aminocarbonyl, hydroxy, alkoxy, halogen, $CF_3$, amino, substituted amino, cyano or $-S(O)_pR^d$;

X is optionally substituted arylene or optionally substituted heteroarylene;

A is $(C_1-C_6)$alkylene, $(C_2-C_6)$alkenylene or $(C_2-C_6)$alkynylene group, wherein 1 to 4 methylene groups are optionally replaced by groups independently selected from the group consisting of O, $-S(O)_p-$, $-N(R^b)-$, and $-C(O)-$;

wherein alkylene, alkenylene, and alkynylene are unsubstituted or substituted independently with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxyl, hydroxyalkyl, keto, thiocarbonyl, carboxy, alkylcarboxy, carboxyalkyl, carboxyalkyloxy, alkylcarboxyalkyloxy $-SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $S(O)_2NR^cR^c$, $-NR^cS(O)_2R^c$ or $-S(O)_pR^d$;

wherein each substituent is unsubstituted or substituted with 1, 2, or 3 substituents independently selected from the group consisting of alkyl, carboxy, carboxyalkyl, aminocarbonyl, hydroxyl, alkoxy, halogen, $CF_3$, amino, substituted amino, cyano and $-S(O)_pR^d$;

B is heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxyl, hydroxyalkyl, keto, thiocarbonyl, carboxy, alkylcarboxy, carboxyalkyl, carboxyalkyloxy, alkylcarboxyalkyloxy $-SO_3H$, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, $S(O)_2NR^bR^b$, $-NR^bS(O)_2R^b$ or $-S(O)_pR^d$;

wherein each substituent is unsubstituted or substituted with 1, 2, or 3 substituents independently selected from the group consisting of alkyl, carboxy, carboxyalkyl, aminocarbonyl, hydroxyl, alkoxy, alkoxyalkoxy, alkoxyalkyl, halogen, haloalkyl, haloalkoxy, amino, substituted amino, cyano and $-S(O)_pR^d$;

$R^a$ is independently selected from the group consisting of hydrogen and alkyl;

$R^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

$R^c$ is selected from the group consisting of hydrogen, alkyl, aryl, heteroaryl and heterocyclyl;

$R^d$ is selected from the group consisting of alkyl, cycloalkyl, aryl, heterocyclyl and heteroaryl; and p is 0, 1 or 2.

3. A compound of formula (I) as claimed in claim 1 or its tautomers, stereoisomers, or pharmaceutically acceptable salts thereof, wherein Y is CR; R is H, hydroxy, alkoxy, alkyl, or aryl;

$R^1$ is selected from the group consisting of alkyl, alkenyl and alkynyl, wherein alkyl, alkenyl and alkynyl are unsubstituted or substituted independently with alkoxy, acyl, acylamino, acyloxy, amino, monoalkylamino, dialkylamino, aminocarbonyl, alkoxycarbonylamino, azido, cyano, halogen, haloalkyl, hydroxy, hydroxyalkyl, keto, thiocarbonyl, carboxy, alkylcarboxy or carboxyalkyl;

$R^2$ is selected from the group consisting of halogen, cyano, nitro, carboxy, acyl, aminocarbonyl, hydroxyalkyl, haloalkyl, haloalkyloxy, alkoxy, and $-NR^bR^b$;

wherein alkoxy and $R^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, $-SO_3H$, arylamino, cycloalkylamino, heteroarylamino, heterocyclylamino, aminocarbonyl, alkoxycarbonylamino, cycloalkyl or cycloalkenyl;

$R^3$ is selected from the group consisting of hydrogen, alkyl, alkenyl, alkynyl, cycloalkyl, cycloalkylalkyl, aryl, arylalkyl, heteroaryl and heteroarylalkyl;

X is optionally substituted arylene or optionally substituted heteroarylene;

A is $(C_1-C_6)$alkylene, $(C_2-C_6)$alkenylene or $(C_2-C_6)$alkynylene group, wherein 1 to 4 methylene groups are optionally replaced by groups independently selected from the group consisting of O, $-S(O)_p-$, $-N(R^b)-$, and $-C(O)-$;

B is heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy $-SO_3H$, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, $S(O)_2NR^bR^b$, $-NR^bS(O)_2R^b$ or $-S(O)_pR^d$;

wherein each substituent is unsubstituted or substituted with 1, 2, or 3 substituents independently selected from the group consisting of alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano and $-S(O)_pR^d$;

$R^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

$R^d$ is selected from the group consisting of alkyl, cycloalkyl, aryl, heterocyclyl and heteroaryl;

and p is 0, 1 or 2.

4. A compound of formula (I) as claimed in claim 1 or its tautomers, stereoisomers, or pharmaceutically acceptable salts thereof, wherein Y is N or CR; R is H, hydroxy, alkoxy, alkyl, or aryl;

$R^1$ is selected from the group consisting of alkyl, alkenyl and alkynyl;

$R^2$ is selected from the group consisting of halogen, cyano, nitro, carboxy, acyl, alkoxy, —NR$^b$R$^b$, cycloalkyl, cycloalkyoxy, and aryloxy;

wherein alkoxy, cycloalkyl, cycloalkyoxy, aryloxy, and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl or cycloalkenyl;

$R^3$ is selected from the group consisting of hydrogen, alkyl, alkenyl, alkynyl, alkoxyalkyl, cycloalkyl, cycloalkylalkyl, aryl, arylalkyl, heteroaryl and heteroarylalkyl;

X is optionally substituted phenyl;

A is $(C_1-C_6)$alkylene, $(C_2-C_6)$alkenylene or $(C_2-C_6)$alkynylene group wherein 1 to 4 methylene groups are optionally replaced by groups independently selected from the group consisting of O, —S(O)$_p$—, —N(R$^b$)—, and —C(O)—;

B is heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano and —S(O)$_p$R$^d$;

$R^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

$R^d$ is selected from the group consisting of alkyl, cycloalkyl, aryl, heterocyclyl and heteroaryl;

and p is 0, 1 or 2.

5. A compound of formula (I) as claimed in claim 1 or its tautomers, stereoisomers, or pharmaceutically acceptable salts thereof, wherein Y is N or CR; R is H, hydroxyl, alkoxy, alkyl, or aryl;

$R^1$ is selected from the group consisting of alkyl, alkenyl and alkynyl;

wherein alkyl, alkenyl and alkynyl are unsubstituted or substituted independently with alkoxy, acyl, acylamino, acyloxy, amino, monoalkylamino, dialkylamino, aminocarbonyl, alkoxycarbonylamino, azido, cyano, halogen, haloalkyl, hydroxyl, hydroxyalkyl, keto, thiocarbonyl, carboxy, alkylcarboxy, carboxyalkyl, —SO$_3$H, aminocarbonylamino, hydroxyamino, alkoxyamino or nitro;

$R^2$ is selected from the group consisting of halogen, cyano, nitro, carboxy, acyl, aminocarbonyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, arylalkyl, and aryloxy;

wherein alkoxy, carboxyalkyl, cycloalkyl, cycloalkylalkyl, cycloalkyloxy, arylalkyl, aryloxy, and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxyl, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, aryl, aryloxy, heterocyclyl, heterocyclyloxy, heteroaryl, heteroaryloxy, S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxyl, alkoxy, halogen, haloalkyl, haloalkoxy, amino, substituted amino, cyano and —S(O)$_p$R$^d$;

$R^3$ is selected from the group consisting of hydrogen, alkyl, alkenyl and alkynyl;

wherein alkyl, alkenyl and alkynyl are unsubstituted or substituted independently with alkyl, alkenyl, alkynyl, alkoxy, cycloalkyl, acyl, acylamino, acyloxy, amino, monoalkylamino, dialkylamino, aryl amino, cycloalkylamino, heteroarylamino, heterocyclylamino, aminocarbonyl, alkoxycarbonylamino, azido, cyano, halogen, hydroxyl, hydroxyalkyl, keto, thiocarbonyl, carboxy, alkylcarboxy, carboxyalkyl, carboxyalkyloxy, alkylcarboxyalkyloxy, —SO$_3$H, aryl, aryloxy, cycloalkyloxy, heteroaryl, aminocarbonylamino, heteroaryloxy, heterocyclyl, heterocyclyloxy, hydroxyamino, alkoxyamino or nitro;

X is optionally substituted heteroarylene;

A is $(C_1-C_6)$alkylene, $(C_2-C_6)$alkenylene or $(C_2-C_6)$alkynylene group, wherein 1 to 4 methylene groups are optionally replaced by groups independently selected from the group consisting of O, —S(O)$_p$—, —N(R$^b$)—, and —C(O)—;

wherein alkylene, alkenylene, and alkynylene are unsubstituted or substituted independently with alkyl, alkenyl, alkynyl, alkoxy, cycloalkyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxyl, hydroxyalkyl, keto, thiocarbonyl, carboxy, alkylcarboxy, carboxyalkyl, carboxyalkyloxy, alkylcarboxyalkyloxy —SO$_3$H, aryl, acyloxy, cycloalkyloxy, heteroaryl, aminocarbonylamino, heteroaryloxy, heterocyclyl, heterocyclyloxy, hydroxyamino, alkoxyamino or nitro;

B is heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxyl, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, $S(O)_2NR^bR^b$, $-NR^bS(O)_2R^b$ or $-S(O)_pR^d$;

wherein each substituent is unsubstituted or substituted with 1, 2, or 3 substituents independently selected from the group consisting of alkyl, carboxy, carboxyalkyl, aminocarbonyl, hydroxyl, alkoxy, alkoxyalkoxy, alkoxyalkyl, halogen, haloalkyl, haloalkoxy, amino, substituted amino, cyano and $-S(O)_pR^d$;

$R^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

$R^c$ is selected from the group consisting of hydrogen, alkyl, aryl, heteroaryl and heterocyclyl;

$R^d$ is selected from the group consisting of alkyl, cycloalkyl, aryl, heterocyclyl and heteroaryl;

and p is 0, 1 or 2.

6. A compound of formula (I) as claimed in claim 1 or its tautomers, stereoisomers, or pharmaceutically acceptable salts thereof, wherein X is

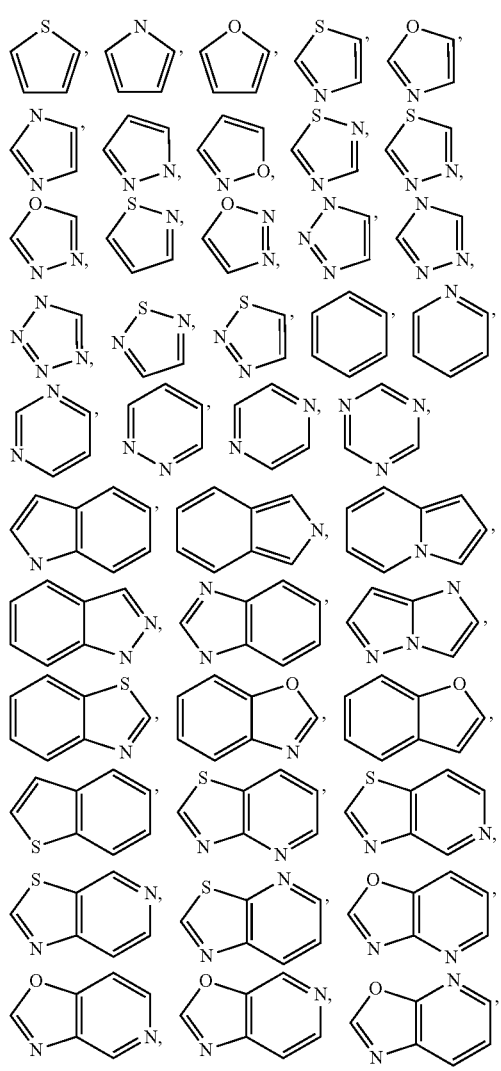

7. A compound of formula (I) as claimed in claim 1 or its tautomers, stereoisomers, or pharmaceutically acceptable salts thereof, wherein B is

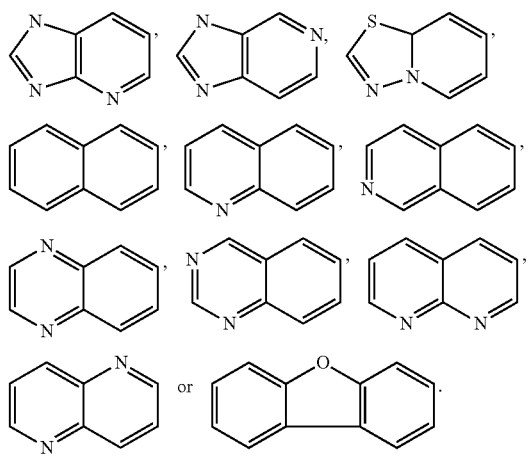

107
-continued

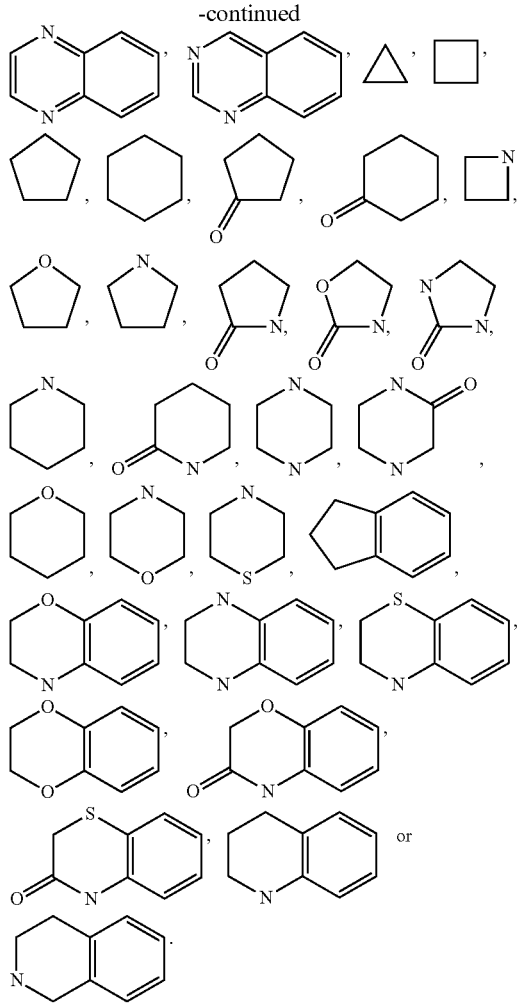

8. A compound of formula (I) as claimed in claim 1 or its tautomers, stereoisomers, or pharmaceutically acceptable salts thereof, wherein A is

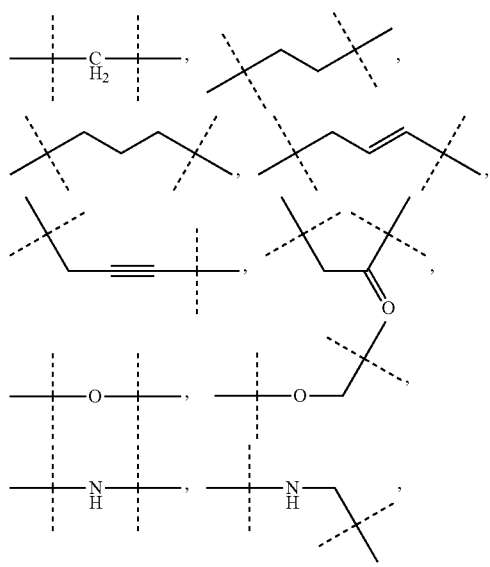

108
-continued

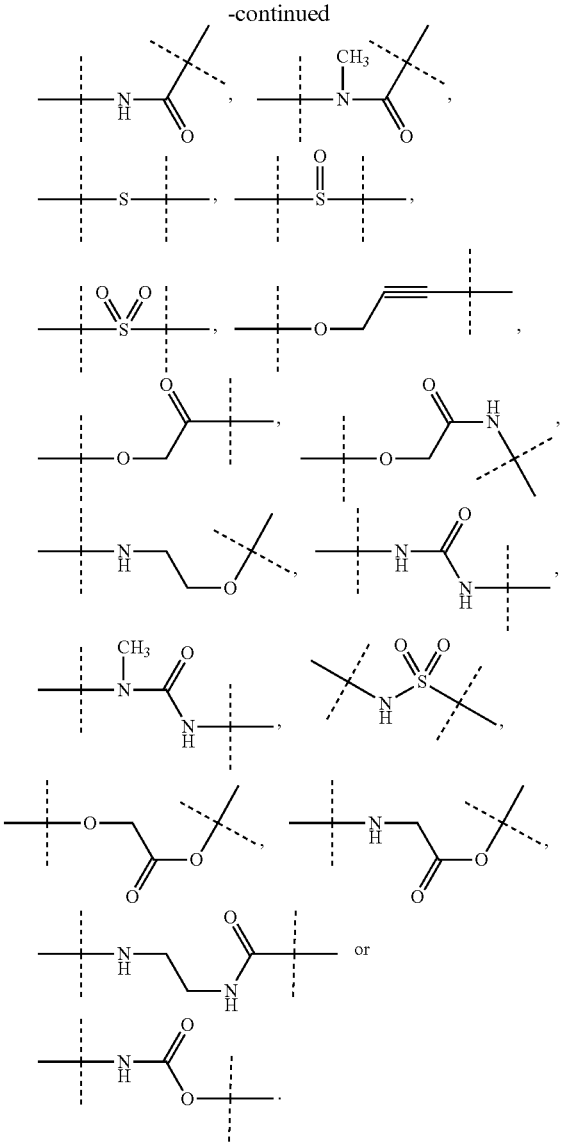

9. A compound of formula (I) as claimed in claim 1 or its tautomers, stereoisomers, or pharmaceutically acceptable salts thereof, wherein
Y is N or CR; R is H, hydroxy, alkoxy, alkyl, or aryl;
$R^1$ is alkyl wherein alkyl is unsubstituted or substituted independently with alkoxy, acyl, acylamino, acyloxy, cyano, halogen, hydroxy, carboxy, carboxyalkyl or nitro;
$R^2$ is selected from the group consisting of halogen, cyano, nitro, carboxy, acyl, aminocarbonyl, hydroxyalkyl, carboxyalkyl, alkoxy, —$NR^bR^b$, cycloalkyl, arylalkyl, and aryloxy;
wherein alkoxy, cycloalkyl, arylalkyl, and $R^b$ are unsubstituted or substituted independently with alkyl, alkoxy, acyl, acyloxy, nitro, amino, hydroxyamino, alkoxyamino, aminocarbonylamino, cyano, halogen, hydroxy, hydroxyalkyl, carboxy, alkylcarboxy, carboxyalkyl, —$SO_3H$, aminocarbonyl, cycloalkyl, cycloalkyloxy, aryl, aryloxy, heterocyclyl, heterocylyloxy, heteroaryl or heteroaryloxy;
$R^3$ is selected from the group consisting of hydrogen, alkyl, aryl and arylalkyl;

wherein alkyl, aryl and arylalkyl are unsubstituted or substituted independently with alkyl, acyl, acylamino, acyloxy, amino, cyano, halogen, hydroxy, carboxy, alkylcarboxy or carboxyalkyl;

X is optionally substituted arylene or optionally substituted heteroarylene;

A is ($C_1$-$C_6$)alkylene, ($C_2$-$C_6$)alkenylene or ($C_2$-$C_6$)alkynylene group wherein 1 to 4 methylene groups are optionally replaced by groups independently selected from the group consisting of O, —S(O)$_p$—, —N($R^b$)—, and —C(O)—;

B is heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano and —S(O)$_p$R$^c$;

R$^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

R$^c$ is selected from the group consisting of hydrogen, alkyl, aryl, heteroaryl and heterocyclyl;

R$^d$ is selected from the group consisting of alkyl, cycloalkyl, aryl, heterocyclyl and heteroaryl;

and p is 0, 1 or 2.

10. A compound of formula (I) as claimed in claim 1 or its tautomers, stereoisomers, or pharmaceutically acceptable salts thereof, wherein Y is N;

R$^1$ is alkyl, wherein one or more methylene groups are optionally replaced by hetero atoms or groups selected from —O—, S(O)$_p$, —N(R$^a$)—, or —C(O), provided heteroatom is not adjacent to N in the ring; p is 0, 1 or 2;

wherein alkyl is unsubstituted or substituted independently with alkoxy, acyl, acylamino, acyloxy, amino, monoalkylamino, dialkylamino, aminocarbonyl, alkoxycarbonylamino, cyano, halogen, haloalkyl, hydroxy, hydroxyalkyl, thiocarbonyl, carboxy, alkylcarboxy, carboxyalkyl, —SO$_3$H, aminocarbonylamino, hydroxyamino, alkoxyamino, —S(O)$_2$NR$^a$R$^a$, —NR$^a$S(O)$_2$R$^a$, or —S(O)$_p$R$^a$;

R$^2$ is selected from the group consisting of halogen, cyano, nitro, carboxy, acyl, aminocarbonyl, hydroxyalkyl, carboxyalkyl, haloalkyl, haloalkyloxy, alkoxy, —NR$^b$R$^b$, —S(O)$_p$R$^b$, cycloalkyl, cycloalkylalkyl, cycloalkyloxy, arylalkyl, and aryloxy;

wherein alkoxy, carboxyalkyl, cycloalkyl, cycloalkylalkyl, cycloalkyloxy, arylalkyl, aryloxy, and R$^b$ are unsubstituted or substituted independently with alkyl, alkenyl, alkynyl, alkoxy, acyl, acylamino, acyloxy, nitro, amino, monoalkylamino, dialkylamino, hydroxyamino, alkoxyamino, aminocarbonylamino, azido, cyano, halogen, hydroxy, hydroxyalkyl, keto, thiocarbonyl, carboxy, alkylcarboxy, carboxyalkyl, —SO$_3$H, arylamino, cycloalkylamino, heteroarylamino, heterocyclylamino, aminocarbonyl, alkoxycarbonylamino, cycloalkyl, cycloalkyloxy, cycloalkenyl, aryl, aryloxy, heteroaryl, heteroaryloxy, heterocyclyl, heterocyclyloxy, —S(O)$_2$NR$^c$R$^c$, —NR$^c$S(O)$_2$R$^c$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxy, alkoxy, halogen, haloalkyl, haloalkoxy, amino, substituted amino, cyano and —S(O)$_p$R$^d$;

R$^3$ is selected from the group consisting of hydrogen, alkyl and arylalkyl;

X is optionally substituted heteroarylene;

A is ($C_1$-$C_6$)alkylene, ($C_2$-$C_6$)alkenylene or ($C_2$-$C_6$)alkynylene group wherein 1 to 4 methylene groups are optionally replaced by groups independently selected from the group consisting of O, —S(O)$_p$—, —N($R^b$)—, and —C(O)—;

wherein alkylene, alkenylene, and alkynylene are unsubstituted or substituted independently with alkyl, alkoxy, cycloalkyl, halogen, hydroxy, hydroxyalkyl, carboxy, alkylcarboxy, carboxyalkyl, carboxyalkyloxy, —SO$_3$H, hydroxyamino, alkoxyamino, S(O)$_2$NR$^c$R$^c$, —NR$^c$S(O)$_2$R$^c$ or —S(O)$_p$R$^d$;

B is heterocyclyl, cycloalkyl, aryl or heteroaryl;

wherein heterocyclyl, cycloalkyl, aryl and heteroaryl are unsubstituted or substituted independently with alkyl, alkenyl, alkynyl, alkoxy, cycloalkyl, cycloalkylalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —SO$_3$H, aryl, arylalkyl, aryloxy, cycloalkyloxy, heteroaryl, heteroarylalkyl, aminocarbonylamino, heteroaryloxy, heterocyclyl, heterocyclylalkyl, heterocyclyloxy, hydroxyamino, alkoxyamino, nitro, S(O)$_2$NR$^b$R$^b$, —NR$^b$S(O)$_2$R$^b$ or —S(O)$_p$R$^d$;

wherein each substituent is unsubstituted or substituted with 1, 2, or 3 substituents independently selected from the group consisting of alkyl, carboxy, carboxyalkyl, aminocarbonyl, hydroxy, alkoxy, alkoxyalkoxy, alkoxyalkyl, halogen, haloalkyl, haloalkoxy, amino, substituted amino, cyano and —S(O)$_p$R$^d$;

R$^a$ is independently selected from the group consisting of hydrogen and alkyl;

R$^b$ is independently selected from the group consisting of hydrogen, alkyl, acyl, carboxyalkyl, carbonylamino, cycloalkyl, cycloalkylalkyl, aryl, arylalkyl, heteroaryl heteroarylalkyl, heterocyclyl and heterocyclylalkyl;

R$^c$ is selected from the group consisting of hydrogen, alkyl, aryl, heteroaryl and heterocyclyl;

R$^d$ is selected from the group consisting of alkyl, cycloalkyl, aryl, heterocyclyl and heteroaryl;

and p is 0, 1 or 2.

11. A compound of formula (I) as claimed in claim 1 or its tautomers, stereoisomers, or pharmaceutically acceptable salts thereof, which is 2-Chloro-8-[1-(2,3-difluoro-benzyl)-1H-pyrazol-4-yl]-1-propyl-1,7-dihydro-purin-6-one, 2-Chloro-8-[1-(3-fluoro-4-trifluoromethyl-benzyl)-1H-pyrazol-4-yl]-1-propyl-1,7-dihydro-purin-6-one, 2-Chloro-1-propyl-8-[1-(4-trifluoromethyl-benzyl)-1H-pyrazol-4-yl]-1,7-dihydro-purin-6-one,
2-Chloro-8-[1-(3-fluoro-benzyl)-1H-pyrazol-4-yl]-1-propyl-1,7-dihydro-purin-6-one,
2-Chloro-1-propyl-8-[1-(3-trifluoromethyl-benzyl)-1H-pyrazol-4-yl]-1,7-dihydro-purin-6-one,
2-Chloro-8-[1-(2,4-difluoro-benzyl)-1H-pyrazol-4-yl]-1-propyl-1,7-dihydro-purin-6-one,
8-(1-Benzyl-1H-pyrazol-4-yl)-2-chloro-1-propyl-1,7-dihydro-purin-6-one,
8-(1-Benzyl-1H-pyrazol-4-yl)-1-propyl-2-(4-trifluoromethyl-benzylamino)-1,7-dihydro-purin-6-one,
8-(1-Benzyl-1H-pyrazol-4-yl)-1-propyl-2-(3-trifluoromethyl-benzylamino)-1,7-dihydro-purin-6-one,
8-(1-Benzyl-1H-pyrazol-4-yl)-2-[2-(4-methoxy-phenyl)-ethylamino]-1-propyl-1,7-dihydro-purin-6-one,
8-(1-Benzyl-1H-pyrazol-4-yl)-2-phenethylamino-1-propyl-1,7-dihydro-purin-6-one,
8-[1-(3-Fluoro-4-trifluoromethyl-benzyl)-1H-pyrazol-4-yl]-2-(2-hydroxy-ethylamino)-1-propyl-1,7-dihydro-purin-6-one,
2-Amino-1-propyl-8-[1-(3-trifluoromethyl-benzyl)-1H-pyrazol-4-yl]-1,7-dihydro-purin-6-one,
8-(1-Benzyl-1H-pyrazol-4-yl)-2-methylamino-1-propyl-1,7-dihydro-purin-6-one,
[8-(1-Benzyl-1H-pyrazol-4-yl)-6-oxo-1-propyl-6,7-dihydro-1H-purin-2-ylamino]-acetic acid ethyl ester,
8-(1-Benzyl-1H-pyrazol-4-yl)-2-methoxy-1-propyl-1,7-dihydro-purin-6-one,
2-Dimethylamino-1-propyl-8-[1-(3-trifluoromethyl-benzyl)-1H-pyrazol-4-yl]-1,7-dihydro-purin-6-one,
8-[1-(3-Fluoro-4-trifluoromethyl-benzyl)-1H-pyrazol-4-yl]-6-oxo-1-propyl-6,7-dihydro-1H-purine-2-carbonitrile,
8-[1-(3-Fluoro-4-trifluoromethyl-benzyl)-1H-pyrazol-4-yl]-6-oxo-1-propyl-6,7-dihydro-1H-purine-2-carboxylic acid,
2-Benzyl-1-propyl-8-[1-(3-trifluoromethyl-benzyl)-1H-pyrazol-4-yl]-1,7-dihydro-purin-6-one,
{6-Oxo-1-propyl-8-[1-(3-trifluoromethyl-benzyl)-1H-pyrazol-4-yl]-6,7-dihydro-1H-purin-2-ylamino}-acetic acid,
2-Methylamino-1-propyl-8-[1-(3-trifluoromethyl-benzyl)-1H-pyrazol-4-yl]-1,7-dihydro-purin-6-one,
2-Cyclobutylamino-1-propyl-8-[1-(3-trifluoromethyl-benzyl)-1H-pyrazol-4-yl]-1,7-dihydro-purin-6-one,
2-Chloro-8-[1-(3-fluoro-4-trifluoromethyl-benzyl)-1H-pyrazol-4-yl]-7-methyl-1-propyl-1,7-dihydro-purin-6-one,
2-Methoxy-1-propyl-8-[1-(3-trifluoromethyl-benzyl)-1H-pyrazol-4-yl]-1,7-dihydro-purin-6-one,
6-Oxo-1-propyl-8-[1-(3-trifluoromethyl-benzyl)-1H-pyrazol-4-yl]-6,7-dihydro-1H-purine-2-carbonitrile,
2-Cyclopentyloxy-1-propyl-8-[1-(3-trifluoromethyl-benzyl)-1H-pyrazol-4-yl]-1,7-dihydro-purin-6-one,
6-Oxo-1-propyl-8-[1-(3-trifluoromethyl-benzyl)-1H-pyrazol-4-yl]-6,7-dihydro-1H-purine-2-carboxylic acid amide,
{6-Oxo-1-propyl-8-[1-(3-trifluoromethyl-benzyl)-1H-pyrazol-4-yl]-6,7-dihydro-1H-purin-2-yloxy}-acetic acid ethyl ester,
{6-Oxo-1-propyl-8-[1-(3-trifluoromethyl-benzyl)-1H-pyrazol-4-yl]-6,7-dihydro-1H-purin-2-yloxy}-acetic acid,
2-(2,3-Dihydroxy-propylamino)-1-propyl-8-[1-(3-trifluoromethyl-benzyl)-1H-pyrazol-4-yl]-1,7-dihydro-purin-6-one,
2-(2-Methoxy-ethylamino)-1-propyl-8-[1-(3-trifluoromethyl-benzyl)-1H-pyrazol-4-yl]-1,7-dihydro-purin-6-one,
2-{6-Oxo-1-propyl-8-[1-(3-trifluoromethyl-benzyl)-1H-pyrazol-4-yl]-6,7-dihydro-1H-purin-2-ylamino}-ethanesulfonic acid,
(Methyl-{6-oxo-1-propyl-8-[1-(3-trifluoromethyl-benzyl)-1H-pyrazol-4-yl]-6,7-dihydro-1H-purin-2-yl}-amino)-acetic acid,
2-(2-Hydroxy-ethylamino)-1-propyl-8-[1-(3-trifluoromethyl-benzyl)-1H-pyrazol-4-yl]-1,7-dihydro-purin-6-one,
(S)-3-Methyl-2-{6-oxo-1-propyl-8-[1-(3-trifluoromethyl-benzyl)-1H-pyrazol-4-yl]-6,7-dihydro-1H-purin-2-ylamino}-butyric acid,
1-Propyl-2-(tetrahydro-pyran-4-ylamino)-8-[1-(3-trifluoromethyl-benzyl)-1H-pyrazol-4-yl]-1,7-dihydro-purin-6-one,
2-Fluoro-1-propyl-8-[1-(3-trifluoromethyl-benzyl)-1H-pyrazol-4-yl]-1,7-dihydro-purin-6-one,
1-Propyl-2-(2,2,2-trifluoro-ethoxy)-8-[1-(3-trifluoromethyl-benzyl)-1H-pyrazol-4-yl]-1,7-dihydro-purin-6-one,
2-(2-Methoxy-ethoxy)-1-propyl-8-[1-(3-trifluoromethyl-benzyl)-1H-pyrazol-4-yl]-1,7-dihydro-purin-6-one,
2-Chloro-1-propyl-8-[6-(3-trifluoromethyl-benzylamino)-pyridin-3-yl]-1,7-dihydro-purin-6-one,
2-Chloro-8-[6-(3-fluoro-benzylamino)-pyridin-3-yl]-1-propyl-1,7-dihydro-purin-6-one,
2-Cyclopropyl-1-propyl-8-[1-(3-trifluoromethyl-benzyl)-1H-pyrazol-4-yl]-1,7-dihydro-purin-6-one,
2-Difluoromethoxy-1-propyl-8-[1-(3-trifluoromethyl-benzyl)-1H-pyrazol-4-yl]-1,7-dihydro-purin-6-one,
1-Propyl-2-trifluoromethyl-8-[1-(3-trifluoromethyl-benzyl)-1H-pyrazol-4-yl]-1,7-dihydro-purin-6-one,
2-Chloro-8-(1-methyl-1H-pyrazol-4-yl)-1-propyl-1,7-dihydro-purin-6-one,
2-Amino-8-[1-(4-fluoro-benzyl)-1H-imidazo[1,2-b]pyrazol-7-yl]-1-propyl-1,7-dihydro-purin-6-one,
2-Chloro-8-[1-(4-fluoro-benzyl)-1H-imidazo[1,2-b]pyrazol-7-yl]-1-propyl-1,7-dihydro-purin-6-one,
2-Chloro-8-(6-chloro-pyridin-3-yl)-1-propyl-1,7-dihydro-purin-6-one,
2-Difluoromethyl-1-propyl-8-[1-(3-trifluoromethyl-benzyl)-1H-pyrazol-4-yl]-1,7-dihydro-purin-6-one,
2-Fluoromethyl-1-propyl-8-[1-(3-trifluoromethyl-benzyl)-1H-pyrazol-4-yl]-1,7-dihydro-purin-6-one,
2-Fluoromethyl-8-{1-[3-(3-methoxy-phenyl)-prop-2-ynyl]-1H-pyrazol-4-yl}-1-propyl-1,7-dihydro-purin-6-one,
2-Difluoromethyl-8-{1-[2-oxo-2-(4-m-tolyl-piperazin-1-yl)-ethyl]-1H-pyrazol-4-yl}-1-propyl-1,7-dihydro-purin-6-one,
N-[5-(2-D fluoromethyl-6-oxo-1-propyl-6,7-dihydro-1H-purin-8-yl)-pyridin-2-yl]-3-methoxy-N-methyl-benzamide,
N-[5-(2-Difluoromethyl-6-oxo-1-propyl-6,7-dihydro-1H-purin-8-yl)-pyridin-2-yl]-3-methoxy-benzenesulfonamide,
2-Fluoromethyl-1-propyl-8-[1-(5-trifluoromethyl-pyridin-3-ylmethyl)-1H-pyrazol-4-yl]-1,7-dihydro-purin-6-one,
2-Fluoromethyl-1-propyl-8-[1-(2-trifluoromethyl-pyridin-4-ylmethyl)-1H-pyrazol-4-yl]-1,7-dihydro-purin-6-one,
2-Fluoromethyl-8-[3-(3-methoxy-phenoxy)-isoxazol-5-yl]-1-propyl-1,7-dihydro-purin-6-one, 2-Difluoromethyl-8-{3-[3-(3-fluoro-phenyl)-prop-2-ynyloxy]-isoxazol-5-yl}-1-propyl-1,7-dihydro-purin-6-one, 2-Fluoromethyl-1-(2-hydroxy-ethyl)-8-[3-(3-methoxy-phenoxy)-isoxazol-5-yl]-1,7-dihydro-purin-6-one, 2-Difluoromethyl-1-ethyl-8-{3-[3-(3-fluoro-phenyl)-prop-2-ynyloxy]-isoxazol-5-yl}-1,7-dihydro-purin-6-one, 2-Difluoromethyl-1-ethyl-8-(1-{2-[4-(3-methoxy-phenyl)-piperazin-1-yl]-2-oxo-ethyl}-1H-pyrazol-4-yl)-1,7-dihydro-purin-6-one, 1-Ethyl-8-(1-{2-[4-(3-methoxy-phenyl)-piperazin-1-yl]-2-oxo-ethyl}-1H-pyrazol-4-yl)-6-oxo-6,7-dihydro-1H-purine-2-carbonitrile, N-[5-(2-Cyano-6-oxo-1-propyl-6,7-dihydro-1H-purin-8-yl)-pyridin-2-yl]-3-methoxy-benzenesulfonamide, N-{5-[2-Cyano-1-(2-hydroxy-ethyl)-6-oxo-6,7-dihydro-1H-purin-8-yl]-pyridin-2-yl}-3-methoxy-benzenesulfonamide, 2-Difluoromethyl-1-ethyl-8-{4-[3-(3-methoxy-phenyl)-prop-2-ynyloxy]-phenyl}-1,7-dihydro-purin-6-one, 2-Difluoromethyl-1-ethyl-8-{4-[1-(3-fluoro-phenyl)-5-oxo-pyrrolidin-3-ylmethoxy]-phenyl}-1,7-dihydro-purin-6-one, 2-Difluoromethyl-8-[5-(3-methoxy-phenoxy)-1-methyl-1H-pyrazol-3-yl]-1-propyl-1,7-dihydro-purin-6-one, 2-Difluoromethyl-8-{5-[1-(3-methoxy-phenyl)-piperidin-4-yloxy]-1-methyl-1H-pyrazol-3-yl}-1-propyl-1,7-dihydro-purin-6-one, 2-Fluoromethyl-8-{3-[1-(3-fluoro-phenyl)-piperidin-4-yloxy]-isoxazol-5-yl}-1-propyl-1,7-dihydro-purin-6-one, 1-Ethyl-8-{6-[1-(3-fluoro-phenyl)-5-oxo-pyrrolidin-3-ylmethoxy]-pyridin-3-yl}-6-oxo-6,7-dihydro-1H-purine-2-carbonitrile, 1-Ethyl-8-{6-[1-(3-methoxy-phenyl)-pyrrolidin-3-yloxy]-pyridin-3-yl}-6-oxo-6,7-dihydro-1H-purine-2-carbonitrile, 3-[4-(2-Difluoromethyl-1-ethyl-6-oxo-6,7-dihydro-1H-purin-8-yl)-pyrazol-1-ylmethyl]-benzoic acid, 2-Difluoromethyl-1-ethyl-8-[1-(3-hydroxymethyl-benzyl)-1H-pyrazol-4-yl]-1,7-dihydro-purin-6-one, 2-Difluoromethyl-3-ethyl-6-[1-(3-methoxy-benzyl)-1H-pyrazol-4-yl]-3,5-dihydro-pyrrolo[3,2-d]pyrimidin-4-one, N-[5-(2-Cyano-4-oxo-3-propyl-4,5-dihydro-3H-pyrrolo[3,2-d]pyrimidin-6-yl)-pyridin-2-yl]-3-methoxy-benzenesulfonamide, 2-Fluoromethyl-6-{3-[1-(3-fluoro-phenyl)-piperidin-4-yloxy]-isoxazol-5-yl}-3-propyl-3,5-dihydro-pyrrolo[3,2-d]pyrimidin-4-one, 2-Difluoromethyl-6-{5-[1-(3-methoxy-phenyl)-piperidin-4-yloxy]-1-methyl-1H-pyrazol-3-yl}-3-propyl-3,5-dihydro-pyrrolo[3,2-d]pyrimidin-4-one, 3-Ethyl-6-{6-[1-(3-methoxy-phenyl)-pyrrolidin-3-yloxy]-pyridin-3-yl}-4-oxo-4,5-dihydro-3H-pyrrolo[3,2-d]pyrimidine-2-carbonitrile, 2-Fluoromethyl-6-{3-[1-(3-fluoro-phenyl)-piperidin-4-yloxy]-isoxazol-5-yl}-7-hydroxy-3-propyl-3,5-dihydro-pyrrolo[3,2-d]pyrimidin-4-one, 2-Difluoromethyl-3-ethyl-6-[1-(3-methoxy-benzyl)-1H-pyrazol-4-yl]-7-methyl-3,5-dihydro-pyrrolo[3,2-d]pyrimidin-4-one, 2-Difluoromethyl-1-ethyl-8-[1-(3-methoxy-benzyl)-1H-pyrazol-4-yl]-7-methyl-1,7-dihydro-purin-6-one, N-[5-(2-Cyano-7-methyl-6-oxo-1-propyl-6,7-dihydro-1H-purin-8-yl)-pyridin-2-yl]-3-methoxy-benzenesulfonamide, 3-{3-[4-(2-Difluoromethyl-6-oxo-1-propyl-6,7-dihydro-1H-purin-8-yl)-pyrazol-1-yl]-prop-1-ynyl}-benzoic acid, 3-{3-[4-(6-Oxo-1-propyl-2-trifluoromethyl-6,7-dihydro-1H-purin-8-yl)-pyrazol-1-yl]-prop-1-ynyl}-benzoic acid, or 6-Oxo-1-propyl-8-[6-(3-trifluoromethyl-benzyl)-pyridin-3-yl]-6,7-dihydro-1H-purine-2-carbonitrile.

12. A pharmaceutical composition comprising, as an active ingredient, at least one compound of formula (I), as claimed in claim 1, or its tautomers, stereoisomers, or pharmaceutically acceptable salts thereof, together with one or more pharmaceutically acceptable carriers or excipients.

13. A pharmaceutical composition comprising, a compound of formula (I) as claimed in claim 1, or its tautomers, stereoisomers, or pharmaceutically acceptable salts thereof, in combination with one or more therapeutically active agents.

* * * * *